(12) United States Patent
Chasin et al.

(10) Patent No.: US 6,372,770 B1
(45) Date of Patent: Apr. 16, 2002

(54) BENZOXAZOLES

(75) Inventors: Mark Chasin, Manalapan, NJ (US); David Cavalla, Cambridge (GB); Peter Hofer, Liestal (CH); Lloyd Dolby, Eugene, OR (US)

(73) Assignee: Euro-Celtique, S.A.

( * ) Notice: Subject to any disclaimer, the term of this patent is extended or adjusted under 35 U.S.C. 154(b) by 0 days.

(21) Appl. No.: 09/151,949

(22) Filed: Sep. 11, 1998

Related U.S. Application Data

(63) Continuation of application No. 08/833,897, filed on Apr. 10, 1997, now abandoned, which is a continuation-in-part of application No. PCT/US95/14399, filed on Oct. 11, 1995, which is a continuation-in-part of application No. 08/467,091, filed on Jun. 6, 1995, now abandoned, which is a continuation-in-part of application No. 08/321,730, filed on Oct. 12, 1994, now Pat. No. 5,665,737.

(51) Int. Cl.[7] .................. A61K 31/42; C07D 263/54; A61P 11/06; A61P 25/28; A61P 37/08

(52) U.S. Cl. .................. 514/375; 548/152; 548/178; 548/179; 548/181; 548/217; 548/224; 546/271.7; 514/338; 514/365; 514/367

(58) Field of Search .................. 514/375; 548/217, 548/224

(56) References Cited

U.S. PATENT DOCUMENTS

| | | | |
|---|---|---|---|
| 2,320,654 A | 6/1943 | Riester | 95/7 |
| 3,136,771 A | 6/1964 | Liechti et al. | 260/296 |
| 3,262,929 A | 7/1966 | Okubu et al. | 260/240 |
| 3,470,164 A | 9/1969 | Takamatsu et al. | 260/240 |
| 3,491,091 A | 1/1970 | Berger | 260/240 |
| 3,491,106 A | 1/1970 | Freyermuth et al. | 260/304 |
| 3,494,919 A | 2/1970 | Collins et al. | 260/240 |
| 3,541,100 A | 11/1970 | Ramirez et al. | 260/286 |
| 3,574,218 A | 4/1971 | Hideg et al. | 260/293.4 |
| 3,586,670 A | 6/1971 | Brenneisen et al. | 260/240 |
| 3,647,812 A | 3/1972 | Smith | 260/304 |
| 3,666,769 A | 5/1972 | Jones et al. | 260/304 |
| 3,669,979 A | 6/1972 | Freyermuth | 260/304 |
| 3,674,781 A | 7/1972 | Schinzel et al. | 260/240 |
| 3,706,834 A | * 12/1972 | Schellenbaum et al. | 424/272 |
| 3,899,506 A | 8/1975 | Shen et al. | 260/307 |
| 3,962,452 A | 6/1976 | Evans et al. | 424/272 |
| 4,020,165 A | 4/1977 | Hubbard | 514/367 |
| 4,025,636 A | 5/1977 | Dunwell et al. | 424/269 |
| 4,025,637 A | 5/1977 | Dunwell | 424/272 |
| 4,046,771 A | * 9/1977 | Beecken | 260/307 |
| 4,167,628 A | 9/1979 | Kormany | 542/454 |
| 4,416,892 A | 11/1983 | Dawson | 424/272 |
| 4,652,654 A | 3/1987 | Verga et al. | 548/217 |
| 4,732,978 A | 3/1988 | Kreft et al. | 546/152 |
| 4,785,115 A | 11/1988 | Tsai et al. | 548/180 |
| 4,831,152 A | 5/1989 | Itoh et al. | 548/224 |
| 4,910,211 A | 3/1990 | Imamura et al. | 514/367 |
| 5,047,411 A | 9/1991 | Takasugi et al. | 514/300 |
| 5,190,942 A | 3/1993 | Poss | 514/235.8 |
| 5,206,255 A | 4/1993 | Ubasawa et al. | 514/374 |
| 5,264,589 A | 11/1993 | Corey | 548/51 |
| 5,322,847 A | 6/1994 | Marfat et al. | 514/303 |
| 5,496,853 A | 3/1996 | Shiota et al. | 514/469 |
| 5,622,977 A | 4/1997 | Warrellow et al. | 514/336 |
| 5,633,257 A | 5/1997 | Warelloew et al. | 514/227 |
| 5,665,737 A | * 9/1997 | Cavalla et al. | 514/338 |

FOREIGN PATENT DOCUMENTS

| | | |
|---|---|---|
| CH | 555 848 | * 11/1974 |
| DE | 2008464 | 9/1970 |
| DE | 2314676 | 10/1973 |
| DE | 2346034 | 4/1974 |
| EP | 0332988 | 9/1989 |
| GB | 1260793 | 1/1972 |
| JP | 476267 | 8/1972 |
| JP | 5721375 | 2/1982 |
| JP | 59-121704 | * 7/1984 |
| JP | 2207078 | 8/1990 |
| JP | 3173874 | 7/1991 |
| JP | 03-258770 | * 11/1991 |
| JP | 5505619 | 8/1993 |
| JP | 06-258758 | * 9/1994 |
| JP | 8113567 | 7/1996 |
| WO | WO 9410118 | 5/1994 |
| WO | 9412461 | 6/1994 |
| WO | WO 9508534 | 3/1995 |
| WO | WO 9517392 | 6/1995 |
| WO | WO 9517399 | 6/1995 |
| WO | WO 9524379 | 9/1995 |

OTHER PUBLICATIONS

CAS printout for JP 03–258770, Nov. 19, 1991.*

Goldstein et al., A Facile Synthesis of Methyl 2–Substituted–4–benzoxazolecarboxylates, Journal of Heterocyclic Chemistry, vol. 27, No. 2, pp. 335–336, Feb. 1990.*

Gilchrist et al., Ring Contraction of 1,2,4–Benzoxadiazines to Benzoxazoles, Journal of the Chemical Society, Perkin Trans. 1, vol. 8, pp. 2169–2173, Aug. 1988.*

Clark et al., Preparation and Electrophilic Trapping of 7–Lithiated Benzoxazoles Generated via Benzyne Cyclization, Journal of Organic Chemistry, vol. 47, No. 14, pp. 2804–2806, Jul. 1982.*

Evans et al., Synthesis and Antiinflammatory Activity of Some 2–Substituted 4–and 7–Benzoxazoleacetic and alpha––Methylacetic Acids, Journal of Medicinal Chemistry, vol. 20, No. 1, pp. 169–171, Jan. 1977.*

Brewster et al., Oxidation of Some Dibenz[b,f][1,4]oxazepines by Peracetic Acid, Journal of the Chemical Society, Perkin Trans. 1, vol. 12, pp. 1291–1296, 1976.*

(List continued on next page.)

*Primary Examiner*—Brenda Coleman
(74) *Attorney, Agent, or Firm*—Davidson, Davidson & Kappel, LLC

(57) ABSTRACT

Novel compounds which are effective PDE IV inhibitors are disclosed. The compounds possess improved PDE IV inhibition as compared to theophylline or rolipram, with improved selectivity with regard to, e.g., PDE III inhibition.

46 Claims, No Drawings

OTHER PUBLICATIONS

Ozeki et al., chemical abstracts, 116:151764, 1992.*
English translation of JP 5721375.
Chem. Abs. 117:212391m (1992).
Chem. Abs. 119:245336t (1993).
Chem. Abs. 121:57373v (1994).
Chem. Abs. 121:134105p (1994).
Chem. Abs. 124:86997u (1995).
Chem. Abs. 124:176077y (1994).

Isomura et al., "Studies on the synthesis and anti–inflammatory activity of 2,6–Di–tert–butylphenols with a heterocyclic group at the 4–position.I", vol. 31, No. 9, pp. 3168–3178 (1983).

Grozinger et al. "Heterocyclic Ethenyloxanilates as Orally Active Antiallergic Agents"; Eur. J. Med. Chem. 1985; No. 6 pp. 487–491.

* cited by examiner

BENZOXAZOLES

This application is a continuation of application Ser. No. 08/833,897, filed Apr. 10, 1997, which is a continuation-in-part of PCT/US95/14399, filed Oct. 11, 1995 which is a continuation-in-part of both U.S. Ser. No. 08/467,091, filed Jun. 6, 1995, now abandoned and U.S. Ser. No. 08/321,730, filed Oct. 12, 1994, now U.S. Pat. No. 5,665,737.

BACKGROUND OF THE INVENTION

Asthma is a complex disease involving the concerted actions of multiple inflammatory and immune cells, spasmogens, inflammatory mediators, cytokines and growth factors. In recent practice there have been four major classes of compounds used in the treatment of asthma, namely bronchodilators (e.g., β-adrenoceptor agonists), anti-inflammatory agents (e.g., corticosteroids), prophylactic anti-allergic agents (e.g., cromolyn sodium) and xanthines (e.g., theophylline) which appear to possess both bronchodilating and anti-inflammatory activity.

Theophylline has been a preferred drug of first choice in the treatment of asthma. Although it has been touted for its direct bronchodilatory action, theophylline's therapeutic value is now believed to also stem from anti-inflammatory activity. Its mechanism of action remains unclear. However, it is believed that several of its cellular activities are important in its activity as an anti-asthmatic, including cyclic nucleotide phosphodiesterase inhibition, adenosine receptor antagonism, stimulation of catecholamine release, and its ability to increase the number and activity of suppressor T-lymphocytes. While all of these actually may contribute to its activity, only PDE inhibition may account for both the anti-inflammatory and bronchodilatory components. However, theophylline is known to have a narrow therapeutic index, and a wide range of untoward side effects which are considered problematic.

Cyclic nucleotide phosphodiesterases (PDEs) have received considerable attention as molecular targets for anti-asthmatic agents. Cyclic 3',5'-adenosine monophosphate (cAMP) and cyclic 3',5'-guanosine monophosphate (cGMP) are known second messengers that mediate the functional responses of cells to a multitude of hormones, neurotransmitters and autocoids. At least two therapeutically important effects could result from phosphodiesterase inhibition, and the consequent rise in intracellular adenosine 3',5'-monophosphate (cAMP) or guanosine 3',5'-monophosphate (cGMP) in key cells in the pathophysiology of asthma. These are smooth muscle relaxation (resulting in bronchodilation) and anti-inflammatory activity.

It has become known that there are multiple, distinct PDE isoenzymes which differ in their cellular distribution. A variety of inhibitors possessing a marked degree of selectivity for one isoenzyme or the other have been synthesized.

The structure-activity relationships (SAR) of isozyme-selective inhibitors has been discussed in detail, e.g., in the article of Theodore J. Torphy, et al., "Novel Phosphodiesterase Inhibitors For The Therapy Of Asthma", Drug News & Perspectives, 6(4) May 1993, pages 203–214. The PDE enzymes can be grouped into five families according to their specificity toward hydrolysis of cAMP or cGMP, their sensitivity to regulation by calcium, calmodulin or cGMP, and their selective inhibition by various compounds. PDE I is stimulated by $Ca^{2+}$/calmodulin. PDE II is cGMP-stimulated, and is found in the heart and adrenals. PDE III is cGMP-inhibited, and inhibition of this enzyme creates positive inotropic activity. PDE IV is cAMP specific, and its inhibition causes airway relaxation, anti-inflammatory and antidepressant activity. PDE V appears to be important in regulating cGMP content in vascular smooth muscle, and therefore PDE V inhibitors may have cardiovascular activity.

While there are compounds derived from numerous structure activity relationship studies which provide PDE III inhibition, the number of structural classes of PDE IV inhibitors is relatively limited. Analogues of rolipram, which has the following structural formula:

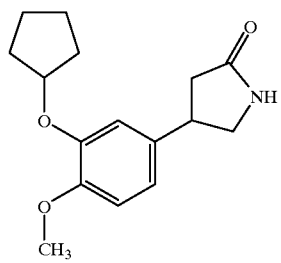

and of Ro-20-1724, which has the following structural formula:

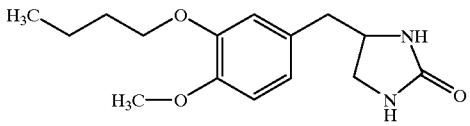

have been studied.

Rolipram, which was initially studied because of its activity as an antidepressant has been shown to selectively inhibit the PDE IV enzyme and this compound has since become a standard agent in the classification of PDE enzyme subtypes. There appears to be considerable therapeutic potential for PDE IV inhibitors. Besides initial work suggesting an anti-depressive action, rolipram has been investigated for its anti-inflammatory effects, particularly in asthma. In-vitro, rolipram, Ro-20-1724 and other PDE IV inhibitors have been shown to inhibit (1) mediator synthesis/release in mast cells, basophils, monocytes and eosinophils; (2) respiratory burst, chemotaxis and degranulation in neutrophils and eosinophils; and (3) mitogen-dependent growth and differentiation in lymphocytes (The PDE IV Family Of Calcium-Phosphodiesterases Enzymes, John A. Lowe, III, et al., Drugs of the Future 1992, 17(9):799–807).

PDE IV is present in all the major inflammatory cells in asthma including eosinophils, neutrophils, T-lymphocytes, macrophages and endothelial cells. Its inhibition causes down regulation of cellular activation and relaxes smooth muscle cells in the trachea and bronchus. On the other hand, inhibition of PDE III, which is present in myocardium, causes an increase in both the force and rate of cardiac contractility. These are undesirable side effects for an anti-inflammatory agent. Theophylline, a non-selective PDE inhibitor, inhibits both PDE III and PDE IV, resulting in both desirable anti-asthmatic effects and undesirable cardiovascular stimulation. With this well-known distinction between PDE isozymes, the opportunity for concomitant anti-inflammation and bronchodilation without many of the side effects associated with theophylline therapy is apparent. The increased incidence of morbidity and mortality due to asthma in many Western countries over the last decade has focused the clinical emphasis on the inflammatory nature of this disease and the benefit of inhaled steroids. Development of an agent that possesses both bronchodilatory and anti-inflammatory properties would be most advantageous.

It appears that selective PDE IV inhibitors should be more effective with fewer side effects than theophylline. Clinical support has been shown for this hypothesis.

Attempts have therefore been made to find new compounds having more selective and improved PDE IV inhibition.

OBJECTS AND SUMMARY OF THE INVENTION

It is accordingly a primary object of the present invention to provide new compounds which are effective PDE IV inhibitors.

It is another object of the present invention to provide new compounds which act as effective PDE IV inhibitors with lower PDE III inhibition.

It is a further object of the present invention to provide new compounds which have a superior PDE IV inhibitory effect as compared to rolipram or other known compounds.

It is a further object of the present invention to provide new compounds which have a substantially equal or superior PDE IV inhibitory effect as compared to known chemical compounds, and which exhibit surprisingly greater selectivity with regard to their inhibitory effects.

It is another object of the present invention to provide a method of treating a patient requiring PDE IV inhibition.

It is another object of the present invention to provide new compounds for treating disease states associated with abnormally high physiological levels of cytokines, including tumor necrosis factor.

It is another object of the present invention to provide a method of synthesizing the new compounds of this invention.

It is another object of the present invention to provide a method for treating a mammal suffering from a disease state selected from the group consisting of asthma, allergies, inflammation, depression, dementia, a disease caused by Human Immunodeficiency Virus and disease states associated with abnormally high physiological levels of cytokines.

With the above and other objects in view, the present invention mainly comprises compounds of the formula:

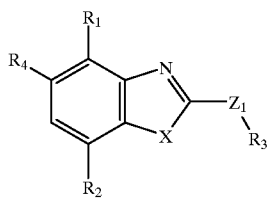

wherein:

X is O or S;

$R_1$ and $R_2$ are independently selected from hydrogen, halogen, hydroxy, nitro, $QZ_2$, $OQZ_2$, $OCOQZ_2$, $NHQZ_2$ or $NHCOQZ_2$ wherein:

Q is a bond, or a saturated or unsaturated straight-chain or branched alkylene, alkenylene or alkynylene group containing from 1 to 12 carbon atoms;

$Z_2$ is hydrogen, CH(OH)QH, OQH, $NO_2$, $N(QH)_2$, $CO_2QH$, $CON(QH)_2$, CON(OH)QH, OCOQH, $OCON(QH)_2$, OCON(OH)QH, $NHCON(QH)_2$, $N(OH)CON(QH)_2$, CH=NOCOQH, CH=NOCON $(QH)_2$, COQH, N(OH)COQH, aryl or a heteroaryl ring containing one or more of members of the group selected from nitrogen, oxygen and sulfur; said aryl or heteroaryl ring being unsubstituted or further substituted with one or more halogen atoms, alkyl groups, OH, OQH, $NO_2$, $NH_2$, $CO_2QH$, $CON(QH)_2$, OCOQH, and $OCON(QH)_2$;

$R_3$ is an unsubstituted aryl, heteroaryl or aryl/heteroaryl substituted with 1–3 members independently chosen from the group consisting of OH, O-alkyl, O(CO)alkyl, O-cycloalkyl, halogen, $NH_2$, $NO_2$, HO-alkyl, $R_5$ or $R_6$, wherein $R_5$ and $R_6$ are unsubstituted or substituted alkyls as defined in detail below;

$Z_1$ is a linkage selected from a bond, —$CH_2$—, —CH=CH—, $CH_2$—$CH_2$—, —CH($CH_3$)— and —C($CH_3$)$_2$—; except that $Z_1R_3$ is not 3,5-di-t-butyl-4-hydroxy-phenyl; and $R_4$ is hydrogen or a halogen.

The term "lower alkyl" is defined for purposes of the present invention as straight or branched chain radicals having from 1 to 3 carbon atoms.

In one preferred aspect of the invention, the compositions of Formula (I) are benzoxazole-based compounds having a PDE IV $IC_{50}$ of less than about 10 $\mu$M.

DETAILED DESCRIPTION

The compounds of the present invention, as demonstrated in the appended examples, are effective in the mediation or inhibition of PDE IV in humans and other mammals. Further, these compounds are selective PDE IV inhibitors which possess both bronchodilatory and anti-inflammatory properties substantially without undesirable cardiovascular stimulation caused by PDE III inhibition. Many of these compounds have a substantially equal or superior PDE IV inhibitory effect as compared to theophylline.

The present invention is further related to a method for the treatment of allergic and inflammatory disease which comprises administering to a mammal in need thereof an effective amount of the compounds of the present invention.

The present invention is also related to a method for the mediation or inhibition of the enzymatic or catalytic activity of PDE IV activity in mammals, particularly humans, which comprises administering an effective amount of the above-described compounds of the invention to a mammal in need of PDE IV inhibition.

The compounds of the present invention may find use in the treatment of other disease states in humans and other mammals, such as in the treatment of disease states associated with a physiologically detrimental excess of tumor necrosis factor (TNF). TNF activates monocytes, macrophages and T-lymphocytes. This activation has been implicated in the progression of Human Immunodeficiency Virus (HIV) infection and other disease states related to the production of TNF and other cytokines modulated by TNF. Accordingly, the compositions of the present invention can be administered in effective amounts to mammals suffering from asthma, allergies, inflammation, depression, dementia, atopic diseases, rhinitis and disease states associated with abnormally high physiological levels of cytokines, inflammatory cytokines and chemokines.

In certain preferred embodiments, the compounds of the present invention comprise the formula:

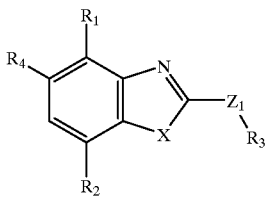

wherein:

X is O or S; and preferably O;

$R_1$ and $R_2$ are independently selected from hydrogen, halogen, hydroxy, nitro, $QZ_2$, $OQZ_2$, $OCOQZ_2$, $NHQZ_2$ or $NHCOQZ_2$ wherein:

Q is a bond, or a saturated or unsaturated straight-chain or branched alkylene, alkenylene or alkynylene group containing from 1 to 12 carbon atoms;

$Z_2$ is hydrogen, CH(OH)QH, OQH, $NO_2$, $N(QH)_2$, $CO_2QH$, $CON(QH)_2$, CON(OH)QH, OCOQH, $OCON(QH)_2$, OCON(OH)QH, $NHCON(QH)_2$, $N(OH)CON(QH)_2$, CH=NOCOQH, CH=NOCON$(QH)_2$, COQH, N(OH)COQH, aryl or a heteroaryl ring containing one or more of members of the group selected from nitrogen, oxygen and sulfur; said aryl or heteroaryl ring being unsubstituted or further substituted with one or more halogen atoms, alkyl groups, OH, OQH, $NO_2$, $NH_2$, $CO_2QH$, $CON(QH)_2$, OCOQH, and $OCON(QH)_2$;

$R_3$ is an unsubstituted aryl, heteroaryl or aryl/heteroaryl substituted with 1–3 members independently chosen from the group consisting of OH, O-alkyl, O(CO)alkyl, O-cycloalkyl, halogen, $NH_2$, $NO_2$, HO-alkyl, $R_5$ or $R_6$;

$Z_1$ is a linkage selected from a bond, $-CH_2-$, $-CH=CH-$, $-CH_2CH_2-$, $-CH(CH_3)-$ and $-C(CH_3)_2-$;

except that $Z_1R_3$ is not 3,5,-di-t-butyl-4-hydroxy-phenyl;

$R_4$ is hydrogen or a halogen;

$R_5$ a branched or straight chain alkyl group of 1–12 carbon atoms, preferably lower alkyl, most preferably methyl or ethyl; and $R_6$ is a cycloalkyl group of 1–12 carbon atoms, which may be substituted by one or more halogens, or an alkyl of 1–6 carbon atoms, preferably cyclopentyl which may be unsubstituted or substituted by $R_7$ as shown in the following structural formula:

wherein $R_7$ is hydrogen or a saturated or unsaturated straight-chain lower alkyl group containing from about 1 to about 6 carbon atoms, unsubstituted or substituted with one or more halogen atoms, hydroxyl groups, cyano groups, nitro groups, carboxyl groups, alkoxy groups, alkoxycarbonyl, carboxamido or substituted or unsubstituted amino groups.

In certain preferred embodiments, $R_4$ is a halogen, such as chlorine; one of $R_1$ or $R_2$ is hydrogen and X is oxygen or sulfur and preferably oxygen.

In further preferred embodiments, $Z_1$ is a linkage selected from the group consisting of a bond, $-CH_2-$, $-CH_2CH_2-$ and $-CH=CH-$.

In those aspects of the invention where one or both of $R_1$ and $R_2$ are $QZ_2$, Q is preferably an alkenylene or alkynylene group. Suitable alkenylene groups include, for example, $-CH=CH-$, and $-CH_2-CH=CH-$; suitable alkynyl groups include $-C\equiv C-$, and $-C\equiv C-CH_2-$.

Still further aspects of the invention include Q as an alkylene group. A non-limiting list of suitable groups include $-CH_2CH_2-$, $-CH_2CH_2CH_2-$.

Within this aspect of the invention, $Z_2$, where included, is preferably a 2-pyridine or 2-thiazole group.

$R_3$ can include an unsubstituted or substituted phenyl group such as phenyl, chlorophenyls, fluorophenyls, bichloro and bifluorophenyls, chloro-fluorophenyls and the like. Other aspects of the invention include $R_3$ groups such as 3,5-di-t-butyl-4-hydroxyphenyl; 3,5-di-t-butyl-4-acetoxyphenyl; 3,4-dimethoxyphenyl and 3-cyclopentyloxy-4-methoxyphenyl.

In another aspect of the invention, when X is O or S, preferably O and $Z_1$ is $-CH_2-$, $R_3$ is

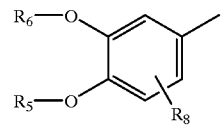

wherein $R_5$ is hydrogen or branched or straight chain alkyl group of 1–12 carbon atoms, preferably lower alkyl, most preferably methyl or ethyl, and $R_6$ is an alkyl group of 1–12 carbon atoms, which may be substituted by one or more halogens, or cycloalkyl of 3–6 carbon atoms, preferably cyclopentyl which may be substituted by $R_7$ as shown in the following structural formula:

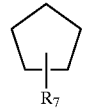

wherein $R_7$ is hydrogen or a saturated or unsaturated straight-chain lower alkyl group containing from about 1 to about 6 carbon atoms, unsubstituted or substituted with one or more halogen atoms, hydroxyl groups, cyano groups, nitro groups, carboxyl groups, alkoxy groups, alkoxycarbonyl, carboxamido or substituted or unsubstituted amino groups;

$R_8$ is hydrogen, lower alkyl or halogen.

In still further aspects of the inventions, $R_3$ includes moieties such as a chlorophenyl or a di-t-butyl-hydroxy benzyl.

Certain preferred compounds of the present invention include:

(I) 7-allyl-5-chloro-2-(3-cyclopentyloxy-4-methoxybenzyl)-benzoxazole;

(II) 5-chloro-2-(3,5-di-t-butyl-4-hydroxy-benzyl)-7-(2-(2-pyridyl)-ethynyl)-benzoxazole;

(III) 5-chloro-2-(3,5-di-t-butyl-4-hydroxy-benzyl)-7-(2-(2-thiazolyl)-ethynyl)-benzoxazole;

(IV) 7-bromo-5-chloro-2-(3-cyclopentyloxy-4-methoxybenzyl)-benzoxazole;

(V) 7-bromo-5-chloro-2-(3,4-dimethoxy-benzyl)-benzoxazole;

(VI) 2-(3-cyclopentyloxy-4-methoxy-benzyl)-7-nitrobenzoxazole;

(VII) 2-(3-cyclopentyloxy-4-methoxy-benzyl)-4-hydroxy-benzoxazole;

(VIII) 4-acetoxy-2-(3-cyclopentyloxy-4-methoxy-benzyl)benzoxazole;

(IX) 4-(5-chloro-2-(2-chlorophenyl)benzoxazol-7-yl) butan-2-one;

(X) 2-(3-Cyclopentyloxy-4-methoxy-benzyl)-4-(2-pyridylmethoxy) benzoxazole hydrochloride;

(XI) 2-(3-cyclopentyloxy-4-methoxy-benzyl)-7-(2-pyridinecarbonylamino)-benzoxazole; and (XII) 2-(3-cyclopentyloxy-4-methoxy-benzyl)-7-bromo-benzoxazole.

In other preferred aspects of the invention, the compounds in accordance with the present invention have a PDE IV $IC_{50}$ of less than about 10 $\mu$M and more preferably less than that of rolipram.

Description of the synthesis of a representative number of these molecules is set forth in the Examples. The synthesis of other molecules not specifically shown in the examples but within the scope of the invention are carried out using those techniques shown with modifications which are known to those of ordinary skill in the art.

The compounds of the present invention have been found to be highly effective PDE IV inhibitors, the inhibition of which is in fact significantly and surprisingly greater than that of theophylline which exhibits 50% inhibition of PDE IV at around 350 $\mu$M. In addition, the concentration which yields 50% inhibition of PDE IV ($IC_{50}$) for the compound prepared in Example 1 is 0.6 $\mu$M, whereas the $IC_{50}$ for rolipram when run in the same assay was 2.8 $\mu$M. Historically, the $IC_{50}$ for rolipram is considered to be 3.5 $\mu$M. In any case, it is apparent that this inventive compound is several times as effective as a PDE IV inhibitor as compared to rolipram (or theophylline).

While the PDE III inhibition of an Example 1 compound is only 22% at 10 $\mu$M, it is clear that the compound of the invention is highly selective as a PDE IV inhibitor.

Accordingly, the compounds of the present invention can be administered to anyone requiring PDE IV inhibition. Administration may be orally, topically, by suppository, inhalation or insufflation, or parenterally.

The present invention also encompasses, where appropriate, all pharmaceutically acceptable salts of the foregoing compounds. One skilled in the art will recognize that acid addition salts of the presently claimed compounds may be prepared by reaction of the compounds with the appropriate acid via a variety of known methods. Alternatively, alkali and alkaline earth metal salts are prepared by reaction of the compounds of the invention with the appropriate base via a variety of known methods.

Various oral dosage forms can be used, including such solid forms as tablets, gelcaps, capsules, caplets, granules, lozenges and bulk powders and liquid forms such as emulsions, solution and suspensions. The compounds of the present invention can be administered alone or can be combined with various pharmaceutically acceptable carriers and excipients known to those skilled in the art, including but not limited to diluents, suspending agents, solubilizers, binders, disintegrants, preservatives, coloring agents, lubricants and the like.

When the compounds of the present invention are incorporated into oral tablets, such tablets can be compressed, tablet triturates, enteric-coated, sugar-coated, film-coated, multiply compressed or multiply layered. Liquid oral dosage forms include aqueous and non-aqueous solutions, emulsions, suspensions, and solutions and/or suspensions reconstituted from non-effervescent granules, containing suitable solvents, preservatives, emulsifying agents, suspending agents, diluents, sweeteners, coloring agents, and flavoring agents. When the compounds of the present invention are to be injected parenterally, they may be, e.g., in the form of an isotonic sterile solution. Alternatively, when the compounds of the present invention are to be inhaled, they may be formulated into a dry aerosol or may be formulated into an aqueous or partially aqueous solution.

In addition, when the compounds of the present invention are incorporated into oral dosage forms, it is contemplated that such dosage forms may provide an immediate release of the compound in the gastrointestinal tract, or alternatively may provide a controlled and/or sustained release through the gastrointestinal tract. A wide variety of controlled and/or sustained release formulations ire well known to those skilled in the art, and are contemplated for use in connection with the formulations of the present invention. The controlled and/or sustained release may be provided by, e.g., a coating on the oral dosage form or by incorporating the compound(s) of the invention into a controlled and/or sustained release matrix.

Specific examples of pharmaceutically acceptable carriers and excipients that may be used for formulate oral dosage forms, are described in the *Handbook of Pharmaceutical Excipients*, American Pharmaceutical Association (1986), incorporated by reference herein. Techniques and compositions for making solid oral dosage forms are described in *Pharmaceutical Dosage Forms: Tablets* (Lieberman, Lachman and Schwartz, editors) 2nd edition, published by Marcel Dekker, Inc., incorporated by reference herein. Techniques and compositions for making tablets (compressed and molded), capsules (hard and soft gelatin) and pills are also described in *Remington's Pharmaceutical Sciences* (Arthur Osol, editor), 1553–1593 (1980), incorporated herein by reference. Techniques and composition for making liquid oral dosage forms are described in *Pharmaceutical Dosage Forms: Disperse Systems*, (Lieberman, Rieger and Banker, editors) published by Marcel Dekker, Inc., incorporated herein by reference.

When the compounds of the present invention are incorporated for parenteral administration by injection (e.g., continuous infusion or bolus injection), the formulation for parenteral administration may be in the form of suspensions, solutions, emulsions in oily or aqueous vehicles, and such formulations may further comprise pharmaceutically necessary additives such as stabilizing agents, suspending agents, dispersing agents, and the like. The compounds of the invention may also be in the form of a powder for reconstitution as an injectable formulation.

The dose of the compounds of the present invention is dependent upon the affliction to be treated, the severity of the symptoms, the route of administration, the frequency of the dosage interval, the presence of any deleterious side-effects, and the particular compound utilized, among other things.

The PDE IV inhibitory compounds of the present invention may be examined for their PDE IV inhibitory effects via the techniques set forth in the following examples, wherein the ability of the compounds to inhibit PDE IV isolated from bovine tracheal smooth muscle is set forth.

DESCRIPTION OF THE PREFERRED EMBODIMENTS

The following examples illustrate various aspects of the present invention, and are not to be construed to limit the claims in any manner whatsoever.

EXAMPLE 1

7-Allyl-5-chloro-2-(3-cyclopentyloxy-4-methoxybenzyl)-benzoxazole (a) 3-Cyclopentyloxy-4-methoxybenzaldehyde A mixture of 3-hydroxy-4-methoxybenzaldehyde (40 g, 0.26 mol), potassium carbonate (40 g, 0.29 mol) and cyclopentyl bromide (32 ml, 0.31 mol) in dimethylformamide (0.25 l) was heated under an argon atmosphere at 100° C. After 4 hours, additional cyclopentyl bromide (8.5 ml, 0.08 mol) was added and heating was continued for 4 hours. The mixture was allowed to cool and was filtered. The filtrate was concentrated under reduced pressure and the residue was partitioned between ether and aqueous sodium bicarbonate. The organic extract was washed with aqueous sodium carbonate and was dried (potassium carbonate). The solvent was removed in-vacuo and the residue was purified by flash chromatography, eluting with 2:1 hexanes/ether to provide a pale yellow oil (52 g, 89%)[may also be distilled at ~0.02 mm Hg].

Analysis Calc. for $C_{13}H_{16}O_3$; C 70.89, H 7.32; found: C 70.71, H 7.33

(b) 3-Cyclopentyloxy-4-methoxybenzyl Alcohol

A solution of 3-cyclopentyloxy-4-methoxybenzaldehyde (38 g 0.17 mol) in 40 ml of ethanol and sodium borohydride (1.63 g, 0.043 mol) was stirred for 2 hours at room temperature at which time the reaction was complete by TLC. The reaction was diluted with water and extracted with ethyl acetate. Evaporation of the ethyl acetate afforded 3-cyclopentyloxy-4-methoxybenzyl alcohol (37 g, 98%) suitable for the next step.

(c) 3-Cyclopentyloxy-4-methoxybenzyl Chloride

A solution of 3-cyclopentyloxy-4-methoxybenzyl alcohol (112 g, 0.50 mol) prepared as described above, in 1 liter of methylene chloride was stirred at room temperature with concentrated HCl (110 ml, 1.2 mol) for 3 hours at which time the reaction was done by TLC. The layers were separated and the methylene chloride solution was washed twice with water and evaporated under reduced pressure to give 3-cyclopentyloxy-4-methoxybenzyl chloride (119 g, 100%).

(d) 3-Cyclopentyloxy-4-methoxyphenylacetonitrile

A mixture of 3-cyclopentyloxy-4-methoxybenzyl chloride (119 g, 0.49 mol), 120 ml of methylene chloride, KCN (70.7 g, 1.09 mol), benzyltriethylammonium chloride (35 g, 0.015 mol) and water (120 ml) was stirred vigorously at room temperature for 48 hours when the reaction was complete by HPLC. The reaction mixture was diluted with methylene chloride and the layers were separated. The methylene chloride solution was extracted several times with water and evaporated to afford 3-cyclopentyloxy-4-methoxyphenylacetonitrile (109 g, 95%) of sufficient purity to be used in the subsequent transformation.

(e) 3-Cyclopentyloxy-4-methoxyphenylacetic Acid

A solution of 3-cyclopentyloxy-4-methoxyphenylacetonitrile (109 g, 0.43 mol) in 1330 ml of ethanol and NaOH (51 g, 1.3 mol) was heated under reflux for 48 hours. Ethanol (500 ml) was distilled from the reaction mixture and the residue was diluted with water and stirred with Norit A (11 g) for 2 min. The mixture was filtered through a pad of celite and acidified to pH 1 with concentrated HCl. Extraction of the mixture with ether afforded 120 g of crude 3-cyclopentyloxy-4-methoxyphenylacetic acid after evaporation of the ether at reduced pressure. The crude acid was dissolved in warm toluene (400 ml) and stirred for 1 hour with 10.5 g of Norit A. The charcoal was filtered and the toluene solution was diluted with heptane (400 ml). Filtration of the cooled solution afforded 72 g (67%) of pure 3-cyclopentyloxy-4-methoxyphenylacetic acid, mp 79–80° C.

(f) N-(3-cyclopentyloxy-4-methoxyphenylacetyl)-2-hydroxy-5-chloroaniline

To a stirred slurry of 1,1'-carbonyl diimidazole (7.1 g, 0.044 mol) in 40 ml of methylene chloride was added dropwise a solution of 3-cyclopentyloxy-4-methoxyphenylacetic acid (10 g, 0.040 mol) in 20 ml of methylene chloride. After stirring for 2 hours the resulting solution was added to a solution of 2-hydroxy-5-chloroaniline (6.0 g, 0.042 mol) in methylene chloride (75 ml). After stirring overnight, water was added and stirring was continued. The layers were separated and the methylene chloride layer was washed with 100 ml portions of water, dilute aqueous HCl, and water. Evaporation of the methylene chloride afforded the solid amide which was triturated with methanol (20 ml) and filtered to give 10.7 g (71%) of N-(3-cyclopentyloxy-4-methoxyphenylacetyl)-2-hydroxy-5-chloroaniline, mp 151–152° C.

(g) N-(3-cyclopentyloxy-4-methoxyphenylacetyl)-2-allyloxy-5-chloroaniline

To a stirred solution of N-(3-cyclopentyloxy-4-methoxyphenylacetyl)-2-hydroxy-5-chloroaniline (78 g, 0.21 mol) in ethanol (600 ml) and 1 N NaOH in methanol (213 ml) was added allyl chloride (23.3 g, 0.31 mol). The mixture was heated under reflux for 8 hours, after which it was diluted with water and extracted twice with ethyl acetate. Evaporation of the ethyl acetate and crystallization of the residue from methanol gave 56.4 g (65%) of the title compound, mp 75–76.5° C.

(h) 7-allyl-5-chloro-2-(3-cyclopentyloxy-4-methoxybenzyl)-benzoxazole

A solution of N-(3-cyclopentyloxy-4-methoxyphenylacetyl)-2-allyloxy-5-chloroaniline (38.1 g, 0.092 mol) in 200 ml of diphenyl ether was heated under nitrogen at 180° for 8 hours. Protracted heating resulted in reduced yields. The reaction mixture was diluted with 500 ml of petroleum ether, applied to a column packed with 500 g of flash chromatography silica gel and eluted with petroleum ether followed by methylene chloride. Fractions of 800 ml were collected. The material from fractions 9–14 weighed 30 g (80% of theoretical). This material was recrystallized from hexane to give 19 g (52%) of the title compound, mp 43–44° C., which was greater than 98.3% pure by HPLC.

HPLC conditions

Reactions were monitored by HPLC using an Alltech Alltima column, C 18, 5 microns, 250×4.6 mm. Solvent: methanol/water (85:15), 1 ml/min at 254 nm. Retention time: 21 min.

EXAMPLE 2

5-Chloro-2-(3,5-di-t-butyl-4-hydroxy-benzyl)-7(2-(2-pyridyl)-ethynyl)-benzoxazole (a) 2-Bromo-4-chloro-6-nitro-phenol A solution of 2-bromo-4-chloro-phenol (99.24 g, 480 mmol) in acetic acid (110 ml) and acetic anhydride (125 ml)

was cooled to −10° C. Within 1 hour a solution containing 100% nitric acid (33 ml) and acetic acid (40 ml) was added between −10° and −5° C., with stirring. The mixture was stirred for an additional 1.5 hours at 0–5° C., then the suspension poured onto 300 g of ice in 700 ml of water and stirred for a further 0.5 hour. The solid was collected, washed, and dried to give 97.12 g (80.1%) of the title compound (mp 121–2° C.).

(b) 6-Amino-2-bromo-4-chloro-phenol

A solution of 2-bromo-4-chloro-6-nitro-phenol (16.27 g, 64.4mmol) in ethyl acetate (160 ml) was hydrogenated, at room temperature, with Raney-nickel (6 g). After hydrogen uptake (approx. 4.8 l) was complete, the nickel was removed by filtration and the filtrate evaporated in-vacuo to give 14.19 g (99.0%) of the title compound which was suitable for the next step.

(c) N,O-di-(3,5-di-t-butyl-4-hydroxy-phenylacetyl)-6-amino-2-bromo-4-chloro-phenol Water (173 ml) and sodium carbonate (33.24 g, 310 mmol) were added to a stirred ethereal solution (123 ml) of 6-amino-2-bromo-4-chloro-phenol (17.45 g, 78.4 mmol). After 15 minutes 3,5-di-t-butyl-4-hydroxy-phenylacetyl chloride (47.60 g, 93.1%, 156.8 mmol) (prepared with thionyl chloride from the corresponding acid), was added at −5° to 0° C. and stirring continued for a further 1.5 hours without cooling. The aqueous phase was adjusted to pH 8 and the layers separated. The organics were washed with 1 N HCl (100 ml) and saturated aqueous sodium bicarbonate solution (100 ml), dried ($Na_2SO_4$) and evaporated in-vacuo to give 58.1 g (103.6%) of the title compound which was suitable for the next step.

(d) 2-Bromo-4-chloro-6-(3,5-di-t-butyl-4-hydroxy-phenylacetyl-amino)-phenol

A solution of N,O-Di-(3,5-di-t-butyl-4-hydroxy-phenylacetyl)-6-amino-2-bromo-4-chloro-phenol (58.1 g, 89.8 mmol) in methanol (400 ml) and potassium carbonate (24.78 g, 180 mmol) was stirred at room temperature for 10 minutes. The methanol was removed in-vacuo, the residue treated with 2 N HCl (180 ml, 360 mmol), and extracted with ethyl acetate (300 ml). The organics were dried ($Na_2SO_4$), evaporated in-vacuo, and the residue suspended in petroleum ether. The precipitate was collected to give 37.44 g (88.9%) of the title compound which was suitable for the next step.

(e) 7-Bromo-5-chloro-2-(3,5-di-t-butyl-4-hydroxy-benzyl)-benzoxazole

A solution of 2-bromo-4-chloro-6-(3,5-di-t-butyl-4-hydroxy-phenylacetyl-amino)-phenol (35.67 g, 76.1 mmol) and phosphorus oxychloride (41.8 ml, 457 mmol) in toluene was heated under reflux for 1 hour. Volatiles were removed in-vacuo and residual amounts of phosphorus oxychloride removed by azeotropic distillation with toluene (2×50 ml). The residue was taken up in acetone (50 ml) and ether (100 ml), and treated with water (100 ml) and saturated aqueous sodium bicarbonate solution (100 ml). The organic solvents were removed in-vacuo and the precipitate collected to give 33.36 g (93.6%) of crude benzoxazole. The crude benzoxazole was dissolved in dichloromethane (100 ml), filtered, and the filtrate diluted with methanol (100 ml). The dichloromethane was removed by distillation and the resulting crystals collected, washed, and dried in-vacuo to give 28.86 g (80.9%) of the title compound (mp 133–6° C.).

(f) 5-Chloro-2-(3,5-di-t-butyl-4-hydroxy-benzyl)-7-ethynyl-benzoxazole

A suspension of 7-bromo-5-chloro-2-(3,5-di-t-butyl-4-hydroxy-benzyl)-benzoxazole (13.50 g, 30 mmol), trimethylsilylacetylene (4.41 g, 6.36 ml, 45 mmol), bis(triphenylphosphine) palladium (II) dichloride (105 mg, 150 µmol) and copper (I) iodide (5.75 mg, 30 µmol) in triethylamine (60 ml) was heated at 90° C., under argon, for 3 hours. The mixture was cooled to room temperature, diluted with water (375 ml) and the excess triethylamine removed in-vacuo. The solid was removed by filtration and the filtrate evaporated in-vacuo to give 14.00 g (100%) of crude trimethylsilylacetylene derivative. A suspension of the crude trimethylsilylacetylene derivative (14 g) in methanol (140 ml) and potassium carbonate (6.20 g, 45 mmol) was stirred at room temperature, under nitrogen, for 10 minutes; 2 N HCl (45 ml, 90 mmol) was added slowly and the formed suspension evaporated in-vacuo. The residue was taken up in dichloromethane (200 ml), the salt removed by filtration and the filtrate evaporated in-vacuo to give 12.21 g (102.8%) of crude 5-chloro-2-(3,5-di-t-butyl-4-hydroxy-benzyl)-7-ethynyl-benzoxazole. The crude ethynyl-benzoxazole was dissolved in dichloromethane (40 ml) and filtered through 60 g of silica gel. The product was recrystallized from methanol to give 8.10 g (68.2%) of the title compound (mp 152–5° C.). From the filtrate a second crop of 1.31 g (11.0%) was also obtained.

Elemental analysis for $C_{24}H_{26}ClNO_2$;

| | | | | |
|---|---|---|---|---|
| Calc. | C 72.81 | H 6.62 | N 3.54 | O 8.10 |
| Found | C 72.26 | H 6.60 | N 3.72 | O 8.07 |

(g) 5-Chloro-2-(3,5-di-t-butyl-4-hydroxy-benzyl)-7-(2-(2-pyridyl)-ethynyl)-benzoxazole A suspension of 5-chloro-2-(3,5-di-t-butyl-4-hydroxy-benzyl)-7-ethynyl-benzoxazole (2.38 g, 6.0 mmol), 2-bromo-pyridine (0.66 ml, 98%, 6.6 mmol), bis(triphenylphosphine)palladium(II) dichloride (21.1 mg, 30 µmol) and copper (I) iodide (1.2 mg, 6 µmol) in triethylamine (12 ml) was heated at 90° C., under argon, for 1.5 hours. The triethylamine was removed in-vacuo and the residue dissolved in ether (100 ml). The organics were washed with water (50 ml), 1 N HCl (100 ml) and saturated aqueous sodium hydrogen carbonate (100 ml), dried ($Na_2SO_4$) and evaporated in-vacuo to give 2.96 g (104.2%) of crude pyridylethynylbenzoxazole. The crude benzoxazole was purified by column chromatography ($SiO_2$; dichloromethane), and the product crystallized from methanol and suspended in hot water. The resulting crystals were collected, washed, and dried to give 1.49 g (52.5%) of the title compound (mp 138–9° C.).

Elemental analysis for $C_{29}H_{29}ClN_2O_2$;

| | | | | |
|---|---|---|---|---|
| Calc. | C 73.64 | H 6.18 | N 5.92 | O 6.76 |
| Found | C 73.62 | H 5.97 | N 5.91 | O 6.93 |

EXAMPLE 3

5-Chloro-2-(3,5-di-t-butyl-4-hydroxy-benzyl)-7-(2-(2-thiazolyl)-ethynyl)-benzoxazole A suspension of 5-chloro-2-(3,5-di-t-butyl-4-hydroxy-benzyl)-7-ethynyl-benzoxazole (2.38 g, 6.0 mmol), 2-bromothiazole (1.13 ml, 95%, 12 mmol), bistriphenylphosphine)palladium(II) dichloride (21.1 mg, 30 μmol), and copper (I) iodide (1.2 mg, 6 μmol) in triethylamine (12 ml) was heated at 90° C., under argon, for 3 hours. The triethylamine was removed in-vacuo and the residue dissolved in ether (70 ml) and water (30 ml). The organics were washed with 1 N HCl (30 ml) and saturated sodium hydrogen carbonate (30 ml), dried ($Na_2SO_4$) and evaporated in-vacuo to give 2.86 g (100%) of crude thiazolylethynylbenzoxazole, which was purified by flash chromatography ($SiO_2$; dichloromethane). The product was crystallized and recrystallized from methanol to give 1.43 g (50.4%) of the title compound (mp 137–41° C.).

Elemental analysis for $C_{27}H_{27}ClN_2O_2S$;

| Calc. | C 67.70 | H 5.68 | N 5.85 | O 6.68 |
| --- | --- | --- | --- | --- |
| Found | C 67.62 | H 5.40 | N 5.65 | O 6.76 |

EXAMPLE 4

7-Bromo-5-chloro-2-(3-cyclopentyloxy-4-methoxybenzyl)-benzoxazole (a) N,O-di(3-cyclopentyloxy-4-methoxy-phenylacetyl)-6-amino-2-bromo-4-chloro-phenol A solution of 48.7 g of 3-cyclopentyloxy-4-methoxy-phenylacetyl chloride in 240 ml of ether was added, at 0–5° C. within 10 min, to a two phase solution of 19.6 g of 2-amino-3-bromo-5-chlorophenol (freshly prepared) in 300 ml of ether and 360 ml water. After 1 hour at 15° C. the ether was removed in vacuo and the brownish solid collected, washed with water and dried to give 58.95 g of crude amide ester.

(b) 2-Bromo-4-chloro-6-(3-cyclopentyloxy-4-methoxy-phenyl-acetylamino)-phenol

A suspension of 58.7 g of N,O-di(3-cyclopentyloxy-4-methoxy-phenylacetyl)-6-amino-2-bromo-4-chloro-phenol in 200 ml of isopropanol was added at 10° C. to a two phase solution of 9.59 g of potassium hydroxide in 6.15 ml of water and 490 ml of isopropanol. After 15 minutes, practically all the solid was dissolved. After 45 minutes, 200 ml of water was added and the suspension brought to pH 7 with 85 ml of 1 N HCl. The isopropanol was removed in vacuo and 50 ml of saturated sodium bicarbonate solution added to bring the pH to about 8. After 45 min the solid was collected, washed with bicarbonate and water until neutral, and dried to give 43.2 g of crude amide; the filtrate was acidified and 16.87 g of 3-cyclopentyloxy-4-methoxyphenylacetic acid recovered.

The crude amide was suspended in 200 ml of dichloromethane and the solid collected to give 31.30 g of title compound.

(c) 7-Bromo-5-chloro-2-(3-cyclopentyloxy-4-methoxy-benzyl)-benzoxazole

A suspension of 32.9 g (72.4 mmol) of 2-bromo-4-chloro-6-(3-cyclopentyloxy-4-methoxy-phenyl-acetylamino)-phenol in 400 ml of toluene and 39.7 ml (434 mmol) of phosphorus oxychloride was refluxed for 1.5 hours. Some solid material was filtered off and the filtrate evaporated to dryness in vacuo. The honey-like residue was suspended in 200 ml of sodium bicarbonate solution for 1 hours. The solid was collected, washed and dried at 25° C. to give 22.53 g (71.2%) of crude benzoxazole.

The crude material was dissolved in 100 ml of dichloromethane and filtered through 60 g of silica gel. Crystallization from methanol afforded 19.46 g (61.9%) of pure benzoxazole (mp 90–1° C.).

EXAMPLE 5

7-Bromo-5-chloro-2-(3,4-dimethoxybenzyl) benzoxazole

By using a similar procedure to Example 4 employing 3,4-dimethoxy-phenylacetyl chloride and 2-amino-3-bromo-5-chlorophenol the title compound was obtained (mp 123–124° C.).

EXAMPLE 6

2-(3-Cyclopentyloxy-4-methoxybenzyl)-7-nitro-benzoxazole (a) 2-amino-6-nitrophenol A suspension of 2,6-dinitrophenol (5 g), ammonia (3 ml) and ammonium chloride (14.30 g) in water (30 ml) was heated to 70° C. A solution of sodium sulphide nonahydrate (24.19 g) in water (23 ml) was added and the resulting mixture stirred at 70° C. for 2 hours. The reaction was cooled to room temperature, acidified (pH 3.2) with 2N HCl, and the brown precipitate separated by filtration. The filtrate was extracted with chloroform (6×75 ml), the organic extracts combined with the precipitate, and evaporated in-vacuo to yield a dark brown solid. The solid was purified by flash chromatography (SiO2; dichloromethane) to yield the title compound (2.86 g, 68%) as a brown solid.

$δ_H$(250 MHz; $d_6$ DMSO), 6.75 (1H,td,ArH), 6.90 (2H,bs, ArNH$_2$), 6.92 (1H,m,ArH), 7.14 (1H,m,ArH).

(b) N-(2-hydroxy-3-nitrophenyl)-3-cyclopentyloxy-4-methoxy-phenylacetamide

A suspension of 3-cyclopentyloxy-4-methoxyphenylacetic acid (1.00 g) and 1,1'-carbonyl diimidazole (821 mg) in dichloromethane (5 ml) was stirred at room temperature, under argon, for 2 hours. The resulting solution was added to a stirred solution of 2-amino-6-nitrophenol (723 mg) in dichloromethane (10 ml) and the mixture stirred at room temperature, under argon, overnight. The reaction mixture was diluted with water (100 ml) and extracted with dichloromethane (3×50 ml). The combined organic extracts were washed with water (100 ml), 1 N HCl (50 ml) and brine (50 ml), dried over $CaSO_4$ and evaporated in-vacuo to yield the title compound (1.05 g, 68%) as an orange solid.

$δ_H$(250 MHz; $d_6$ DMSO), 1.58–1.97 (8H,m,4×CH$_2$), 3.73 (2H,s,CH$_2$), 3.87 (3H,s,OMe), 4.79 (1H,m,CH), 6.78–6.93 (3H,m,ArH), 6.98 (1H,t,ArH), 7.78 (1H,dd,ArH), 7.95 (1H, bs,CONH), 8.71 (1H,dd,ArH), 10.5 (1H,bs,ArOH).

(c) 2-(3-cyclopentyloxy-4-methoxybenzyl)-7-nitrobenzoxazole

A solution of N-(2-hydroxy-3-nitrophenyl)-3-cyclopentyloxy-4-methoxy-phenylacetamide (2.0 g) and pyridinium p-toluene-sulphonate (500 mg) in xylene (140 ml) was heated at reflux, under nitrogen, overnight. The reaction mixture was cooled to room temperature, diluted with water (100 ml) and extracted with dichloro-methane (3×75 ml). The combined organic extracts were washed with water (3×100 ml), brine (100 ml), dried (CaSO$_4$) and evaporated in-vacuo to yield an orange oil. The oil was purified by flash chromatography (SiO$_2$; dichloromethane; ethanol; ammonia (50:1:0.1)) to yield the title compound (1.107 g, 58%) as an orange solid (mp 95–98.5° C.).

δ$_H$(250 MHz;d$_6$ DMSO) 1.45–1.95 (8H,m,4×CH$_2$), 3.70 (3H,s,OMe), 4.36 (2H,s,CH$_2$), 4.74 (1H,m,CH), 6.89 (2H, bs,ArH), 7.02 (1H,bs,ArH), 7.56 (1H,t,ArH), 8.15 (1H,dd, ArH), 8.17 (1H,dd,ArH). m/z 368 (M$^+$), 338 (M-NO), 300 (M-C$_5$H$_8$), 285, 270, 253, 149, 137, 123, 100.

EXAMPLE 7

2-(3-Cyclopentyloxy-4-methoxybenzyl)-4-hydroxy-benzoxazole (a) 2-Aminoresorcinol A suspension of 2-nitroresorcinol (4.995 g) and platinum (IV) oxide (356 mg) in ethanol (90 ml) was hydrogenated, at room temperature, at 100 p.s.i. for 4 hours. The reaction mixture was filtered through celite, the filter cake washed with methanol (50 ml), and the combined filtrate evaporated in-vacuo to yield a brown solid. The solid was suspended in dichloromethane (100 ml) and evaporated to dryness to yield the title compound (3.83 g, 95%) as a brown solid.

δ$_H$(250 MHz; d$_6$ DMSO) 3.85 (2H,br s,NH$_2$), 6.20 (3H, m,ArH), 8.85 (2H,br s,ArOH).

(b) N-(2,6-dihydroxyphenyl)-3-cyclopentyloxy-4-methoxyphenylacetamide

A suspension of 3-cyclopentyloxy-4-methoxyphenylacetic acid (2.49 g) and 1,1'-carbonyl diimidazole (2.31 g) in dichloromethane (10 ml) was stirred at room temperature, under argon, for 2 hours. The resulting solution was added to a stirred suspension of 2-aminoresorcinol (1.62 g) in dichloromethane (15 ml) and the mixture stirred at room temperature, under argon, overnight. The reaction mixture was diluted with water (100 ml) and extracted with dichloromethane (3×50 ml). The combined organic extracts were washed with water (100 ml), 1 N HCl (100 ml) and brine (100 ml), dried over CaSO$_4$ and evaporated in-vacuo to yield the title compound (2.122 g, 60%) as a beige solid.

δ$_H$(250 MHz; d$_6$ DMSO) 1.53–1.95 (8H,m,4×CH$_2$), 3.65 (2H,s,CH$_2$), 3.70 (3H,s,OMe), 4.75 (1H,m,CH), 6.3 (1H,s, ArH), 6.35 (1H,s,ArH), 6.90 (4H,m,ArH), 9.40 (2H,s, ArOH), 9.6 (1H,s,CONH).

(c) 2-(3-Cyclopentyloxy-4-methoxybenzyl)-4-hydroxybenzoxazole

A solution of N-(2,6-dihydroxyphenyl)-3-cyclopentyloxy-4-methoxyphenyl-acetamide (2.10 g) and pyridinium p-toluene-sulphonate (532 mg) in xylene (100 ml) was refluxed, under nitrogen, overnight. The reaction mixture was cooled to room temperature, diluted with water (100 ml), and extracted with dichloromethane (3×75 ml). The combined organic extracts were washed with water (3×100 ml), brine (100 ml), dried (CaSO$_4$) and evaporated in-vacuo to yield a pale brown solid. The solid was purified by flash chromatography (SiO$_2$; dichloromethane;methanol (50:1)) to yield the title compound (1.027 g, 51%) as a white solid (mp 172–181° C.).

δ$_H$(250 MHz; d$_6$ DMSO) 1.53–1.85 (8H,m,4×CH$_2$), 3.70 (3H,s,OMe), 4.18 (2H,s,CH$_2$), 4.72 (1H,m,CH), 6.69 (1H, dd,ArH), 6.82 (1H,dd,ArH), 6.89 (1H,d,ArH), 6.93 (1H,d, ArH), 7.02 (1H,dd,ArH), 7.11 (1H,t,ArH), 10.22 (1H,s, ArOH). m,z 339 (M$^+$), 271 (M-C$_5$H$_8$), 256,242,228,199, 149,137,123,94.

EXAMPLE 8

4-Acetoxy-2-(3-cyclopentyloxy-4-methoxybenzyl)-benzoxazole (a) 4-Acetoxy-2-(3-cyclopentyloxy-4-methoxybenzyl)-benzoxazole A solution of 2-(3-cyclopentyloxy-4-methoxybenzyl)-4-hydroxybenzoxazole (200 mg) and acetyl chloride (84 µl) in pyridine (6 ml) was stirred at room temperature, under nitrogen, for 3 hours. The reaction mixture was diluted with methanol (20 ml) and evaporated in-vacuo to yield a yellow solid. The solid was purified by flash chromatography (SiO$_2$; dichloromethane; methanol (50:1)) and crystallized from ether/petroleum ether to yield the title compound (119 mg, 53%) as a white crystalline solid (mp 65–67° C.).

δ$_H$(250 MHz; d$_6$ DMSO) 1.45–1.92 (8H,m,4×CH$_2$), 2.35 (3H,s,MeC(O)), 3.70 (3H,s,OMe), 4.24 (2H,s,CH$_2$), 4.73 (1H,m,CH), 6.82 (1H,dd,ArH), 6.89 (1H,d,ArH), 6.95 (1H, d,ArH), 7.12 (1H,dd,ArH), 7.36 (1H,t,ArH), 7.58 (1H,dd, ArH). Rf(SiO$_2$;dichloromethane;methanol (50:1)) 0.63.

EXAMPLE 9

4-(5-Chloro-2-(2-chlorophenyl)benzoxazol-7-yl)butan-2-one (a) 5-Chloro-2-(2-chlorophenyl)-7-(3-hydroxy-1-butynyl)-benzoxazole 15.98 g (46.6 mmol) of 7-bromo-5-chloro-2-(2-chlorophenyl)-benzoxazole and 5 5.48 ml (69.9 mmol) of (±)-3-butyn-2-ol were heated for 6 h at 90–5° C. in 47 ml of toluene with 47 ml of triethylamine, 163.5 mg (233 µmol) of bis-triphenylphosphine-palladium(II)-dichloride and 8.9 mg (46.6 23 µmol) of copper(I) iodide. The reaction was filtered and the solid washed with toluene. The filtrate was evaporated in vacuo to dryness, the residue taken up in 150 ml of dichloromethane, extracted twice with 50 ml of 1 N HCl, dried with sodium sulfate, and filtered through 120 g of silica gel in a column. The title compound (11.11 g) was recovered as an off-white solid. A recrystallized sample from di-isopropyl ether had mp 129–31° C.

(b) 5-Chloro-2-(2-chlorophenyl)-7-(3-hydroxybutyl)-benzoxazole 11.10 g (33.4 mmol) of 5-chloro-2-(2-chlorophenyl)-7-(3-hydroxy-1-butynyl)-benzoxazole was hydrogenated in 220 ml of ethyl acetate with 3.7 g of neutral Raney-nickel as catalyst. After 2.5 hours, H$_2$ uptake had ceased and the nickel was filtered off. The solvent was removed in vacuo and the residue crystallized from di-isopropyl ether at 0° C. to give 8.33 g (74.2%) of title compound, mp 85–7° C. A second crop of 0.47 g (4.2%) was recovered.

(c) 4-(5-Chloro-2-(2-chlorophenyl)benzoxazol-7-yl)butan-2-one 7.54 ml of Kiliani solution (30.2 mmol of 0) was added over 6 minutes to a solution of 8.80 g (26.2 mmol) of 5-chloro-2-(2-chlorophenyl)-7-(3-hydroxybutyl)-benzoxazole in 90 ml of acetone at −5° to 0° C. After 2.5 hours, 5 ml of methanol and 50 ml of water was added. The acetone was removed in vacuo, the solid suspended, collected, washed with 0.1 N sulfuric acid until colorless and water and dried to give 8.68 g of crude product, which was dissolved in 35 ml of dichloromethane and filtered through 260 g of silica gel. A first fraction of 100 mg was discarded then 5.94 g were recovered and crystallized from di-isopropyl ether to give 5.76 g (65.8%) of title compound, mp 109–10° C.

Elemental analysis for $C_{17}H_{13}Cl_2NO_2$;

| Calc: | C 61.09 | H 3.92 | N 4.19 | O 9.57 |
| Found: | C 61.21 | H 4.24 | N 4.16 | O 9.86. |

EXAMPLE 10

2-((3-Cyclopentyloxy-4-methoxy)benzyl)-4-(2-pyridylmethoxy)-benzoxazole Hydrochloride 2-(3-cyclopentyloxy-4-methoxybenzyl)-4-hydroxybenzoxazole (0.99 g, 2.91 mmol) was suspended in acetonitrile (40 ml) containing potassium carbonate (3.12 g, 22.5 mmol), 2-pyridylmethyl chloride (0.62 g, 3.78 mmol) and sodium iodide (41 mg). The resulting mixture was heated at reflux with stirring overnight. The reaction mixture was poured onto water (150 ml) and extracted with ethyl acetate (3×100 ml). The combined organic extracts were washed with water (150 ml) and brine (100 ml), dried ($CaSO_4$) and evaporated in-vacuo to afford a brown oil. The residue was purified by flash chromatography ($SiO_2$; dichloromethane (50:1)) to afford the free base of title compound as a colorless oil (0.772 g, 62%). The product was dissolved in ether (50 ml) and to the resultant solution was added a solution of hydrochloric acid (1 M in ether). The resultant colorless precipitate was collected by filtration, washed with ether (50 ml) and dried in vacuo over $P_2O_5$ at room temperature to afford the title compound (0.747 g, 55%) as a colorless powder (mp 121–125° C.).

$\delta_H$(250 MHz; $d_6$ DMSO) 1.52–1.82 (8H,m,4×$CH_2$), 3.70 (3H,s,OMe), 4.21 (2H,s,$CH_2$), 4.73 (1H,m,CH), 5.56 (2H, s,$CH_2$), 6.82 (1H,dd, ArH), 6.89 (1H,d,ArH), 6.95 (1H,d, ArH), 7.00 (1H,m,ArH), 7.23–7.29 (2H,m,ArH), 7.67 (1H, m,ArH), 7.83 (1H,d,ArH), 8.19 (1H,dt,ArH), 8.75 (1H,d, ArH).

EXAMPLE 11

Protocols for PDE IV, PDE III, and PDE V inhibition activity are set forth below:

Type III Phosphodiesterase Enzyme Isolation Protocol

The Type III PDE is isolated from human platelets using a procedure similar to that previously described by Washer, R. E. et al., Biochem. Pharmacol., 35:787, 1986. Briefly, 1–2 units of platelets are suspended in an equal volume of buffer (20 mM Tris-HCl, pH 7.5, containing 2 mM magnesium acetate, 1 mM dithiothreitol, and 5 mM $Na_2EDTA$). The proteinase inhibitor phenylmethyl-sulfonyl fluoride (PMSF) is also included in this buffer at a final concentration of 200 $\mu$M. The suspension is homogenized using a polytron and the homogenate centrifuged at 100,000×g for 60 minutes. This and all subsequent procedures are performed at 0–4° C. The supernatant is then filtered through four layers of gauze and applied to a DEAE-Trisacryl M column, previously equilibrated with buffer B (20 mM Tris-HCl, pH 7.5, containing 1 mM magnesium acetate, 1 mM dithiothreitol and 200 $\mu$M PMSF). After application of the sample, the column is washed with several bed volumes of buffer B, after which the different forms of PDE are eluted from the column using two successive linear NaCl gradients (0.05–0.15 M, 300 ml total; 0.15–0.40 M, 200 ml total). Five ml fractions are collected and assayed for cyclic AMP and cyclic GMP PDE activity. Fractions containing PDE III activity are pooled and dialyzed overnight against 4 L of buffer B. The dialyzed PDE III is then concentrated to 10% of the original volume, diluted to 50% with ethylene glycol monoethyl ether and stored at −20° C. PDE III can typically be retained for up to four weeks with little or no loss of activity.

Measuring Type III PDE Activity

Enzyme activity is assessed by measuring the hydrolysis of [$^3$H]-cyclic AMP, as described by Thompson, W. J. et al., Adv. Cyclic Nucleotide Res. 10:69, 1979. The cyclic AMP concentration used in this assay is 0.2 $\mu$M, which approximates to the $K_m$ value. Protein concentration is adjusted to ensure that no more than 15% of the available substrate is hydrolyzed during the incubation period.

All test compounds are dissolved in dimethyl sulfoxide (final concentration of 2.5%). This concentration of dimethyl sulfoxide inhibits enzyme activity by approximately 10%.

Type IV Phosphodiesterase Enzyme Isolation Protocol

The Type IV PDE is isolated from bovine tracheal smooth muscle using a procedure similar to that previously described by Silver, P. J. et al., Eur. J. Pharmacol. 150:85, 1988.(1). Briefly, smooth muscle from bovine trachea is minced and homogenized using a polytron in 10 volumes of an extraction buffer containing 10 mM Tris-acetate (pH 7.5), 2 mM magnesium chloride, 1 mM dithiothreitol and 2,000 units/ml of aprotinin. This and all subsequent procedures are performed at 0–4° C. The homogenate is sonicated and then centrifuged at 48,000×g for 30 minutes. The resulting supernatant is applied to a DEAE Trisacryl M column previously equilibrated with sodium acetate and dithiothreitol. After applications of the sample, the column is washed with sodium acetate/dithiothreitol, after whlich the different forms of PDE are eluted from the column using a linear Tris-HCl/NaCl gradient. Fractions containing Type IV PDE are collected, dialyzed and concentrated to 14% of the original volume. The concentrated fractions are diluted to 50% with ethylene glycol and stored at −20° C.

Measuring Type IV PDE Activity

Enzyme activity is assessed by measuring the hydrolysis of [$^3$H]-cyclic AMP, as described by Thompson, W. J. et al., Adv. Cyclic Nucleotide Res. 10:69, 1979. The cyclic AMP concentration used in this assay is 0.2 $\mu$M, which approximates the $K_m$ value. Protein concentration is adjusted to ensure that no more than 15% of the available substrate is hydrolyzed during the incubation period.

All test compounds are dissolved in dimethyl sulfoxide (final concentration of 2.5%). This concentration of dimethyl sulfoxide inhibits enzyme activity by approximately 10%.

EXAMPLE 12

Following the above procedures, the PDE III, PDE IV inhibition for the compounds of Examples 1–10, aid rolipram are tested and compared. The results are shown in Table I below:

TABLE I

| Example | IC$_{50}$($\mu$M) | |
|---|---|---|
| | PDE III | PDE IV |
| 1 | >300 | 0.08 |
| 2 | >300 | 0.01 |
| 3 | >300 | 0.01 |
| 4 | 7.4 | 25.10 |
| 5 | 10 | 2.20 |
| 6 | 0.6 | 1.60 |
| 7 | 124.5 | 0.50 |
| 8 | 158.5 | 0.75 |
| 9 | >300 | 0.60 |
| 10 | >300 | 0.53 |
| Rolipram | 620 | 3.70 |

EXAMPLE 13

7-Amino-2-((3-Cyclopentyloxy-4-methoxy)benzyl)-benzoxazole Hydrochloride (a) 7-Amino-2-((3-cyclopentyloxy-4-methoxy)benzyl)-benzoxazole 2-((3-Cyclopentyloxy-4-methoxy)benzyl)-7-nitrobenzoxazole obtained using the procedure of Example 6, (0.537 g, 0.0015 mmol), was suspended in ethanol (7 ml). Raney nickel (0.612 g of a slurry in water) was added and the mixture was heated to 50° C. with stirring. A mixture of hydrazine hydrate (5 ml) and ethanol (2 ml) was added dropwise. On completion of the addition the reaction mixture was stirred at room temperature. After 17 hours, the reaction mixture was filtered through celite and the residue was washed with ethanol (20 ml). The filtrate was evaporated in vacuo and the evaporation residue was purified by flash chromatography (SiO$_2$, chloroform/ethyl acetate 20:1 v/v) and afforded the title compound as a pale yellow gum (0.309 g, 0.00091 mol, 63%).

$\delta_H$(250 MHz; d$_6$ DMSO) 1.53–1.85 (8H, m, 4×—CH$_2$—), 3.70 (3H, s, —OCH$_3$), 4.17 (2H, s, Ar—CH$_2$—), 4.73 (1H, m, —CH—), 5.44 (2H, bs, —NH$_2$), 6.56 (1H, d, J=7.7 Hz, Ar—H), 6.79–7.01 (5H, m, Ar—H).

(b) 7-Amino-2-((3-Cyclopentyloxy-4-methoxy)benzyl)-benzoxazole hydrochloride 7-(Amino-2-(3-cyclopentyloxy-4-methoxy)benzyl)-benzoxazole (0.521 g, 0.0016 mol) was dissolved in ether (50 ml). Hydrogen chloride (3 ml of a 1 M solution) was added and the resulting white precipitate was collected by filtration, washed with ether (30 ml) and set aside in vacuo over phosphorus pentoxide to afford the title compound (0.473 g, 0.0013 mol, 82%) as a white solid (mp 127.0–128.5° C., corrected).

$\delta_H$(250 MHz; d$_6$ DMSO) 1.53–1.86 (8H, m, 4×—CH$_2$—), 3.70 (3H, s, —OCH$_3$), 4.22 (2H, s, Ar—CH$_2$—C), 4.74 (1H, m, —CH—), 6.19 (3H, bs, —NH$_3^+$), 6.83 (1H, dd, Ar—H), 6.89 (1H, d, Ar—H) 6.94–6.97 (2H, m, Ar—H), 7.14–7.24 (2H, m, Ar—H). ν(KBr Disc) 3086, 3068, 2996, 2957, 2930, 2902, 2872, 2830, 2765, 2711, 2680, 2581, 2561, 2367, 2344, 2288, 2003, 1620, 1607, 1591, 1572, 1518, 1494, 1464, 1443, 1365, 1330, 1264, 1231, 1194, 1166, 1135, 1094, 1031, 998, 967, 936, 879, 864, 817, 783, 739 cm$^{-1}$.

EXAMPLE 14

2-((3-Cyclopentyloxy-4-methoxy)benzyl)-4-methoxy-benzoxazole 2-((3-Cyclopentyloxy-4-methoxy)benzyl)-4-hydroxy-benzoxazole (0.701 g, 0.0021 mol) and potassium carbonate (0.351 g, 0.0025 mol) were suspended in acetone (25 ml). Dimethyl sulfate (0.194 ml, 0.0021 mol) was added and the mixture was heated to reflux. After 17 hours, ammonia (0.4 ml of a concentrated solution, ρ=0.88 kgdm$^{-3}$) was added and heating was continued. After 15 minutes, the reaction mixture was allowed to cool to room temperature and evaporated in vacuo. The residue was diluted with water (50 ml) and extracted with dichloromethane (30 ml, 2×50 ml). The organic layers were combined, washed with sodium hydroxide (60 ml of a 3 M solution) and water (50 ml), dried over calcium sulfate, evaporated in vacuo and purified by flash chromatography (SiO$_2$, dichloromethane/ethanol/ammonia 500:9:1 v/v/v) and recrystallisation from ethanol/water to afford the title compound (0.278 g, 0.00079 mol, 38%) as a white crystalline solid (mp 59.4–61.2° C., corrected).

$\delta_H$(250 MHz; d$_6$ DMSO) 1.54–1.86 (8H, m, 4×—CH$_2$—), 3.71 (3H, s, —OCH$_3$), 3.92 (3H, s, —OCH$_3$), 4.20 (2H, s, Ar—CH$_2$—C), 4.74 (1H, m, —CH—), 6.84 (1H,dd,6'-H), 6.89 (1H, dd,Ar—H), 6.91 (1H,d,5'-H), 6.95 (1H, d, 2'-H), 7.21 (1H, dd, Ar—H), 7.27 (1H, t, 6-H). ν(KBr Disc) 3078, 3012, 2965, 2952, 2913, 2896, 2886, 2870, 2840, 1619, 1594, 1570, 1512, 1498, 1460, 1446, 1430, 1370, 1355, 1344, 1327, 1315, 1284, 1266, 1232, 1182, 1147, 1093, 1050, 1023, 989, 977, 964, 949, 924, 909, 866, 847, 819, 782, 743, 698, 676, 660, 645, 635, 605 cm$^{-1}$.

EXAMPLE 15

2-((3-Cyclopentyloxy-4-methoxy)benzyl)-7-(nicotinoyl-amino)-benzoxazole

Nicotinoyl chloride hydrochloride (0.402 g, 0.0023 mol) was added in one portion to a solution of 7-amino-2-((3-cyclopentyloxy-4-methoxy)benzyl)-benzoxazole (0.498 g, 0.0015 mol) in pyridine (5 ml). The mixture was stirred at room temperature for 5 minutes, then 4-dimethylaminopyridine (0.005 g) was added and stirring was continued. After 1 hour, methanol (5 ml) was added and stirring was continued. After 16 hours, the reaction mixture was evaporated in vacuo and the residue was purified by flash chromatography (SiO$_2$, dichloromethane/methanol, 20:1 v/v) to furnish a brown solid (0.390 g). The solid was dissolved in dichloromethane/ether (15 ml of a 2:1 v/v mixture) and hydrogen chloride (3 ml of a 1 M solution in ether) was added. A gum was formed. The gum was partitioned between dichloromethane (50 ml) and sodium hydrogen carbonate (50 ml of a saturated aqueous solution). The dichloromethane layer was dried over calcium sulfate and evaporated in vacuo to furnish the title compound (0.213 g, 0.0005 mol, 37%) as a white powder (mp 163.4–165.6° C., corrected).

$\delta_H$(250 MHz; d$_6$ DMSO) 1.44–1.80 (8H, m, 4×—CH$_2$—), 3.68 (3H, s, —OCH$_3$), 4.23(2H, s, Ar—CH$_2$—C), 4.72 (1H, m, —CH—), 6.84 (1H, dd, 6'-H), 6.88 (1H, d, 5'-H), 6.98 (1H, bs, 2'-H), 7.34 (1H, t, 5-H), 7.42 (1H, d, Ar—H), 7.56 (1H, dd, Ar—H), 7.59 (1H, dd, pyridine 5-H), 8.33 (1H, dt, pyridine 4-H), 8.79 (1H, dd, pyridine 6-H), 9.14 (1H, d, pyridine 2-H), 10.79 (1H, s, NH). ν(KBr Disc) 3246, 3229, 3179, 3144, 3109, 3087, 3052, 3004, 2962, 2934, 2910, 2873, 2856, 2834, 1651, 1630, 1591, 1576, 1545, 1514, 1494, 1478, 1464, 1442, 1426, 1359, 1323, 1260, 1237, 1192, 1171, 1161, 1141, 1094, 1048, 1026, 996, 970, 905, 856, 817, 793, 741, 707, 642, 622, 607 cm$^{-1}$.

EXAMPLE 16

2-((3-Cyclopentyloxy-4-methoxy)benzyl)-7-(isonicotinoyl-amino)-benzoxazole Hydrochloride (a) 2-((3-Cyclopentyloxy-4-methoxy)benzyl)-7-(isonicotinoylamino)-benzoxazole Isonicotinoyl chloride hydrochloride (0.404 g, 0.0023 mol) was added in one portion to a solution of 7-amino-2-

((3-cyclopentyloxy-4-methoxy)benzyl)-benzoxazole (0.496 g, 0.0015 mol) in pyridine (5 ml) containing dimethylaminopyridine (0.005 g). The mixtures, which contained some suspended solids was stirred at room temperature. After 1 h, methanol (5 ml) was added and the mixture was evaporated in vacuo and the residue was partitioned between dichloromethane (30 ml) and water (30 ml). The layers were separated and the aqueous layer was extracted with dichloromethane (20 ml). The organic layers were combined, dried over calcium sulfate and evaporated in vacuo to furnish the title compound (0.48 g, 0.0011 mol, 74%) as a nearly colourless oil which contained about 3% pyridine w/w as judged by proton-NMR.

$\delta_H$(250 MHz; $d_6$ DMSO) 1.46–1.80 (8H, m, 4×—CH$_2$—), 3.70 (3H, s, —OCH$_3$), 4.24 (2H, s, Ar—CH$_2$—C), 4.31 (1H, m, cyclopentyl —CH—), 6.85 (1H, dd, 6'-H), 6.89 (1 H, d, 5'-H), 6.99 (1H, dd, 2'-H), 7.36 (1H, t, 5-H), 7.44 (1H, dd, Ar—H), 7.58 (1 H, dd, Ar—H), 7.91 (2H, m, pyridyl-H), 8.82; (2H, m, pyridyl-H), 10.83 (1H, s, NH).

(b) 2-((3-Cyclopentyloxy-4-methoxy)benzyl)-7-(isonicotinoyl-amino)-benzoxazole hydrochloride 2-((3-Cyclopentyloxy-4-methoxy)benzyl)-7-(isonicotnoylamino)-benzoxazole (0.48 g, 0.0011 mol) was dissolved in dichloromethane (5 ml). Hydrogen chloride (5 ml of a 1 m solution in ether) was added and the resulting precipitate was collected by filtration and set aside at room temperature over phosphorus pentoxide in vacuo to afford the title compound (0.489 g, 0.0010 mol, 94%) as a yellow solid (mp 151.2–155.1° C., corrected).

$\delta_H$(250 MHz; $d_6$ DMSO) 1.45–1.79 (8H, m, 4×—CH$_2$—), 3.68 (3H, s, —OCH$_3$), 4.23 (2H, s, Ar—CH$_2$—C), 4.71 (1H, m, —CH—), 6.83 (1H, dd, 6'-H), 6.87 (1H, d, 5'-H), 6.96 (1H bs, 2'-H), 7.36 (1H, t, 5-H), 7.47 (1H, d, Ar—H), 7.59 (1H, d, Ar—H), 8.24 (2H, d, pyridyl-H), 9.00 (2H, d, pyridyl-H), 11.22 (1H, s, NH). ν(KBr Disc) 3425, 3186, 3146, 3109, 3081, 3057, 3034, 3016, 2997, 2951, 2904, 2866, 2830, 2810, 2752, 2705, 2566, 2082, 1680, 1635, 1603, 1573, 1542, 1515, 1464, 1428, 1365, 1339, 1292, 1262, 1239, 1187, 1165, 1136, 1090, 1073, 1052, 1028, 997, 969, 941, 911, 880, 835, 791, 744, 711, 679, 651 cm$^{-1}$.

EXAMPLE 17

2-((3-Cyclopentyloxy-4-methoxy)benzyl)-7-(2-pyridine-carbonylamino)-benzoxazole

A solution of 1,1'-carbonyl diimidazole (1.45 g, 0.0089 mol) in dichloromethane (10 ml) was added to a suspension of picolinic acid (0.737 g, 0.0060 mol) in dichloromethane (10 ml) under argon at room temperature. As the mixture was stirred the suspended solids dissolved. After 2 hours, this solution was added to a solution of 7-amino-2-((3-cyclopentyloxy-4-methoxy)benzyl)-benzoxazole (1.006 g, 0.0030 mol) and pyridine (0.25 ml) in dichloromethane (10 ml) and the mixture was stirred at room temperature. After 6 days the reaction mixture was diluted with water (50 ml) and extracted with dichloromethane (2×50 ml). The organic layers were combined, washed with water (2×30 ml) and sodium hydrogen carbonate (2×50 ml of a saturated solution), dried over calcium sulfate, evaporated in vacuo and purified by flash chromatography (SiO$_2$, petrol/ethyl acetate, 2:1 v/v) to afford the title compound (0.269 g, 0.0006 mol, 20%) as an off white solid (mp 119.4–122.3° C., corrected).

$\delta_H$(250 MHz; $d_6$ DMSO) 1.47–1.81 (8H, m, 4×—CH$_2$—), 3.71 (3H, s, —OCH$_3$), 4.28 (2H, s, Ar—CH$_2$—C), 4.75 (1H, m, —CH—), 6.85 (1H, dd, 6'-H), 6.90 (1H, d, 5'-H), 7.00 (1H,dd, 2'-H), 7.36 (1H, t, 5-H), 7.52 (1H, d, Ar—H), 7.73 (1H, m, pyridine Ar—H), 7.84 (1H, d, Ar—H), 8.11 (1H, dt, pyridine Ar—H), 8.19 (1H, d, pyridine Ar—H), 8.77 (1H, d, pyridine Ar—H), 10.66 (1H, s, NH). ν(KBr Disc) 3336, 2961, 2873, 2836, 1685, 1637, 1618, 1590, 1574, 1536, 1512, 1471, 1447, 1434, 1420, 1352, 1340, 1288, 1260, 1234, 1187, 1163, 1144, 1127, 1086, 1049, 1023, 997, 964, 946, 924, 904, 888, 851, 813, 789, 772, 740, 686, 646, 611 cm$^{-1}$.

EXAMPLE 18

7-((Benzyloxycarbonyl)amino)-2-((3-Cyclopentyloxy-4-methoxy)-benzyl)-benzoxazole 7-Amino-2-((3-Cyclopentyloxy-4-methoxy)benzyl)-benzoxazole (0.685 g, 0.0020 mol) was dissolved in pyridine (10 ml) containing 4-dimethylaminopyridine (ca 0.05 g). Benzyl chloroformate (0.47 ml, 0.56 g, 0.0033 mol) was added dropwise and the mixture was stirred at room temperature. After 5.5 hours, water (10 ml) and hydrochloric acid (5 ml of a 10 M solution) were added and the mixture was extracted with dichloromethane (2×25 ml). The diclo-romethane extracts were combined, dried over calcium sulfate, evaporated in vacuo, and purified by flash chromatography (SiO$_2$, petrol/ethyl acetate 3:1 v/v) to furnish the title compound (0.781 g, 0.0017 mol, 82%) as a pale brown solid (mp 109.7–112.2° C., corrected).

$\delta_H$(250 MHz; $d_6$ DMSO) 1.52–1.82 (8H, m, 4×—CH$_2$—), 3.70 (3H, s, —OCH$_3$), 4.21 (2 H, s, Ar—CH$_2$—C), 4.75 (1H, m, —CH—), 5.16 (2 H, s, Ar—CH$_2$—O), 6.85 (1H, dd, 6'-H), 6.89 (1H, d, 5'-H), 6.97 (1H, bs, 2'-H), 7.23–7.44 (8H, m, Ar—<u>H</u>) 9.93 (1 H, s, NH). ν(KBr Disc) 3436, 3273, 3058, 2952, 2940, 2908, 2870, 2832, 1702, 1575, 1540, 1516, 1464, 1456, 1441, 1426, 1350, 1272, 1263, 1257, 1243, 1199, 1160, 1146, 1127, 1100, 1068, 1042, 1029, 1004, 967, 898, 852, 845, 803, 787, 770, 757, 742, 697, 677, 620, 613 cm$^{-1}$.

EXAMPLE 19

2-((3-Cyclopentyloxy-4-methoxy)benzyl)-7-bromo-benzoxazole (a) 2-Bromo-6-nitrophenol tert-Butylamine (7.6 ml) in toluene (50 ml) was cooled to −20° C. Bromine (1.7 ml, 5.4 g, 0.034 mol) in dichloromethane (10 ml) was added dropwise and the mixture was cooled to −72° C. 2-Nitrophenol (5.06 g, 0.036 mol) in dichloromethane (10 ml) was added over 0.25 hours and on completion of the addition the mixture was allowed to warm to room temperature. After 18 hours, the reaction mixture was acidified with concentrated HCl, diluted with water (150 ml) and extracted with ethyl acetate (2×100 ml, 50 ml). The organic extracts were combined, washed with water (200 ml) and brine (100 ml), dried over calcium sulfate, evaporated in vacuo, and purified by flash chromatography (SiO$_2$, petrol/dichloromethane 2:1 v/v) to furnish the title compound as a highly crystalline yellow solid contaminated with 18% w/w 2,4-di-bromo-6-nitrophenol (2.05 g, 82% pure, 0.0077 mol, 21%)

$\delta_H$(250 MHz; $d_6$ DMSO) 2-bromo-6-nitrophenol 7.00 (1H, dd, 4-H), 7.92–7.98 (2 H, m, Ar—H), 11.1 (1H, bs, Ar—OH).

$\delta_H$(250 MHz; $d_6$ DMSO) 2,4-di-bromo-6-nitrophenol 8.12 (1H, d, Ar—<u>H</u>), 8.19 (1H, d, Ar—<u>H</u>).

(b) 6-Amino-2-bromophenol

2-Bromo-6-nitrophenol (1.506 g, 0.0057 mol, containing 2,4-di-bromo-6-nitrophenol, 18% w/w) and sodium hydrosulfite (3.05 g, 85%, 0.015 mol) were heated at reflux in ethanol/water (50 ml of a 5:1 v/v mixture). After 2 hours, the reaction mixture was diluted with water (150 ml) and extracted with dichloromethane (3×50 ml), and ethyl acetate (100 ml). The organic extracts were combined, dried over calcium sulfate, evaporated in vacuo, and purified by flash chromatography ($SiO_2$, petrol/ether 1:1 v/v) to furnish a mixture of the title compound and 6-amino-2,4-di-bromophenol (0.600 g, of a 76:24 w/w mixture as judged by 1 H-NMR). Yield 6-amino-2-bromophenol, 43%.

$\delta_H$(250 MHz; $d_6$ DMSO) 6-Amino-2-bromophenol ca 5.3 (2H, bs, —$NH_2$), 6.51 (1H, t, 4-H), 6.63 (1H, dd, Ar—H), 6.66 (1H, dd, Ar—H).

$\delta_H$(250 MHz; $d_6$ DMSO) 6-Amino-2,4-di-bromophenol 6.73 (1H, d, Ar—H), 6.77 ((1H, d, Ar—H).

(c) 2-Bromo-6-((3-cyclopentyloxy-4-methoxy)phenyl)acetamido-phenol

A solution of 3-cyclopentyloxy-4-methoxyphenylacetic acid (2.997 g, 0.012 mol) in dichloromethane (30 ml) was added to a slurry of 1,1'-carbonyl diimidazole (2.19 g, 0.014 mol) in dichloromethane (15 ml) and the mixture was stirred at room temperature. After 2 hours, a portion (11 ml) of this solution was added dropwise to a solution of 6-amino-2-bromophenol (0.59 g of a mixture containing 6-amino-2-di-bromophenol (0.45 g, 0.0024 mmol), and 6-amino-2,6-di-bromophenol (0.14 g, 0.0005 mol)) in dichloromethane (5 ml) and the mixture was stirred at room temperature. After 64 hours, the mixture was washed with water (15 ml) and the aqueous washings were extracted with dichloromethane. The organic extracts were combined, dried over calcium sulfate, evaporated and purified by flash chromatography ($SiO_2$, dichloromethane/ethanol/ammonia 750:18:2 v/v/v) to furnish a 4:1 w/w (as judged by $^1H$ NMR) mixture of the title compound and 6-((3-cyclopentyloxy-4-methoxy)phenyl)-2,4-di-bromo-acetamido-phenol (0.693 g) as a viscous yellow oil.

$\delta_H$(250 MHz; $CDCl_3$) 1.5–2.0 (8H, m, 4×—$CH_2$—), 3.74 (2H, s, Ar—$CH_2$—), 3.88 (3H, s, —$OCH_3$), 4.80 (1H, m, —CH—), 6.75 (1H, t, 4-H), 6.80–6.93 (3H, m, Ar—H), 7.27 (1H, m, Ar—H), 7.50 (1H, dd, Ar—H), 7.54 (1H, s, Ar—OH), 7.55 (1H, bs, —NH—). Two peaks directly attributable to the 3-H and 5-H in 6-((3-cyclopentyloxy-4-methoxy)phenyl)-2,4-di-bromo-acetamido-phenol are observed.

$\delta_H$(250 MHz; $CDCl_3$) 7.39 (1H, d, Ar—H), 7.81 (1H, d, Ar—H).

(d) 2-((3-Cyclopentyloxy-4-methoxy)benzyl)-7-bromo-benzoxazole

2-Bromo-6-((3-cyclopentyloxy-4-methoxy)phenyl)acetamido-phenol (0.693 g, 80%, 0.0013 mol) was heated at reflux in xylene (25 ml) containing pyridinium toluenesulfonate (0.124 g, 0.0005 mol). After 22 h the reaction mixture was cooled to room temperature, diluted with water (40 ml) and extracted with dichloromethane (3×40 ml). The organic extracts were combined, washed with water (2×40 ml) and brine (2×40 ml), dried over calcium sulfate, evaporated in vacuo and purified by flash chromatography ($SiO_2$, dichloromethane/ethanol/ammonia 750:18:2 v/v/v) to furnish the title compound (0.287 g, 0.00071 mol, 54%) as a pale brown solid (mp 48.3–51.4° C., corrected).

$\delta_H$(250 MHz; $d_6$ DMSO) 1.51–1.86 (8H, m, 4×—$CH_2$—), 3.71 (3H, s, —$OCH_3$), 4.28 (2 H, s, Ar—$CH_2$—), 4.74 (1H, m, —CH—), 6.85 (1H, dd, 6'-H), 6.91 (1H, d, 5'-H), 6.98 (1H, d, 2'-H), 7.29 (1H, t, 5-H), 7.57 (1H, dd, Ar—H), 7.69 (1H, d, Ar—H). ν(KBr Disc) 3070, 3016, 2949, 2865, 2841, 1610, 1593, 1566, 1513, 1471, 1452, 1443, 1423, 1360, 1336, 1306, 1273, 1257, 1235, 1218, 1187, 1163, 1147, 1132, 1091, 1023, 999, 970, 930, 899, 866, 852, 806, 781, 764, 736, 671, 630, 616 $cm^{-1}$.

EXAMPLE 20

2-((3,5-Di-isopropyl-4-hydroxy)benzyl)-4-hydroxy-benzoxazole

(a) N-((3,5-Di-isopropyl-4-hydroxy)benzyl)piperidine

Piperidine (4.5 ml, 3.9 g, 0.046 mol) in ethanol (volume not recorded) was added to a stirred solution of formaldehyde (3 ml, of a 37% w/w solution in water) in ethanol (8 ml) at 0° C. The mixture was allowed to warm to ambient temperature and 2,6-di-isopropylphenol (7.2 g, 0.040 mol) was added. The mixture, which was originally colorless, became green as stirring continued at room temperature. After 1 hour, the reaction mixture was heated to reflux. After a further 3 h the reaction mixture was poured onto water (450 ml), acidified to pH 1 (concentrated hydrochloric acid) and extracted with ether (2×100 ml). The aqueous layer was neutralised to pH 7 (concentrated sodium hydroxide) under a layer of ether (300 ml) whilst undergoing vigorous stirring. The layers were separated and the aqueous layer was extracted with ether (100 ml). The neutral ether extracts were combined, dried over calcium sulfate and evaporated in vacuo to furnish the title compound (12.06 g, 0.044 mol, 110%) as a pale pink oil which solidified on standing.

$\delta_H$(250 MHz; $d_6$ DMSO) 1.12 (12H, d, 2×—CH($CH_3$)$_2$), 1.30–1.55 (6H, m, —N—$CH_2CH_2CH_2CH_2$—), 2.26 (4H, bs, —$CH_2$—N—$CH_2$—), 3.26 (2H, m, —CH($CH_3$)$_2$), 3.28 (2H, s, Ar$CH_2$—), 6.85 (2H, s,2'-,6'-Ar—H), 7.89 (1H, bs, Ar—OH)

(b) (3,5-Di-isopropyl-4-hydroxy)phenylacetonitrile

N-((3,5-Di-isopropyl-4-hydroxy)benzyl)piperidine (5.46 g, 0.020 mol) was dissolved in ether (150 ml). Iodomethane (3.8 ml, 8.7 g, 0.06 mol) was added and the mixture was allowed to stir at room temperature. After 42 hours, a thick white precipitate had formed. This was removed by filtration and dried in vacuo. The resulting white solid (6.03 g) was suspended in isopropanol/water (40 ml of a 10:1 v/v mixture). Potassium cyanide (1.84 g, 0.028 mol) was added and the mixture was stirred at reflux for 5 hours, then at room temperature for 16 hours, then at reflux for a further 2 hours. The mixture was then diluted with water (100 ml) and extracted with ethyl acetate (100 ml, 2×50 ml). The ethyl acetate extracts were combined, washed with water (2×75 ml) and brine (50 ml), dried over calcium sulfate and evaporated in vacuo to furnish a green oil (3.405 g) which was purified by flash chromatography ($SiO_2$, petrol/ethyl acetate 9:1 v/v) to afford the title compound(3.26 g, 0.015 mol, 76%, $R_f$ 0.13).

$\delta_H$(250 MHz; $d_6$ DMSO) 1.13 (12H, d, 2×—CH($CH_3$)$_2$), 3.28 (2 H, m, —CH($CH_3$)$_2$), 3.85 (2 H, s, Ar$CH_2$—), 6.93 (2 H, s, 2'-,6'-Ar—H), 8.17 (1H, bs, Ar—OH).

(c) (3,5-Di-isopropyl-4-hydroxy)phenylacetic Acid (3,5-Di-isopropyl-4-hydroxy)phenylacetonitrile (2.86 g, 0.013 mol) was dissolved in ethanol/water (40 ml of a 4:1 v/v mixture) and heated to reflux. After 24 hours, the reaction mixture was cooled to room temperature and poured into water (70 ml), acidified to pH 1 with concentrated hydrochloric acid and set aside at 4° C. After 16 hours, the mixture was made basic with sodium hydroxide and extracted with ether (150 ml). The aqueous layer was acidified to pH 1 with concentrated hydrochloric acid and extracted with ether (150 ml, 50 ml). The acidic ether extracts were combined, dried over calcium sulfate and evaporated in vacuo to furnish the title compound (2.10 g, 0.0089 mol, 68%) as pale brown oil which slowly crystallised in vacuo.

$\delta_H$(250 MHz; $d_6$ DMSO) 1.13 (12H, d, 2×—CH(C$\underline{H}_3$)$_2$), 3.27 (2 H, m, —C$\underline{H}$(CH$_3$)$_2$), 3.41 (2 H, s, ArCH$_2$—), 6.85 (2 H, s, 2'-,6'-Ar—H), 7.95 (1H, bs, Ar—OH).

(d) 2-Aminoresorcinol

2-Nitroresorcinol (4.995 g, 0.032 mol) was suspended in ethanol (90 ml). Platinum(IV) oxide (0.356 g) was added and the mixture was shaken under an atmosphere of hydrogen (pH$_2$ 100 psi). After 2.75 hours (pH$_2$ 90 psi) the reaction mixture was filtered through celite. The residue was washed with methanol (50 ml) and the combined filtrate and washings were evaporated in vacuo at 30° C. During the course of the evaporation the solution, which was originally pale yellow, darkened considerably. A brown solid was obtained which was suspended in dichloromethane (100 ml) and re-evaporated to dryness. Yield 3.83 g (0.031 mol, 95%).

$\delta_H$(250 MHz; $d_6$ DMSO) 3.85 (2 H, bs, —NH$_2$), 6.16–6.29 (3 H, m, Ar—H), 8.85 (2 H, bs, —OH).

$\delta_C$(63 MHz; $d_6$ DMSO) 106.7 (protonated aromatic C), 115.7 (protonated aromatic C), 123.8 (quaternary aromatic C), 144.9 (quaternary aromatic C).

(e) 2-((3,5-Di-isopropyl-4-hydroxyphenyl) acetylamido)-resorcinol (3,5-Di-isopropyl-4-hydroxyphenyl)acetic acid (2.08 g, 0.009 mol), suspended in dichloromethane (12 ml), was added, under argon, to a stirred suspension of 1,1'-carbonyl diimidazole (1.74 g, 0.011 mol) in dichloromethane (20 ml) and the mixture was stirred at room temperature. After 2 hours, this mixture was added to a suspension of 2-aminoresorcinol (1.52 g, 0.012 mol) in dichloromethane (20 ml) and the mixture was stirred at room temperature. After 18 hours, the reaction mixture was washed with water (60 ml) and the aqueous wash was extracted with ethyl acetate (4×80 ml). The organic extracts were combined, dried over calcium sulfate and evaporated in vacuo and purified by flash chromatography (SiO$_2$, dichloromethane/ethanol/ammonia, 750:18:2 v/v/v). to afford the title compound (1.7 g, 0.0050 mol, 56%).

$\delta_H$(250 MHz; $d_6$ DMSO) 1.15 (12H, d, 2×—CH(C$\underline{H}_3$)$_2$), 3.29(2 H, m, —C$\underline{H}$(CH$_3$)$_2$), 3.62 (2 H, s, ArCH$_2$—), 6.35 (2 H, d, 4-,6-H), 6.87 (1H, t, 5-H), 7.00 (2 H, s,2'-,6'-H), 7.95 (1H, bs, —NH—), 9.46 (3 H, bs, Ar—OH).

(f) 2-((3,5-Di-isopropyl-4-hydroxy)benzyl)-4-hydroxy-benzoxazole 2-((3,5-Di-isopropyl-4-hydroxyphenyl)acetylamido) resorcinol (1.7 g, 0.0050 mol) and pyridinium toluenesulfonate (0.440 g, 0.0018 mol) were suspended in xylene (50 ml) and heated to reflux. After 17 hours, the reaction mixture was allowed to cool, diluted with ethyl acetate (80 ml) and washed with water (2×100 ml) and brine (2×100 ml), evaporated in vacuo and purified by flash chromatography (SiO$_2$, dichloromethane/ethanol/ammonia 750:18:2 v/v/v) to afford the title compound (0.830 g, 0.0026 mol, 52%) as a pale brown solid (mp 143.5–149.9° C., corrected).

$\delta_H$(250 MHz; $d_6$ DMSO) 1.12 (12H, d, 2×—CH(C$\underline{H}_3$)$_2$), 3.27 (2 H, m, 2×—C$\underline{H}$(CH$_3$)$_2$), 4.14 (2 H, s, Ar—CH), 6.70 (1H, dd, Ar—H), 6.95 (2 H, s, 2'-,6'-H), 7.03 (1H, dd, Ar—H), about 7.1; (1H, bs, Ar—OH), 7.11 (1H, t, 6-H), 8.07 (1H, bs, Ar—OH). ν(KBr Disc) 3474, 2960, 2930, 2872, 1731, 1627, 1616, 1569, 1505, 1461, 1384, 1365, 1344, 1321, 1288, 1267, 1201, 1141, 1125, 1075, 1054, 1041, 776, 740 cm$^{-1}$.

EXAMPLE 21

2-((3,5-Dimethyl-4-hydroxy)benzyl)-4-hydroxybenzoxazole (a) N-((3,5-Dimethyl-4-hydroxy)benzyl)piperidine Piperidine (4.5 ml, 3.9 g, 0.046 mol) in ethanol (4.5 ml) was added to a stirred solution of formaldehyde (3 ml, of a 37% w/w solution in water) in ethanol (8 ml) at 0° C. The mixture was allowed to warm to ambient temperature and 2,6-dimethylphenol (4.98 g, 0.041 mol) in ethanol (10 ml) was added. After 1.5 hours, the reaction mixture was heated to reflux. After a further 4 hours, the reaction mixture was poured onto water (500 ml), acidified to pH 1 (concentrated hydrochloric acid) and extracted with ether (150 ml). The aqueous layer was neutralized to pH 7 (concentrated sodium hydroxide) under a layer of ether (300 ml) while undergoing vigorous stirring. The layers were separated and the aqueous layer was extracted with ether (2×100 ml). The neutral ether extracts were combined, dried over calcium sulfate and evaporated in vacuo to furnish the title compound (9.28 g, 0.042 mol, 104%) as a pink solid.

$\delta_H$(250 MHz; $d_6$ DMSO) 1.30–1.55 (6H, m, —N—CH$_2$ C$\underline{H}_2$ C$\underline{H}_2$ C$\underline{H}_2$ —), 2.11 (6H, s, 2×—CH$_3$), 2.25 (4 H, bs, —CH$_2$—N—CH$_2$—), 3.18 (2 H, s, ArCH$_2$—), 6.77 (2 H, s, 2'-,6'-Ar—H), 8.05 (1H, bs, Ar—OH)

(b) (3,5-Dimethyl-4-hydroxy)phenylacetonitrile

N-((3,5-Dimethyl-4-hydroxy)benzyl)piperidine (9.2 g, 0.042 mol) was dissolved in ether (70 ml). Iodomethane (5.4 ml, 12.3 g, 0.086 mol) was added and the mixture was set aside at room temperature. After 1 8 hours, a thick gum had formed. The supernatant liquor was removed and the gum was washed with ether and suspended in isopropanol/water (100 ml of a 10:1 v/v mixture). Potassium cyanide (5.48 g, 0.084 mol) was added and the mixture was stirred at reflux for 1.5 hours, then at room temperature for 16 hours. Water (100 ml) was added and the mixture was extracted with ethyl acetate (300 ml, 3×200 ml). The ethyl acetate extracts were combined, washed with water (400 ml) and brine (250 ml), dried over calcium sulfate and evaporated in vacuo to furnish the title compound (5.72 g, 0.035 mol, 82%).

$\delta_H$(250 MHz; $d_6$ DMSO) 2.14 (6H, s, 2×—CH$_3$), 3.78 (2 H, s, ArCH$_2$—), 6.86 (2 H, s, 2'-,6'-Ar—H), 8.32 (1H, bs, Ar—OH).

(c) (3,5-Dimethyl-4-hydroxy)phenylacetic acid (3,5-Dimethyl4-hydroxy)phenylacetonitrile (5,72 g, 0.035 mol) was dissolved in ethanol/water (100 ml of a 4:1 v/v mixture). Sodium hydroxide (11.11 g, 0.28 mol) was added and the mixture was heated to reflux. After 24 hours, the reaction mixture was cooled to room temperature and poured into water (300 ml), acidified to pH 1 with concentrated hydrochloric acid and extracted with ether (200 ml, 2×150 ml). The acidic ether extracts were combined, extracted with saturated sodium carbonate solution (200 ml, 2×100 ml, 50 ml). The aqueous layers were combined, acidified to pH 1 with concentrated hydrochloric acid and set aside at 4° C. A precipitate formed which was isolated by filtration, washed with water (200 ml) and set aside in vacuo to furnish the title compound (3.54 g, 0.020 mol, 55%) as pale brown solid.

$\delta_H$(250 MHz; $d_6$ DMSO) 2.14 (6H, s, 2×—CH$_3$), 3.35 (2 H, s, ArCH$_2$—), 6.78 (2 H, s, 2'-,6'-Ar—H), 8.10 (1H, bs, Ar—OH), 12.15 (1H, bs, —COOH).

(d) 2-((3,5-Dimethyl-4-hydroxyphenyl)acetylamido) resorcinol (3,5-Dimethyl-4-hydroxyphenyl)acetic acid (3.50 g, 0.019 mol), suspended in dichloromethane (30 ml), was added, under argon, to a stirred suspension of 1,1'-carbonyl diimidazole (4.21 g, 0.026 mol) in dichloromethane (30 ml) over 0.25 hours and the mixture was stirred at room temperature. After 2.5 hours, this mixture was added over 0.75 hours to a suspension of 2-aminoresorcinol (4.2 g, 0.034 mol) in dichloromethane (40 ml) and the mixture was stirred at room temperature. After 18 hours, the reaction mixture was washed with water (100 ml) and 1 M hydrochloric acid (200 ml). The aqueous layers were combined and extracted with ethyl acetate (4×100 ml). The organic extracts were combined, washed with water (2×100 ml) and brine (100 ml), dried over calcium sulfate, evaporated in vacuo, and purified by flash chromatography (SiO$_2$, dichloromethane/methanol, 50:1 v/v). to afford the title compound (2.20 g, 0.0077 mol, 39%).

$\delta_H$(250 MHz; $d_6$ CDCl$_3$) 2.23 (6H, s, 2×—CH$_3$), 3.70 (2 H, s, Ar—CH$_2$), 6.44 (2 H, d, 4-,6-H), 6.91 (1H, t, 5-H), 6.96 (2 H, s, 2'-,6'-H), 7.88 (1H, bs, —NH—).

(e) 2-((3,5-Dimethyl-4-hydroxy)benzyl)-4-hydroxy-benzoxazole 2-((3,5-Dimethyl-4-hydroxyphenyl)acetylamido) resorcinol (2.2 g, 0.0077 mol) and pyridinium toluenesulfonate (0.580 g, 0.0024 mol) were suspended in xylene (100 ml) and heated to reflux. After 17 hours, the reaction mixture was allowed to cool, diluted with ethyl acetate (200 ml) and washed with water (2×200 ml) and brine (2×150 ml), evaporated in vacuo and purified by flash chromatography (SiO$_2$, dichloromethane/methanol 25:1 v/v, 50:1 v/v, 100:1 v/v, petrol/ether 1:1 v/v) to afford the title compound (0.400 g, 0.0015 mol, 19%) as an off-white solid (mp 202.9–212.9° C., corrected).

$\delta_H$(250 MHz; $d_6$ DMSO) 2.12 (6H, s, —CH$_3$), 4.06 (2 H, s, Ar—CH$_2$—C), 6.70 (1H, dd, Ar—H), 6.86 (2 H, s, 2'-,6'-H), 7.01 (1H, d, Ar—H), 7.10 (1H, t, 6-H), 8.14 (1H, bs, Ar—OH), 10.14 (1H, bs, Ar—OH). v(KBr Disc) 3428, 3127, 1616, 1507, 1485, 1453, 1337, 1305, 1264, 1247, 1196, 1166, 1148, 1058, 1040, 737 cm$^{-1}$.

EXAMPLE 22

2-((3,5-Di-t-butyl-4-hydroxy)benzyl-7-(2-(2-pyridyl)-ethynyl)-benzoxazole (a) 2-Bromo-6-(3,5-di-t-butyl-4-hydroxyphenyl) acetylamido-phenol (3,5-Di-t-butyl-4-hydroxyphenyl)acetic acid (5.03 g, 0.019 mol) in dichloromethane (20 ml) was added dropwise over 0.25 hours to a stirred solution of 1,1'-carbonyl diimidazole (4.68 g, 0.029 mol) in dichloromethane (60 ml). After 2 hours, this solution was added dropwise over 0.5 hours to a solution of 6-amino-2-bromophenol (4.30 g of a mixture containing 6-amino-2-di-bromophenol (3.60 g, 0.019 mmol), and 6-amino-2,6-di-bromophenol (0.70 g, 0.003 mol)) in dichloromethane (30 ml). After 18 hours, the reaction mixture was diluted with ethyl acetate (200 ml) and washed with 2 M hydrochloric acid (100 ml), and water, dried over magnesium sulfate, evaporated in vacuo, and purified by flash chromatography (SiO$_2$, dichloromethane) to furnish a 4:1 w/w (as judged by $^1$H NMR) mixture of 2-bromo-6-(3,5-di-t-butyl-4-hydroxyphenyl)acetylamido-phenol and 2,4-di-bromo-6-(3,5-di-t-butyl-4-hydroxyphenyl)acetylamido-phenol (6.90 g) as a pale pink solid.

$\delta_H$(250 MHz; $d_6$ DMSO) 1.37 (18 H, s, 2×(—CH$_3$)$_3$), 3.62 (2 H, s, Ar—CH$_2$—), 6.78 (1 H, dd, Ar—H), 6.88 (1H, s, —OH) 7.09 (2 H, s, 2'-,6'-H), 7.33 (1H, dd, Ar—H), 7.43 (1 H, dd, 6-H), 9.92 (1H, bs, —NH—), 10.02 (1H, s, —OH).

A signal at $\delta$=7.51 ppm (d) was attributable to 2,4-di-bromo-6-(3,5-di-t-butyl-4-hydroxyphenyl)-acetylamido-phenol.

(b) 7-Bromo-2-((3,5-di-t-butyl-4-hydroxy)benzyl)-benzoxazole

2-Bromo-6-(3,5-di-t-butyl-4-hydroxyphenyl) acetylamido-phenol (6.90 g, 80%, 0.013 mol) and pyridinium toluenesulfonate (1.37 g, 0.0055 mol) were suspended in xylene (165 ml) and heated to reflux. After 17 hours, the reaction mixture was allowed to cool, diluted with water (200 ml) and extracted with ethyl acetate (3×100 ml). The organic extracts were combined, dried over magnesium sulfate, evaporated in vacuo and purified by flash chromatography (SiO$_2$, dichloromethane/petrol 2:1 v/v) to afford the title compound (4.90 g, 0.0015 mol, 92%) as an off-white solid.

$\delta_H$(250 MHz; $d_6$ DMSO) 1.35 (18 H, s, 2×(—CH$_3$)$_3$), 4.24 (2 H, s, Ar—CH$_2$—), 6.95 (1 H, s, —OH) 7.14 (2 H, s, 2'-,6'-H), 7.28 (1H, dd, 5-H), 7.57 (1H, dd, 6-H), 7.69 (1H, dd, Ar—H).

(c) 2-((3,5-Di-t-butyl-4-hydroxy)benzyl-7-(2-(2-pyridyl)-ethynyl)-benzoxazole

Argon was bubbled through a mixture of 7-bromo-2-((3,5-di-t-butyl-4-hydroxy)benzyl)-benzoxazole, (1.002 g, 0.0024 mol), copper(1) iodide (2 mg), and 2-ethynylpyridine (0.320 ml, 0.326 g, 0.0032 mol) in triethylamine (6 ml). After 0.75 hours bis(triphenylphosphine)palladium(II) dichloride (0.045 g, 0.00006 mol) was added and the reaction mixture was flushed with argon for a further 5 minutes then heated to 90° C. After 1.5 hours, a new product was observed by TLC (SiO$_2$, petrol/diethyl ether 1:1 v/v) together with both starting materials. Further portions of 2-ethynylpyridine were added after 2 hours (0.100 ml, 0.102 g, 0.0099 mol) and 4.5 hours (0.200 ml, 0.204 g, 0.0020 mol). No change was observed by TLC. An additional portion of bis(triphenylphosphine)palladium(II) dichloride (0.02 g, 0.00003 mol) was also added after 4.5 hours and the mixture was stirred at 90° C. for a further 3 hours and at ambient temperature for a further 16 hours. No change was observed by TLC. The reaction mixture was evaporated in vacuo and purified by flash chromatography (SiO$_2$, petrol/ether 1:1 v/v) to furnish the title compound (0.225 g, 0.00051 mol, 21%) as a dry khaki foam.

$\delta_H$(250 MHz; $d_6$ DMSO) 1.35 (18 H, s, 2×—C(CH$_3$)$_3$), 4.27 (2 H, s, Ar—CH$_2$), 6.89 (1H, bd, —OH), 7.17 (2 H, s, 2'-H and 6'-H), 7.41 (1H, dd, 5-H), 7.47 (1H, m, Py—H), 7.60 (1H, d, Ar—H), 7.68. (1H, d, Py—H), 7.76 (1H, d, Ar—H), 7.89 (1H, m, Py—H), 8.64 (1H, m, Py—H). ν(KBr Disc) 3633, 3450, 2956, 2927, 2912, 2871, 2221, 1604, 1582, 1564, 1488, 1462, 1424, 1400, 1390, 1361, 1315, 1279, 1259, 1236, 1212, 1189, 1148, 1136, 1121, 1095, 1048, 1036, 989, 822, 795, 776, 741 cm$^{-1}$.

EXAMPLE 23

2-((3,5-Di-isopropyl-4-hydroxy)benzyl-7-(2-(2-pyridyl)-ethynyl)-benzoxazole (a) 2-Bromo-6-(3,5-di-isopropyl-4-hydroxyphenyl) acetylamido-phenol (3,5-Di-isopropyl-4-hydroxyphenyl)acetic acid (6.28 g, 0.027 mol) in dichloromethane (40 ml) was added to a stirred solution of 1,1'-carbonyl diimidazole (6.50 g, 0.04 mol) in dichloromethane (40 ml). After 1 hour, a solution of 6-amino-2-bromophenol (4.0 g of a mixture -containing 6-amino-2-di-bromophenol (3.35 g, 0.018 mmol), and 6-amino-2,6-di-bromophenol (0.65 g, 0.0024 mol)) in dichloromethane (25 ml) was added and the mixture was stirred at room temperature. After 20 hours, the mixture was washed with 1 M hydrochloric acid (2×80 ml), evaporated in vacuo, and purified by flash chromatography (SiO$_2$, petrol/ether 1:1 v/v, ether, and dichloromethane/methanol 20:1 v/v) to furnish a 17:3 w/w (as judged by $^1$H-NMR) mixture of 2-bromo-6-(3,5-di-isopropyl-4-hydroxyphenyl) acetylamido-phenol and 2,4-di-bromo-6-(3,5-d-isopropyl-4-hydroxyphenyl)acetylamido-phenol (5.70 g) as a yellow solid.

δ$_H$(250 MHz; CDCl$_3$) 1.25 (12H, d, 2×—CH(C$\underline{H}_3$)$_2$), 3.15 (2 H, m, 2×—C$\underline{H}$(CH$_3$)$_2$), 3.71 (2 H, s, ArCH$_2$—), 4.87 (1H, s, —OH), 6.71 (1H, t, 5-H), 6.98 (2 H, s, 2'-,6'-H), 7.25 (1H, dd, Ar—H), 7.41 (H, dd, Ar—H), 7.53 (1H, bs, —NH—), 7.65 (1H, s, Ar—OH). Two signals at δ=7.36 (d) ppm and 7.77 (d) are attributable to 2,4-di-bromo-6-(3,5-di-isopropyl-4-hydroxyphenyl)acetylamido-phenol.

(b) 7-Bromo-2-(3,5-di-isopropyl-4-hydroxy-benzyl)-benzoxazole

2-Bromo-6-(3,5-di-isopropyl-4-hydroxyphenyl) acetylamido-phenol (2.97 g, 85%, 0.065 mol) and pyridinium p-toluenesulfonate (0.612 g, 0.0024 mol) were suspended in xylene (85 ml) and heated to reflux. After 16 hours, the reaction mixture was allowed to cool, diluted with water (140 ml) and extracted with ethyl acetate (2×70 ml). The organic extracts were combined, washed with water (70 ml), and brine (70 ml), dried over magnesium sulfate, evaporated in vacuo and purified by flash chromatography (SiO$_2$, dichloromethane) to afford the title compound (1.44 g, 0.0039 mol, 60%) as a yellow solid.

δ$_H$(250 MHz; CDCl$_3$) 1.28 (12H, d, 2×—CH(C$\underline{H}_3$)$_2$), 3.15 (2 H, m, 2×—C$\underline{H}$(CH$_3$)$_2$), 4.22; (2 H, s, ArCH$_2$—), 4.87 (1H, s, —OH), 7.13 (2 H, s, 2'-,6'-H), 7.19 (1H, t, 5-H), 7.44 (1H, d, Ar—H), 7.61 (1H, d, Ar—H).

(c) 2-((3,5-di-isopropyl-4-hydroxy)benzyl-7-(2-(2-pyridyl)-ethynyl)-benzoxazole

Argon was bubbled through a mixture of 7-bromo-2-((3, 5-di-isopropyl-4-hydroxy)benzyl)-benzoxazole, (0.785 g, 0.0020 mol), copper(I) iodide (4 mg), and 2-ethynylpyridine (0.400 ml, 0.408 g, 0.0040 mol) in triethylamine (12 ml). After 0.5 hours bis(triphenylphosphine)palladium(II) dichloride (0.074 g, 0.0001 mol) was added and the reaction mixture was flushed with argon for a further 5 minutes then heated to 90° C. After 16 hours, the reaction mixture was evaporated in vacuo and purified by flash chromatography (SiO$_2$, petrol/ether 1:1 v/v) and crystallized from ether to furnish the title compound (0.318 g, 0.00078 mol, 38%) as a green crystalline solid (mp 145.4–148.8° C.).

δ$_H$(250 MHz; d$_6$ DMSO) 1.10 (12H, d, 2×CH(C$\underline{H}_3$)$_2$), 3.25 (2 H, m,2×C$\underline{H}$(CH$_3$)$_2$) 4.25 (2H,s, —CH$_2$—), 7.03 (2H, s, 2'-H and 6'-H), 7.39 (1H, t, 5-H), 7.45 (1H, m, Py—H), 7.59 (1H, d, Ar—H), 7.67 (1H, d, Py—H), 7.80 (1H, d, Ar—H), 7.89 (1H, dt, Py—H), 8.04 (1H, s, Ar—OH), 8.64 (1H, bd, Py—H) ν(KBr Disc) 3280, 2958, 2927, 2868, 2219, 1731, 1721, 1706, 1702, 1691, 1687, 1676, 1591, 1581, 1562, 1463, 1443, 1423, 1319, 1292, 1281, 1260, 207, 1157, 1145, 1122, 1047, 795, 777, 740 cm$^{-1}$.

EXAMPLE 24

Following the procedures set forth in Examples 11 and 12, the PDE III and PDE IV inhibition for the compounds of Examples 13–23 was calculated and compared to rolipram. The results are shown the Table II below expressed as IC$_{50}$ values.

TABLE II

| | IC$_{50}$(μM) | |
| --- | --- | --- |
| EXAMPLE | PDE III | PDE IV |
| 13 | 253.3 | 13.69 |
| 14 | 49.2 | 1.99 |
| 15 | 177.4 | 4.79 |
| 16 | 43.9 | 6.03 |
| 17 | 121.4 | 0.76 |
| 18 | >300 | 3.43 |
| 19 | 2.8 | 0.47 |
| 20 | 34.3 | 3.03 |
| 21 | 104.7 | 24.50 |
| 22 | >300 | 0.07 |
| 23 | 152.2 | 0.26 |

As was the case with the first group of compounds tested, these inventive compounds also provide high levels of PDE-IV inhibition while at the same time relatively low levels of PDE-III inhibition.

EXAMPLE 25

2-(3-Cyclopentyloxy-4-methoxybenzyl)-5-chlorobenzoxazole-7-ethanal

A mixture of 2-(3-cyclopentyloxy-4-methoxy)-5-chloro-7-allylbenzoxazole (10.0 g, 0.026 mole), a 1% solution of osmium tetroxide dissolved in glyme (29 ml, 0.001 mol) and 300 ml of ether, was stirred for 5 minutes. A solution of periodic acid (14 g, 0.06 mol) dissolved in 300 ml of water was added all at once and the mixture was allowed to stir for 24 hours. The ether layer was separated and the aqueous phase was extracted with a further 100 ml of ether. The combined ether layers were washed with 4×75 ml of 10% sodium thiosulfate and then with 100 ml of water. The ether layer was dried evaporated under reduced pressure, to give 12 g of brown oil. This crude product was dissolved in a 50:50 blend of hexane in methylene chloride and applied to a 100 g silica gel flash chromatography column. Elution with 50:50 hexane in methylene chloride followed by pure methylene chloride gave 8.7 g of crude product which crystallized on trituration with an ether-hexane blend. The solid was filtered to give 4.9 g of pale yellow crystals. The residue which remained after evaporation of the ether-hexane solvent (3.8 g), was dissolved in 30% methylene chloride in hexane and purified by flash chromatography on 40 g silica gel. Elution with 300 ml of 30% hexane/methylene chloride gave 0.35 g of oil which contained no product. Elution of the flash column with 450 ml of methylene chloride gave 2.0 g of crude aldehyde. This material was triturated as above and gave 1.35 g of pure aldehyde. The total yield of 2-(3-cyclopentyloxy-4-methoxybenzyl)-5-chlorobenzoxazole-7-ethanal was 62%. A small sample of this material was recrystallized from ether-hexane and the off-white solid exhibited mp 66–68° C.

$^1$H NMR (60 MHz, CDCl$_3$), δ 1.58–1.97 (8H, m,4×CH$_2$), 3.60 (3H,s,OCH$_3$), 3.64 (2H,d,CH$_2$), 3.92 (2H,s,CH$_2$), 4.45 (1H,m,CH), 6.42 (3H,s,3ArH), 6.65 (1H,d,ArH), 7.18 (1H, d,ArH), 9.54 (1H,t,CHO).

EXAMPLE 26

2-(3-Cyclopentyloxy-4-methoxybenzyl)-5-chlorobenzoxazole-7-ethanal Oxime

A sample of hydroxylamine hydrochloride (2.60 g, 0.0375 mol) was dissolved in 6 ml of water and sodium hydroxide (1.5 g, 0.0375 mol) was added. The reaction mixture became warm and was diluted with 10 ml of methanol. A sample of 2-(3-cyclopentyloxy-4-methoxybenzyl)-5-chlorobenzoxazole-7-ethanal (1.0 g, 0.0025 mol), dissolved in 20 ml of methanol, was added to the above solution and the reaction mixture was warmed on a steam bath for 10 minutes. After this solution was cooled in the freezer, the solid oxime crystallized and was filtered. The solid was dried and weighed 0.68 g. The filtrate from above was diluted with water (100 ml) and extracted with methylene chloride (2×100 ml). Evaporation of the solvent afforded a further 0.37 g of pale yellow oxime. The material which initially crystallized from the reaction mix was recrystallized from 12 ml of methanol to yield 0.36 g of 2-(3-cyclopentyloxy-4-methoxybenzyl)-5-chlorobenzoxazole-7-ethanal oxime, mp 149–151° C.

$^1$H NMR (300 MHz, CDCl$_3$) δ 1.40–1.90 (8H,m,4×CH$_2$), 3.62 (3H,s,OCH$_3$), 3.75 (2H,d,CH$_2$), 3.88 (2H,s,CH$_2$), 4.55 (1H,m,CH), 6.50 (2H,bs,ArH), 6.58 (1H,d,ArH), 6.79 (1H, d,ArH),7.18 (1H,d,ArH), 9.00 (1H,bs,NOH).

EXAMPLE 27

2-(3-Cyclopentyloxy-4-methoxybenzyl)-5-chloro-7-(2-hydroxyethyl)Benzoxazole

Sodium borohydride 0.05 g, 0.0013 mol) was added to a stirred solution of 2-(3-cyclopentyloxy-4-methoxybenzyl)-5-chlorobenzoxazole-7-ethanal (1.0 g, 0.0025 mol) in 10 ml ethanol. Stirring was continued for 1 hour. Water (15 ml) was added and the reaction mixture was extracted with 2×50 ml ethyl acetate. The ethyl acetate layer was washed once with water (50 ml), dried and evaporated to give 1.1 g of pale yellow crystals. A small sample of this solid was recrystallized from a blend of ether-hexane to give the title compound as a white solid, mp 74–76° C.

$^1$H NMR(300 MHz, CDCl$_3$) δ 1.58–1.88 (8H,m,4×CH$_2$), 3.07 (2H,t,CH$_2$), 3.82 (4H,s,OCH$_3$ & OH), 3.95 (2H,t,CH$_2$), 4.17 (2H,s,CH$_2$), 4.76 (1H,m,CH), 6.33–6.89 (3H,m,ArH), 7.16 (1H,s,ArH), 7.52 (1H,s,ArH).

EXAMPLE 28

2-(3-Cyclopentyloxy-4-methoxybenzyl)-5-chloro-7-(2-hydroxyethyl)benzoxazole Carbamate A suspension of 2-(3-cyclopentyloxy-4-methoxybenzyl)-5-chloro-7-(2-hydroxyethyl)benzoxazole (0.6 g, 0.0015 mol) and sodium cyanate (0.2 g, 0.0030 mol) was stirred in 4 ml of CH$_2$Cl$_2$ and then trifluoroacetic acid (0.34 g, 0.0030 mol) was added. The mixture was stirred overnight as the initial solid dissolved and a new solid began to form. The next day CH$_2$Cl$_2$ (50 ml) and water (50 ml) were added. The water layer was separated and extracted with 2×50 ml of CH$_2$Cl$_2$. The combined CH$_2$Cl$_2$ layers were washed with 50 ml of water, dried and evaporated to give 0.6 g of white crystalline solid. This material was recrystallized from 6 ml of toluene to give 0.3 g of title compound as white crystals, mp 97–98° C.

$^1$H NMR (300 MHz, CDCl$_3$) δ 1.59–1.88 (8H,m,4×CH$_2$), 3.13 (2H,t,CH$_2$), 3.82 (3H,s,OCH$_3$), 4.18 (2H,s,CH$_2$), 4.36 (2H,t,CH$_2$), 4.45 (2H,bs,NH$_2$), 4.77 (1H,m,CH), 6.85–6.90 (3H,m,ArH), 7.13 (1H,d,ArH), 7.54 (1H,d,ArH).

EXAMPLE 29

2-(3-Cyclopentyloxy-4-methoxybenzyl)-5-chlorobenzoxazole-7-acetic Acid

A solution of 2-(3-cyclopentyloxy-4-methoxybenzyl)-5-chlorobenzoxazole-7-ethanal (2.0 g, 0.005 mol) in 50 ml of acetone was treated with 20 ml of 1 N Jones reagent and stirred for 1 hour at room temperature. Excess Jones reagent was destroyed by the addition of 50 ml of 2-propanol and the low boiling solvents were stripped under reduced pressure. Water (50 ml) and saturated sodium chloride (50 ml) were added and the aqueous residue was extracted with 2×75 ml of ethyl acetate. After drying, the ethyl acetate was evaporated to give 2.1 g of a brown foam. Solution of this material in CH$_2$Cl$_2$ and flash chromatography on silica gel afforded 0.72 g of the title acid as a yellow foam after elution with 500 ml of 0.5% CH$_3$OH in CH$_2$Cl$_2$. The foam was dissolved in 3 ml of CH$_3$OH and allowed to crystallize for 1 hour at freezer temperatures. After filtration, a total of 0.27 g of yellow title compound, mp 131–133° C., was isolated.

$^1$H NMR(300 MHz, CDCl$_3$) δ 1.58–1.87 (8H,m,4×CH$_2$), 3.81 (3H,s,OCH$_3$), 3.87 (2H,s,CH$_2$), 4.18 (2H,s,CH$_2$), 4.76 (1H,m,CH), 6.82–6.88 (3H,m,ArH), 7.23 (1H,s,ArH), 7.59 (1H,s,ArH).

EXAMPLE 30

2-(3-Cyclopentyloxy-4-methoxybenzyl)-5-chlorobenzoxazole-7-acetamide

A solution of 1,1'-carbonyl diimidazole (0.31 g, 0.0019 mol) was dissolved in 15 ml of tetrahydrofuran and 2-(3-cyclopentyloxy-4-methoxybenzyl)-5-chlorobenzoxazole-7-acetic acid (1.14 g, 0.0027 mol) was added in a tetrahydrofuran (THF) solution. After stirring for 1 hour, the reaction mixture was treated with 2 ml of concentrated NH$_4$OH and stirred a further 3.5 hours. The tetrahydrofuran was removed under reduced pressure and the remaining material was extracted with CH$_2$Cl$_2$. The organic layer was separated and washed with 50 ml of CH$_2$Cl$_2$. A crystalline solid (0.6 g) was isolated after drying and evaporating the CH$_2$Cl$_2$. The solid was recrystallized from 20 ml of CH$_3$OH to yield 0.3 g of title compound, mp 162–164° C.

$^1$H NMR (300 MHz, CDCl$_3$) δ 1.58–1.88 (8H,m,4×CH$_2$), 3.77 (2H,s,CH$_2$), 3.82 (3H,s,OCH$_3$), 4.18 (2H,s,CH$_2$) 4.76 (1H,m,CH) 5.45 (2H,bd,NH$_2$) 6.84–6.89 (3H,m,ArH) 7.23 (1H,s,ArH) 7.60 (1H,s,ArH).

EXAMPLE 31

2-(3-cyclopentyloxy-4-methoxybenzyl)-5-chlorobenzoxazole-7-ethanal Oxime

A suspension of 2-(3-cyclopentyloxy-4-methoxybenzyl)-5-chloro-7-ethanal oxime (0.60 g, 0.0015 mol), sodium cyanate(0.19 g, 0.003 mol) and 5 ml of $CH_2Cl_2$, was stirred at room temperature as trifluoroacetic acid (0.34 g, 0.003 mol) was added. The last traces of trifluoroacetic acid were rinsed into the reaction flask with 1 ml of $CH_2Cl_2$ and the reaction was stirred overnight. The next day 50 ml of water and 50 ml of $CH_2Cl_2$ were added and the $CH_2Cl_2$ layer was separated. The aqueous layer was extracted with 2×50 ml of $CH_2Cl_2$ and discarded. The combined $CH_2Cl_2$ layers were washed with 50 ml of water, dried and evaporated to give 0.80 g of yellow solid. This material was purified by flash chromatography over silica gel and upon elution with 1–5%. $CH_3OH$ in $CH_2Cl_2$, 0.5 g of the title compound was obtained. After recrystallization from 5 ml of ethyl acetate, 0.15 g of title compound, mp 161–162° C. was isolated.

$^1H$ NMR(300 MHz, $CDCl_3$) δ 1.50–1.90 (8H, m), 3.30 (1H, m), 3.80 (3H, d), 4.10 (2H, m), 4.30 (1H, m), 5–6.1 (m, 3 h), 6.7–7.5 (m, 6H).

EXAMPLE 32

2-(3-Chlorobenzoyl-7-aminobenzoxazole (a) N-(3-Chlorobenzoyl)-2-hydroxy-3-nitroaniline A stirred solution of 1,1'-carbonyl diimidazole (1.11 g, 0.0068 mol) in 20 ml of tetrahydrofuran was treated with 3-chlorobenizoic acid (1.02 g, 0.0065 mol). After stirring for 1 hour, 2-hydroxy-3-nitroaniline (1.00 g, 0.0065 mol) was added and the reaction mix was allowed to stir overnight. The next day, water (100 ml) was added and the aqueous suspension was extracted with $CH_2Cl_2$(2×100 ml). The $CH_2Cl_2$ layers were separated, washed with 2×50 ml water, dried and evaporated to give 1.92 g of yellow solid. This material was recrystallized from 150 ml of methanol and dried to give 1.80 g of title compound.

$^1H$ NMR (60 MHz, $CDCl_3$) δ 6.44–7.48 (6H,m,ArH), 8.16 (1H,bs,NH or OH) 8.37 (1H,d,ArH), 9.00 (1H,bs,NH or OH).

(b) 2-(3-Chlorophenyl)-7-nitrobenzoxazole

A stirred suspension of N-(3-chlorobenzoyl)-2-hydroxy-3-nitroaniline (4.5 g, 0.0117 mol), p-toluenesulfonic acid (0.30 g) and 50 ml of diphenyl ether were heated at 190° C. for 1 hour. The dark reaction mixture was dissolved in 100 ml $CH_2Cl_2$ and washed with saturated sodium bicarbonate and then water. The $CH_2Cl_2$ was evaporated and hexane was added, causing a brown solid to separate. The dark solid was filtered, dissolved in 75% $CH_2Cl_2$ in hexane and washed onto a silica gel column. Elution with this solvent, gave 3.3 g of the title compound. This material could be recrystallized from methanol to give 2-(3-chlorophenyl)-7-nitrobenzoxazole although it was pure enough from the chromatography to use for the next step without any further purification.

$^1HMR$ (60 MHz, $CDCl_3$) δ 6.59–7.63 (7H,m,ArH).

(c) 2-(3-Chlorophenyl)-7-aminobenzoxazole

A suspension of 2-(3-chlorophenyl)-7-nitrobenzoxazole (3.3 g, 0.012 mol) and 5 g of a 50% dispersion of Raney nickel in 130 ml of ethanol, was heated to 50° C. on a steam bath. The reaction temperature was held at 50° C. as a blend of 23 ml anhydrous hydrazine, 15 ml water and 20 ml of ethanol was added (30 minutes). The steam bath was removed and the reaction mixture was stirred at room temperature for 2.5 hours. The Raney nickel was removed by filtration through celite and the aqueous ethanol solution was concentrated on a rotary evaporator under reduced pressure. Water (100 ml) and $CH_2Cl_2$ (150 ml) were added to the residue and the $CH_2Cl_2$ layer was separated. The aqueous layer was extracted with 150 ml of $CH_2Cl_2$ and the combined $CH_2Cl_2$ layers were washed with 2×100 ml of water, dried and evaporated to give 2.90 g of yellow solid. This material was dissolved in 300 ml ethanol and filtered. The filtrate was concentrated to 100 ml and allowed to crystallize at freezer temperatures, to give the title compound as an off-white solid, mp 143–144° C., (1.97 g). A further 0.42 g of the title compound was obtained by evaporation of the mother liquor from the recrystallization and flash chromatography on silica gel using a 50:50 blend of $CH_2Cl_2$ in hexane as the eluent.

$^1H$ NMR (60 MHz, $CDCl_3$) δ 3.84 (2H,bs,$NH_2$), 6.23–7.78 (7H, m, ArH).

EXAMPLE 33

2-(3-chlorophenyl)-7-(2-pyridylmethylamino) benzoxazole

To a stirred suspension of 2-(3-chlorophenyl)-7-amino-benzoxazole (1.10 g, 0.0045 mol) in 10 ml of methanol, 2.5 ml of 1 N HCl in methanol, was added. 2-pyridinecarboxaldehyde(0.043 g, 0.0040 mol) was added to this suspension followed by sodium cyanoborohydride (0.32 g, 0.0051 mol) and the pH was adjusted to 6 using 1 N HCl in methanol. After 1 hour, 1 N sodium hydroxide was added to bring the pH to 10 and the reaction was extracted with 3×50 ml of ethyl acetate. The combined ethyl acetate extractions were washed with water, dried and evaporated to give 1.3 g of yellow solid. This solid was purified by flash chromatography over silica gel using 50:50 $CH_2Cl_2$ in hexane to give 0.25 g of recovered starting material, followed by 0.90 g of product when the eluting solvent was $CH_2Cl_2$. This solid was recrystallized from 100 ml of hexane to give 0.78 g of the title compound, mp 115–116° C.

$^1H$ NMR(60 MHz, $CDCl_3$) δ 4.34 (2H,s,$CH_2$) 4.90 (1H, bs,NH) 6.23 (1H,q,ArH) 6.70–7.70 (9H,m,ArH), 8.18 (1H, d,ArH).

EXAMPLE 34

2-(3-Cyclopentyloxy-4-methoxybenzyl)-7-(3-pyridylmethylamino)Benzoxazole

To a stirred suspension of 2-(3-cyclopentyloxy-4-methoxybenzyl)-7-aminobenzoxazole (0.98 g, 0.0029 mol) in 15 ml of methanol, 2.5 ml of 1 N HCl in methanol, was added. Pyridine-3-carboxaldehyde (0.37 g, 3.5 mmol) was added to this suspension followed by sodium cyanoborohydride (0.29 g, 0.0046 mol) and the pH was adjusted to 6 using 1 N HCl in methanol. After 3 hours, 1 N sodium hydroxide was added to bring the pH to 10 and the reaction mixture was extracted with $CH_2Cl_2$. The $CH_2Cl_2$ layer was separated and the aqueous layer was extracted with 2×50 ml of $CH_2Cl_2$. The combined $CH_2Cl_2$ layers were washed with water, dried and evaporated to give 1.09 g of yellow oil which crystallized on trituration with ether. After filtration, 0.5 g of white crystalline title compound was separated and the filtrate was concentrated. Flash chromatography of the filtrate on silica gel gave 0.2 g of recovered starting material on elution with $CH_2Cl_2$, followed by a further 0.32 g of crystalline title compound when the eluting solvent was 1% methanol in $CH_2Cl_2$. This material could be recrystallized from an ether-hexane blend to give the title compound as off-white crystals, mp 90–92° C.

$^1H$ NNMR (60 MHz, $CDCl_3$), δ 1.45–1.80 (8H, m, 4×$CH_2$), 3.53 (3 H, s, $OCH_3$), 3.84 (2 H, s, $CH_2$) 4.13 (2H, d, CH$_2$) 4.38 (1H, m, CH), 4.67 (1H, t, NH), 6.07 (1H, q, ArH), 6.33–6.74 (6H, m, ArH), 7.10(1H, q, ArH), 7.85 (1H, q, ArH) 8.01 (1H, d, ArH).

EXAMPLE 35

2-(3-Cyclopentyloxy-4-methoxybenzyl)-7-(2-imidazolylmethylamino)Benzoxazole

By employing a procedure similar to that in Example 33 and using 2-(3-cyclopentyloxy-4-methoxybenzyl)-7-aminobenzoxazole (1.3 g, 0.0038 mol), imidazole-2-carboxaldehyde (0.54 g, 0.0056 mol) and sodium cyanoborohydride (0.38 g, 0.0060 mol), a yellow oil was obtained after workup. The oil was triturated with a 50:50 blend of hexane in ether and the solid product (0.5 g) which was obtained, was separated by filtration. This solid could be recrystallized from ethanol (1 g/14 ml) to give the title compound as white crystals, mp 179–180° C.

$^1$NH NMR(60 MHz, CDCl$_3$ and d$_6$ DMSO) δ 1.45–1.90 (8H, m, 4×CH$_2$), 3.59 (3H, s, OCH$_3$), 3.93 (2H, s, CH$_2$), 4.30 (2H, bd, CH2), 4.50 (1H, m, CH), 4.84 (1H, bs, NH), 6.24 (1H, q, ArH), 6.43–6.72 (8H, m, ArH).

EXAMPLE 36

2-(3-Chlorophenyl)-7-(3-cyclopentyloxy-4-methoxy-benzylamino)Benzoxazole

By employing a procedure similar to that in Example 33 and using 2-(3-chlorophenyl)-7-aminobenzoxazole (1.00 g, 0.0041 mol), 3-cyclopentyloxy-4-methoxybenzaldehyde (1.08 g, 0.0049 mol), sodium cyanoborohydride (0.41 g, 0.0065 mol) and 35 ml of methanol, a white, crystalline solid was isolated. This crude product (1.4 g) was recrystallized from 200 ml of methanol to yield the title compound (1.1 g), mp 133–134° C.

$^1$H NMR (60 MHz, CDCl$_3$) δ 1.50–1.73 (8H,m,4×CH$_2$), 3.62 (3H,s,OCH$_3$), 4.13 (2H,s,CH$_2$), 4.48 (1H,m,CH), 6.15–7.73 (10H,m,ArH).

EXAMPLE 37

2-Benzyl-5-chloro-7-(3-hydroxy-1-propyl) Benzoxazole (a) N-phenylacetyl-2-hydroxy-5-chloroaniline Phenylacetic acid (20 g, 0.15 mol) in dichloromethane (120 ml) was treated with 1,1'-carbonyl diimidazole (25 g, 0.15 mol). After 1 hour, a solution of 2-hydroxy-5-chloroaniline in dichloromethane was added. The mixture was stirred overnight and processed in the usual manner to give 31.2 g of the title compound as a crystalline solid.

(b) N-phenylacetyl-2-allyloxy-5-chloroaniline

The N-phenylacetyl-2-hydroxy-5-chloroaniline (31.2 g, 0.12 mol) was converted to N-phenylacetyl-2-allyloxy-5-chloroaniline by treatment with allyl bromide (15.7 g, 0.13 mole) in N,N-dimethylacetamide (85 ml) in the presence of potassium carbonate (33.2 g, 0.24 mol) using the normal methods. The crude material was recrystallized from ethanol to give the title compound as a white solid (23.5 g, 65%).

(c) 2-Benzyl-5-chloro-7-allylbenzoxazole

The N-phenylacetyl-2-allyloxy-5-chloroaniline (23.5 g, 0.078 mol)obtained above was heated at 180° for 3 hours. The product was nearly pure title compound, suitable for the next step.

(d) 2-Benzyl-5-chloro-7-(3-hydroxy-1-propyl) Benzoxazole

A solution of 2-benzyl-5-chloro-7-allylbenzoxazole (2.2 g, 8 mmol) in THF (12 ml) was added to a solution of di-iso-amylborane (1.13 g, 8 mmol) in THF. The reaction was allowed to stir at room temperature for 21 hours and then 3 N sodium hydroxide solution (4 ml) was added followed by 30% hydrogen peroxide (4 ml). After 3 hours, the reaction mixture was partitioned between dichloromethane and water. The dichloromethane solution was washed with water (3×100 ml) and the solvent was evaporated under reduced pressure. The residue was purified over flash chromatographic silica gel to give the title compound (600 mg) eluted with 1:1 dichloromethane/hexane. The material was recrystallized three times from toluene to give the title compound (200 mg), trip 78–80° C.

$^1$H NMR (60 MHz, CDCl$_3$) δ 1.6–2.1 (m, 2H), 2.8 (t, J=8 Hz, 2H), 3.6 (t, J=6Hz, 2H), 4.15 (s, 2H), 7–7.5 (m, 7H).

EXAMPLE 38

2-(2-Chlorobenzyl)-5-chloro-7-allylbenzoxazole (a) N-((2-chlorophenyl)acetyl)-5-chloro-2-hydroxyaniline To a mixture of 1,1'-carbonyl diimidazole (66.5 g, 0.41 mol) and dichloromethane (300 ml) was added 2-chlorophenylacetic acid (67.0 g, 0.39 mol) dissolved in dichloromethane (200 ml). The mixture was stirred for 1.5 hours and 2-hydroxy-5-chloroaniline (56.4 g, 0.39 mol) was added in one portion. After stirring overnight, the reaction mixture was diluted with water and the mixture was filtered to give the desired amide. The dichloromethane was separated and washed with water. Evaporation of the dichloromethane under reduced pressure afforded additional product which was triturated with a small amount of dichloromethane and combined with the material collected previously to give 108.5 g of the title compound.

(b) N-(2-chlorophenylacetyl)-5-chloro-2-allyloxyaniline

N-(2-chlorophenylacetyl)-5-chloro-2-hydroxyaniline (107 g, 0.36 mol) was converted to N-(2-chlorophenylacetyl)-5-chloro-2-allyloxyaniline using allyl bromide in N,N-dimethylacetamide with potassium carbonate using previously described procedures. There was obtained 101.5 g of the title compound as white crystals after crystallization from methanol.

(c) 2-(2-Chlorobenzyl)-5-chloro-7-allylbenzoxazole

Pure N-(2-chlorophenylacetyl)-5-chloro-2-allyoxyaniline (100 g, 0.298 mol) was heated at 175–180° C. for 3.5 h to give 2-(2-chlorobenzyl)-7-allylbenzoxazole. The crude material was taken in 20% dichloromethane/hexane and filtered through a pad of flash chromatography silica gel (200 g) to give the pure title compound (73.9 g, 82%), mp 61–62° C. (from toluene).

$^1$H NMR (60 MHz, CDCl$_3$) δ 3.35 (d, J=8 Hz, 2H), 4.14 (s, 3H), 4.6–6 (m, 3H), 6.6–7.2(m, 6H)

EXAMPLE 39

2-(2-Chlorobenzyl)-5-chloro-7-(3-methoxy-1-propyl)Benzoxazole (a) 2-(2-Chlorobenzyl)-5-chloro-7-(3-hydroxy-1-propyl)Benzoxazole A solution of 2-(2-chlorobenzyl)-5-chloro-7-allylbenzoxazole (40 g, 0.126 mol) in THF (63 ml) was added to a solution at 0° C. of di-iso-amylborane prepared in THF from 10.8 g of borane-tetrahydrofuran complex and 19.5 g of 2-methyl-2-butene. The reaction mixture was allowed to warm to room temperature. After 16 hours, the reaction mixture was cooled to 5° C. and 3 N sodium hydroxide (50 ml) was added slowly followed by the slow addition of 30% hydrogen peroxide (50 ml). After 3 hours, the reaction mixture was diluted with dichloromethane (300 ml) and water (300 ml). The layers were separated and the aqueous solution was extracted with dichloromethane (2×150 ml). The dichloromethane extracts were combined and washed with water (3×200 ml) and evaporated under reduced pressure to give an oil. The crude product was purified by flash chromatography (silica gel; 300 g). Elution with 2 l of 1:1 hexane/dichloro-methane gave starting material (3.5 g). Elution with dichloromethane (5 l) afforded 32 g of the title compound, mp 87–89° C. (from toluene).

$^1$HNMR (CDCl$_3$, 60 MHz) δ 1.8–2.2 (m, 3H), 2.90 (t, J=8 Hz), 3.55 (t, J=6Hz, 2H), 4.35 (s, 2H), 7.0–7.4 (m, 6H).

(b) 2-(2-Chlorobenzyl)-7-(3-methanesulfonyloxy-1-propyl)-benzoxazole

A solution of 2-(2-chlorobenzyl)-7-(3-hydroxy-1-propyl) benzoxazole (10 g, 0.033 mole) in ether (50 ml) was treated with methanesulfonyl chloride (4.4 g, 0.037 mol) and tri-ethylamine 3.7 g, 0.037 mol). After stirring for 1 hour, the triethylamine hydrochloride was filtered and the ether was evaporated to give the title compound which was pure by TLC.

(c) 2-(2-Chlorobenzyl)-5-chloro-7-(3-methoxy-1-propyl)Benzoxazole 2-(2-Chlorobenzyl)-5-chloro-7-(3-methanesulfonyloxy-1-propyl)-benzoxazole was stirred overnight with a solution of sodium methoxide prepared from methanol (100 ml) and sodium (2.7 g, 0.118 mol). The reaction mixture was diluted with water and extracted with dichloromethane. The dichloromethane solution was washed with water and evaporated to give the crude product (10 g). The crude product was purified over flash chromatography silica gel and eluted with 30% dichloromethane/hexane. The effluent was collected in 200 ml fractions. Fractions 1–7 contained an impurity (7.1 g); fractions 8–11 were collected (1.8 g) and recrystallized three times from hexane to give the title compound (0.4 g), mp 49–51°.

$^1$NH NMR(CDCl$_3$, 60 MHz) δ 2.0 (m, 2H), 2.85 (t, J=8 Hz, 2H), 3.20–3.50 (m, 5H), 4.4 (s, 2H), 7.0–7.5 (m, 6H).

EXAMPLE 40

2-(3-Cyclopentyloxy-4-methoxybenzyl)-5-chloro-7-propylbenzoxazole

A solution of 2-(3-cyclopentyloxy-4-methoxybenzyl)-5-chloro-7-allylbenzoxazole (1.2 g, 3.0 mmol) in ethyl acetate (50 ml) was hydrogenated over 0.104 g of 10% Pd on carbon catalyst in a Parr apparatus at 23 psi until hydrogen uptake ceased. The catalyst was filtered and the solvent was evaporated. The residue was recrystallized from hexane to give the title compound (0.55 g, 46%), mp 54–55° C.

$^1$H NMR (60 MHz, CDCl$_3$) δ 0.95 (t, J=8 Hz, 3H) 1.6–1.9 (m, 10H) 2.8(t, J=7 Hz) 3.6 (s, 3H), 4.0 (s, 2H), 4.4–4.6 (m, 1H) 6.4–7 (m, 6H).

EXAMPLE 41

2-(2-Chlorobenzyl)-7-(3-hydroxy-1-propyl) Benzoxazole (a) N-(2-Chlorophenylacetyl)-2-hydroxyaniline To a mixture of 1,1'-carbonyl diimidazole (12.45 g, 0.077 mol) and dichloromethane (50 ml) was added 2-chlorophenylacetic acid (12.5 g, 0.073 mol) in portions. The mixture was stirred for 1 h and 2-hydroxyaniline (7.99 g, 0.073 mol) was added in one portion. After stirring overnight, the reaction mixture was diluted with water and filtered to give the title compound (18.3 g after drying).

(b) N-(2-chlorophenylacetyl)-2-alloxyaniline

N-(2-chlorophenylacetyl)-2-hydroxyaniline (18.3 g, 0.07 mol) was converted to N-(2-chlorophenyl-acetyl)-2-allyloxyaniline using allyl bromide in N,N-dimethylacetamide with potassium carbonate using previously described conditions. The title compound was obtained as a white crystalline solid (7.5 g) after crystallization from methanol.

(c) 2-(2-Chlorobenzyl)-7-allylbenzoxazole

N-(2-chlorophenylacetyl)-2-hydroxyaniline (7.5 g), was heated at 180° for 6 h and then at 220° for 4 hours to give the title compound as a viscous oil which was pure enough for the next step.

(d) 2-(2-Chlorobenzyl)-7-(3-hydroxy-1-propyl) Benzoxazole

A solution of 2-(2-chlorobenzyl)-5-chloro-7-allylbenzoxazole (5.0 g, 0.018 mole) in THF was added to a solution of di-iso-amylborane prepared from borane-THF complex (1.60g, 0.018 mol) and 2-methyl-2-butene (2.80 g, 0.04 mol) in THF. The reaction mixture was stirred overnight and cooled to −20° C. then treated with 3 N sodium hydroxide (6.5 ml) and 30% hydrogen peroxide (6.5 ml). The reaction mixture was allowed to warm to room temperature and stirred for 4 hours. The product was isolated by partitioning between dichloromethane and water. Flash chromatography over flash chromatographic silica gel with dichloromethane afforded nearly pure title compound which was recrystallized from ether-hexane to give 290 mg of pure title compound, mp 66–68° C.

$^1$H NMR(CDCl$_3$, 60 MHz) δ 1.7–2.2 (m, 3H), 3.0 (t, J=8 Hz, 2H), 3.70 (t, J=6 Hz, 2H), 4.40 (s, 2H), 7.05–7.60 (m, 6H).

EXAMPLE 42

3-[5-Chloro-2-(3-chlorobenzyl)benzoxazol-7-yl] propan-1-ol (a) N-(3-chlorophenylacetyl)-2-hydroxy-3-bromo-5-chloroaniline Using the normal amide forming conditions, the condensation of 3-chlorophenylacetic acid (13.54 g, 0.079 mol) and 2-hydroxy-3-bromo-5-chloroaniline (17.7 g, 0.079 mol) with 1,1'-carbonyl diimidazole (13.5 g, 0.083 mol) gave the title compound (20 g).

(b) 2-(3-Chlorophenyl)-5-chloro-7-bromobenzoxazole

The amide from Step (a) was heated at 175° under nitrogen for 4 hours. The crude product was purified by flash chromatography (SiO$_2$; 80 g). Elution with 400 ml of 1:1 dichloromethane/hexane gave a small amount of impurity. Continued elution with the same solvent gave 15.4 g of the title compound as a white solid.

(c) 3-[2-(3-Chlorophenyl)-5-chlorobenzoxazol-7-yl] Propargyl Alcohol

The reaction was carried out under nitrogen with strict exclusion of air. All solutions were degassed with a nitrogen stream. A solution of 2-(3-chlorobenzyl)-5-chloro-7-bromo-benzoxazole (41.0 g, 0.019 mol) in diethylamine (328 ml) and bis(triphenylphosphine)palladium(II) chloride (1.53 g, 2.1 mmol) was treated with propargyloxytrimethylsilane (27.9 g, 0.218 mol). The reaction mixture was heated to 55–60°. After 3 hours, additional propargyloxytrimethylsilane (3 g, 0.023 mol) was added and after a further 2.5 hours, another portion of propargyloxytrimethylsilane (5 g, 0.039 mol) was added. The reaction was continued 30 min and cooled. The diethylamine hydrobromide was removed by filtration and the diethylamine was evaporated under reduced pressure. The residue was taken up in dichloromethane (250 ml) and washed with water (2×200 ml). The solvent was evaporated and the residue was dissolved in methanol (500 ml) and cooled to 5° C. Potassium carbonate (17g, 0.123 mol) and water (10 ml) were added and the reaction mixture was stirred for 30 minutes. The methanol was evaporated under reduced pressure and the residue was taken up in dichloromethane (500 ml) and washed with water. The dichloromethane was evaporated under reduced pressure and the crude product was purified over flash chromatography silica gel (310 g). Elution with 800 ml of dichloromethane afforded 2 g of mixed material. Continued elution with dichloromethane (5.5 1) gave 31 g (81%) of the title compound which was recrystallized from acetone to give 18 g of pure crystalline title compound.

(d) 3-[5-Chloro-2-(3-chlorobenzyl)benzoxazol-7-yl] propan-1-ol

A solution of 3-[5-chloro-2-(3-chlorobenzyl)benzoxazol-7-yl]propargyl alcohol (19.8 g, 0.0596 mole) in ethyl acetate (500 ml) was hydrogenated with 5% Rh on alumina catalyst at an initial pressure of 20 psi in a Parr apparatus. After the theoretical amount of hydrogen had been absorbed, the catalyst was filtered and the solvent was removed under reduced pressure. The crude material was triturated with hexane and crystallized from toluene to give pure title compound (10 g, 55%), mp 87–89° C.

$^1$NH NMR(300 MHz, CDCl$_3$) δ 1.75 (t, 1H), 2.0 (m, 2H), 2.95 (m, 2H), 3.85 (m, 2H), 4.10 (s, 2H), 7.1–7.6 (m, 6H).

EXAMPLE 43

5-Chloro-2-[2-(3,4-dimethoxyphenyl)ethyl] Benzoxazole (a) N-[3-(3,4-dimethoxyphenyl)propanoyl]-2-hydroxy-5-chloroaniline Using similar procedures with 3-(3,4-dimethoxyphenyl)-propanoic acid (2.10 g, 10 mmol), 2-hydroxy-5-chloroaniline (1.45 g, 10 mmol) and 1,1'-carbonyl diimidazole (1.62 g, 10 mmol) there was obtained 2.3 g of the title compound as an oil suitable for the next step.

(b) 5-Chloro-2-[2-(3,4-dimethoxyphenyl)ethyl] Benzoxazole

N-[3-(3,4-dimethoxyphenyl)propanoyl-2-hydroxy-5-chloro-aniline (2.3 g, 6.3 mmol) in toluene (30 ml) and p-toluenesulfonic acid monohydrate (0.3 g, 1.5 mmol) was heated under reflux for 3 hours. The cooled reaction mixture was decanted from some tar and the toluene was evaporated. The residue was crystallized from t-butyl methyl ether with charcoal to give 1.3 g of the title compound which was recrystallized from t-butyl methyl ether to give pure title compound (1.08 g) mp 102–105° C.

$^1$H NMR (300 MHz, CDCl$_3$) δ 3.4 (m, 4H), 3.85 (s, 3H), 3.9 (s, 3H), 6.6–7.7 (m, 6H).

EXAMPLE 44

5-Chloro-2-(3,4-dimethoxyphenyl)Benzoxazole (a) N-(3,4-dimethoxybenzoyl)-2-hydroxy-5-chloroaniline Using similar procedures with 3,4-dimethoxybenzoic acid (5.46 g, 3 mmol), 2-hydroxy-5-chloroaniline (4.31 g, 3 mmol) and 1,1'-carbonyl diimidazole (4.86 g, 3 mmol) there was obtained 10.8 g of the title compound as a white solid.

(b) 5-Chloro-2-(3,4-dimethoxyphenyl)Benzoxazole

A solution of N-(3,4-dimethoxybenzoyl)-2-hydroxy-5-chloroaniline (5.0 g, 0.015 mol) was heated under reflux for 11 hours in 30 ml o-dichlorobenzene and p-toluenesulfonic acid monohydrate (0.3 g, 15 mmol). The reaction mixture was diluted with dichloromethane and filtered through a pad of alumina (25 g). The solvent was evaporated under reduced pressure and the residue was triturated with petroleum ether and filtered to give 2.7 g of crudeproduct. The material was crystallized from methyl t-butyl ether with charcoal to give 1.35 g of material which was crystallized again from methyl t-butyl ether and sublimed at 130° C. (0.05 mm) to give pure title compound as tan crystals, mp 142–145° C.

$^1$NH NMR(300 MHz, CDCl$_3$) δ 4.05 (s, 3H), 4.10 (s, 3H), 7.0–8.0 (m, 6H).

EXAMPLE 45

2-[4-Hydroxy-3,5-di-t-butyl-benzyl]Benzoxazole (a) N-[4-hydroxy-3,5-di-t-butyl-phenylacetyl]-2-hydroxyaniline Using previously described procedures with 4-hydroxy-3,5-di-t-butyl-phenylacetic acid (45 g, 0.17 mol), 2-hydroxyaniline (20.7 g, 0.19 mol) and 1,1'-carbonyl diimidazole (29 g, 0.18 mol) the title compound (52.1 g, 86%) was obtained as a tan solid.

(b) 2-[4-Hydroxy-3,5-di-t-butyl-benzyl]-benzoxazole

A sample of N-[4-hydroxy-3,5-di-t-butyl-phenyl-acetyl]-2-hydroxyaniline (12.0 g, 0.033 mol) was heated at 260° under nitrogen for 50 minutes. After cooling, the material was heated at reflux with hexane (50 ml) until most of the sample was dissolved. The mixture was filtered while hot and allowed to cool. Filtration afforded 5.4 g (49%) of nearly pure title compound. Pure title compound was obtained after two further crystallizations (with charcoal) from hexane, mp 94–96° C.

$^1$H NMR (60 MHz, CDCl$_3$) δ 1.55 (s, 18H), 4.2 (s, 2H), 5.2 (s, 1H), 7.0–7.6 (m, 6H).

EXAMPLE 46

2-[4-Hydroxy-3,5-di-t-butyl-benzyl]-4-carbomethoxybenzoxazole (a) N-[4-hydroxy-3,5-di-t-butyl -phenylacetyl]-2-hydroxy-6-carbomethoxyaniline After a solution of 1,1'-carbonyl diimidazole (2.90 g, 0.018 mol), 4-hydroxy-3,5-di-t-butyl-phenylacetic acid (4.96 g, 0.019 mol) and 50 ml of dichloromethane was stirred at room temperature for 1.5 hours, 2-hydroxyaniline (3.00 g, 0.018 mol) dissolved in 50 ml of dichloromethane, was added. The reaction blend was stirred overnight. The next day, 50 ml of water was added and the layers were separated. The organic layer was washed with 3×60 ml of 2% sulfuric acid, dried and evaporated to give a yellow solid. This material was recrystallized from t-butyl methyl ether to give 4.6 g of N-[4-hydroxy-3,5-di-t-butyl-phenylacetyl]-2-hydroxy-6-carbomethoxyaniline.

(b) 2-[4-Hydroxy-3,5-t-butyl-benzyl]-4-carbomethoxybenzoxazole

A sample of N-[4-hydroxy-3,5-di-t-butyl-phenylacetyl]-2-hydroxy-6-carbomethoxyaniline (3.50 g, 0.0084 mol) was heated at 170° C. under a nitrogen atmosphere for 22 hours. The residue was dissolved in 50 ml of isopropyl alcohol and then approximately 10 ml of water was added and the solution was allowed to crystallize. A total of 2.20 g of title compound, mp 143–147° C., was obtained as yellow crystals.

$^1$NH NMR(60 MHz, CDCl$_3$) δ 1.35 (18H, s, t-butyl),3.78 (3H, s, CH$_3$), 3.99 (2H, s, CH$_2$), 4.78 (1H, s, OH), 6.68–7.45 (5H, m, ArH).

EXAMPLE 47

2-[2-(4-Hydroxy-3,5-di-t-butyl-phenyl)] Ethylbenzoxazole (a) N-[3-(4-hydroxy-3,5-di-t-butyl-phenyl) propanoyl]-2-hydroxyaniline The title compound was obtained from 3-[4-hydroxy-3,5-t-butyl-phenyl]propanoic acid (5.56 g, 0.02 mol), 2-hydroxyanilinie (2.4 g, 0.022 mol) and 1,1'-carbonyl diimidazole (3.4 g, 0.021 mol) using the normal procedures. The crude product was recrystallized from cyclohexane-ethyl acetate to give 5.50 g.(75%) of the title compound as white crystals.

(b) 2-[2-(4-Hydroxy-3,5-di-t-butyl-phenyl)]Ethyl-benzoxazole

N-[3-(4-hydroxy-3,5-di-t-butyl-propanoyl]-2-hydroxyaniline (0.96 g. 2.6 mmol) was heated at 280° for 8 min and cooled. The material was triturated with petroleum ether to give the title compound (0.70 g, 72%) as white crystals, mp 103–106° C.

$^1$H NMR (60 MHz, CDCl$_3$) δ 1.4 (s, 18 H), 3.2 (bs, 4H) 5.1 (bs, 1H) 7.0–7.7 (m, 6H).

EXAMPLE 48

Following the procedures set forth in Examples 11 and 12, the PDE III and PDE IV inhibition values for the compounds of Examples 25–47 were calculated. The results are shown the Table III below expressed as IC$_{50}$ values.

TABLE III

| | IC$_{50}$(μM) | |
|---|---|---|
| EXAMPLE | PDE III | PDE IV |
| 25 | 118.24 | 0.65 |
| 26 | 11.41 | 0.37 |
| 27 | 38.14 | 0.65 |
| 28 | 36.75 | 0.70 |
| 29 | 100 | 11.22 |
| 30 | 128.36 | 2.92 |

TABLE III-continued

| | IC$_{50}$(μM) | |
|---|---|---|
| EXAMPLE | PDE III | PDE IV |
| 31 | >300 | 1.66 |
| 32 | >300 | 32.50 |
| 33 | 173.2 | 9.10 |
| 34 | 33.2 | 1.00 |
| 35 | >300 | 19.30 |
| 36 | >300 | 15.80 |
| 37 | 77.0 | 39.10 |
| 38 | 107.0 | 5.40 |
| 39 | 53.9 | 15.20 |
| 40 | >300 | 0.92 |
| 41 | 100.0 | 69.30 |
| 42 | 48.6 | 16.00 |
| 43 | >300 | 16.28 |
| 44 | >300 | 19.31 |
| 45 | 72.4 | 19.51 |
| 46 | 701.8 | 21.50 |
| 47 | >300 | 91.53 |

As can be seen from the foregoing, the inventive compounds provide high levels of PDE IV inhibition while at the same time relatively low levels of PDE-III inhibition. In all cases, the PDE IV IC$_{50}$ values were below that of theophylline and less than the PDE III IC$_{50}$ values.

EXAMPLE 49

5-Chloro-2-(2-chlorophenyl)-benzoxazole-7-(N-hydroxy-N-methyl-propanamide (a) 5-Chloro-2-(2-chlorophenyl)-7-(3-hydroxy-1-propynyl)-benzoxazole A solution of 17.15 g (50 mmol) of 7-bromo-5-chloro-2-(2-chlorophenyl)-benzoxazole and 4.40 ml (75 mmol) of propargylalcohol in 32 ml of toluene and 64 ml of triethylamine was heated under nitrogen to 80–5° C. with 175.4 mg (250 μM) of bis(triphenylphosphine)palladium (II) chloride and 8.6 mg (4.5 μM) of copper (1) iodide. After 6 hours, the solid was filtered off and washed with dichloromethane. The solution was evaporated in vacuo. The residue was dissolved in ethyl acetate, washed with 1 N HCl, sodium bicarbonate solution, and water. The ethyl acetate was removed in vacuo, the residue (15.46 g) was dissolved in dichloromethane and filtered through 60 g of silica gel to give the title compound (13.64 g, 85.8%), mp 165–9° C.

(b) 5-Chloro-2-(2-chlorophenyl)-7-(3-hydroxy-propyl)-benzoxazole

A suspension of 11.07 g (34.8 mmol) of 5-chloro-2-(2-chlorophenyl)-7-(3-hydroxy-1-propynyl)-benzoxazole in 120 ml of ethyl acetate was treated with 3.70 g of neutral Raney-nickel. After the hydrogen uptake ceased, the nickel was filtered off and washed, and the solution evaporated in vacuo. Crystallization from dichloromethane/di-isopropyl ether gave the title compound in two crops (6.12 g (54.6%) and 1.61 g (14.4%)), mp 82–4° C.

Elemental analysis for C$_{16}$H$_{13}$C$_{12}$NO$_2$;

| | | | | |
|---|---|---|---|---|
| calc | C 59.65 | H 4.07 | N 4.35 | O 9.93 |
| found | C 59.81 | H 4.02 | N 4.35 | O 10.12 |

(c) 5-Chloro-2-(2-chlorophenyl)-benzoxazole-7-propanoic Acid 10.3 ml (41 mmol of O) of Kiliani solution was added at −10° to −5° C. within 20 minutes to a solution of 6.44 g (20 mmol) of 5-chloro-2-(2-chlorophenyl)-7-(3-hydroxypropyl)-benzoxazole in 130 mg of acetone. After 45 minutes, 5 ml of methanol and 130 ml of water were added. The acetone was removed in vacuo, the solid suspended, collected, and washed with 1 N sulfuric acid and water. The residue was taken up in 35 ml of 1 N NaOH and 50 ml of water, and extracted with ether. The water phase was acidified with 5 N HCl to pH 3. Filtration and washing gave the title compound (4.88 g, 72.6%), mp 152–4° C.

(d) 5-Chloro-2-(2-chlorophenyl)-benzoxazole-7-(N-hydroxy-N-methyl-propanamide 1.68 g (5 mmol) of 5-chloro-2-(2-chlorophenyl)-benzoxazole-7-propanoic acid were refluxed for 30 minutes in 15 ml of dichloromethane containing 0.9 ml (12.5 mmol) of thionyl chloride. The solvents were evaporated in vacuo and again after toluene addition. The acid chloride was dissolve in 20 ml of THF and added at –10° C. to a prepared (45 minutes) suspension of 2.09 g (25 mmol) of N-methylhydroxylamine, 6.93 ml (50 mmol) of triethylamine and 0.53 g (5 mmol) of sodium carbonate in 50 mg of dry THF. After 1 hour, the remaining solid was filtered off and washed with THF. The solvents were evaporated in vacuo and the residue suspended in 150 ml of ether, the solid filtered off and the ether evaporated. The residue was taken up in acetone filtered again and evaporated. This residue was suspended in little ether and collected to give the title compound (1.25 g, 68.7%) of hydroxyamide with mp 146–8° C.

Elemental analysis for $C_{17}H_{14}C_{12}N_2O_3$;

| calc | C 55.91 | H 3.86 | N 7.67 | O 13.14 |
|---|---|---|---|---|
| found | C 56.34 | H 3.69 | N 7.71 | O 13.22 |

EXAMPLE 50

5-Chloro-2-(2-chlorophenyl)-7-[3-(N'-hydroxycarbamido)butyl]-benzoxazole (a) 5-Chloro-2-(2-chlorophenyl)-7-(3-oximidobutyl)-benzoxazole At 16–20° C., a solution of 4.48 g (13.4 mmol) of 4-(5-chloro-2-(2-chlorophenyl)benzoxazol-7-yl)butan-2-one in 50 ml of THF and 50 ml of 94% ethanol was added within 10 minutes to a solution of 1.02 g (14.7 mmol) of hydroxy-ammonium chloride and 1.82 g (13.4 mmol) of sodium acetate trihydrate in 9.8 ml of water. A precipitate formed at the beginning, which dissolved again, and formed a new precipitate after about half of the addition. After 2 hours, water was added and the organic solvent was evaporated in vacuo. The solid was collected, washed, and dried to give the crude title compound (4.71 g, 100.6%) as an E/Z mixture.

(b) 5-Chloro-2-(2-chlorophenyl)-7-[3-(N'-hydroxycarbamido)butyl]-benzoxazole 0.40 g (5.6 mmol) of borane trimethylamine complex was added to a solution of 0.48 g (1.4 mmol) of oxime in 8.9 ml of THF, followed by the addition of 2.24 ml of 5 N HCl within 25 minutes. After 40 minutes, a second batch of 0.40 g of borane trimethylamine complex was added. After a further 1 hour, the solution was adjusted to pH 8 with sodium bicarbonate solution and the THF was removed in vacuo. The aqueous residue was extracted with dichloromethane and the extract evaporated to dryness: 0.67 g (100%) of crude product, which was dissolved in 6.6 ml of THF, treated with 0.23 ml (1.68 mmol) of trimethylsilyl isocyanate (96%) and heated at reflux for 3.25 hours. The solvent was removed in vacuo, the residue treated with 30 ml of 10% ammonium chloride and extracted with ether. The residue of the extract was crystallized from dichloromethane to give 0.16 g (29.1%) of the title compound, mp 130–45° C.

EXAMPLE 51

By using a similar procedure to Example 4, employing the corresponding acid chloride and 6-amine-2-bromo-4-chloro-phenol, the following 7-bromo-5-chloro-2-substituted-benzoxazoles were obtained:

(a) 2-(2-chlorophenyl), mp 156–8° C.
(b) 2-(3-cyclopentyloxy-4-methoxy-phenyl), mp 155–7° C.
(c) 2-(3,4-dimethoxyphenyl), mp 184–5° C.
(d) 2-benzyl, mp 81–3° C.
(e) 2-(2-chlorobenzyl), mp 89–90° C.
(f) 2-(4-chlorobenzyl), mp 212–4° C.
(g) 2-(2,4-dichlorobenzyl), mp 123–5° C.
(h) 2-(2,6-dichlorobenzyl), mp 180–1° C.
(i) 2-(2-chloro-6-fluoro-benzyl), mp 133–4° C.
(j) 2-(2-fluorobenzyl), mp 120–1° C.
(k) 2-(3-cyclopentyloxy-4-methoxy-cinnamenyl), mp 137–9° C.
(l) 2-[2-(2-chlorophenyl)ethyl], mp 78–80° C.
(m) 2-[2-(3,5-di-t-butyl-4-hydroxy-phenyl)ethyl], mp 120–1° C.
(n) 2-[2-(3-cyclopentyloxy-4-methoxy-phenyl)ethyl], mp 103–4° C. and with 2-aminophenol, the corresponding
(o) 2-(3,5-di-t-butyl-4-hydroxy-cinnamenyl)-benzoxazole, mp 130–1° C. was obtained.

EXAMPLE 52

By using a similar procedure to Example 49, step a, employing the appropriate 7-bromo-5-chloro-2-substituted-benzoxazole and propargyl alcohol, the following 5-chloro-7-(3-hydroxy-1-propynyl)-2-substituted-benzoxazoles were obtained:

(a) 2-(3-cyclopentyloxy-4-methoxy-phenyl), mp 162–3° C.
(b) 2-(3,4-dimethoxyphenyl), mp 192–6° C.
(c) 2-benzyl, mp 94–6° C.
(d) 2-(3-cyclopentyloxy-4-methoxy-benzyl), mp 147–8° C.
(e) 2-(3,5-di-t-butyl-4-hydroxy-benzyl), mp 143–7° C.
(f) 2-(3,4-dimethoxybenzyl), mp 147–8° C.
(g) 2-(2-chlorobenzyl), mp 113–4° C.
(h) 2-(4-chlorobenzyl), mp 96–9° C.
(i) 2-(2,4-dichlorobenzyl), mp 137–9° C.
(j) 2-(2,6-dichlorobenzyl), mp 150/160–2° C.
(k) 2-(2-chloro-6-fluoro-benzyl) mp 119–21° C.
(l) 2-(2-fluorobenzyl), mp 123–4° C.
(m) 2-(3-cyclopentyloxy-4-methoxy-cinnamenyl), mp 150–4° C.
(n) 2-[2-(2-chlorophenyl)ethyl], mp 91–2° C.
(o) 2-[2-(4-acetoxy-3,5-di-t-butyl-phenyl)ethyl], mp 138–9° C.

(p) 2-[2-(3-cyclopentyloxy-4-methoxy-phenyl)ethyl], mp 107–9° C.

EXAMPLE 53

By using a similar procedure to Example 49, step b, employing the appropriate 5-chloro-7-(3-hydroxy-1-propynyl)-2-substituted-benzoxazole, the following 5-chloro-7-(3-hydroxy-propyl)-2-substituted-benzoxazoles were obtained:
- (a) 2-(3,4-dimethoxyphenyl); mp 138–9° C.
- (b) 2-(3-cyclopentyloxy-4-methoxy-benzyl), mp 92–4° C.
- (c) 2-(3,5-di-t-butyl-4-hydroxy-benzyl), mp 136–8° C.
- (d) 2-(3,4-dimethoxy-benzyl), mp 90–2° C.
- (e) 2-(2-chlorobenzyl), mp 81–2° C.
- (f) 2-(4-chlorobenzyl), mp 78–9° C.
- (g) 2-(2,6-dichlorobenzyl), mp 105–8° C.
- (h) 2-(2,4-dichlorobenzyl), mp 86–7° C.
- (i) 2-(2-chloro-6-fluoro-benzyl), mp 99–100° C.
- (j) 2-(2-fluorobenzyl), mp 73–4° C.
- (k) 2-[2-(2-chlorophenyl)ethyl], mp 62–3° C.
- (l) 2-[2-(3-cyclopentyloxy-4-methoxy-phenyl)ethyl], mp 76–7° C.

EXAMPLE 54

By using a similar procedure to Example 49, step c, employing the appropriate 5-chloro-7-(3-hydroxy-propyl)-2-substituted-benzoxazole, the following 5-chloro-2-substituted-benzoxazole-7-propionic acids were obtained:
- (a) 2-(2-chlorobenzyl), mp 147–52° C.
- (b) 2-(2-chloro-6-fluoro-benzyl), mp 172–3° C.
- (c) 2-[2-(3-cyclopentyloxy-4-methoxy-phenyl)ethyl], mp 151–3° C.

EXAMPLE 55

By using a similar procedure to Example 49, step d, employing the appropriate the appropriate 5-chloro-2-substituted-benzoxazole-7-propionic acid and amine, the following amides were obtained:
- (a) 5-Chloro-2-(2-chlorobenzyl)-benzoxazole-7-propanamide, mp 181–3° C.
- (b) 5-Chloro-2-(2-fluorobenzyl)-benzoxazole-7-propanoic acid, N-morpholine amide, mp 99–101° C.

EXAMPLE 56

(a) 5-Chloro-2-(2-chlorophenyl)-7-(3-carbamido-1-propynyl)-benzoxazole

By using a similar procedure to Example 49, step a, employing N-propargylurea, we obtained the title compound was obtained in 71% yield with mp 268–72° C.

(b) 5-Chloro-2-(2-chlorophenyl)-7-(3-carbamido-propyl)-benzoxazole

By using a similar procedure to Example 49 step b, we obtained the title compound was obtained in 56.1% yield with mp 233–5° C.

EXAMPLE 57

By using a similar procedure to Example 2 f, employing the appropriate 5-chloro-7-bromo-2-substituted-benzoxazole, the following 5-chloro-7-ethynyl-2-substituted-benzoxazoles were obtained:
- (a) 2-(3,5-di-t-butyl-4-hydroxy-cinnamenyl), mp 188–91° C.
- (b) 2-[2-(3,5-di-t-butyl-4-hydroxy-phenyl)ethyl], mp 128–30° C.

EXAMPLE 58

By using a procedure similar to Example 2 g, employing the appropriate 5-chloro-7-ethynyl-2-substituted-benzoxazole, the following 5-chloro-7-(2-(2-pyridyl)ethynyl)-2-substituted-benzoxazoles was obtained:

(a) 2-(3,5-di-t-butyl-cinnamenyl), mp 169–71° C.

Hydrogenation according to Example 49, step b gave:

(b) 2-[2-(4-acetoxy-3,5-di-t-butyl-phenyl)ethyl]-5-chloro-7-[2-(2-pyridyl)ethyl]-benzoxazole, mp 134–5°

EXAMPLE 59

By using a procedure similar to that set forth in Example 3 and the 7-ethynyl compound:

(a) 5-chloro-2-(2-chlorobenzyl)-7-[2-(2-thiazolyl)ethynyl]-benzoxazole, mp 149–51° C. was prepared;

and by subsequent hydrogenation according to Example 49, step b, (b) 5-chloro-2-(2-chlorobenzyl-7-[2-(2-thiazolyl)ethyl]-benzoxazole, mp 64–6° C. was prepared.

EXAMPLE 60

By using a similar procedure to Example 49, step a, employing 7-bromo-5-chloro-2-(2-chlorobenzyl)-benzoxazole and 4-pentyn-1-ol the following compounds were prepared:

(a) 5-chloro-2-(2-chlorobenzyl)-7-(5-hydroxy-1-pentynyl)-benzoxazole, mp 96–7° C.

Elemental analysis for $C_{19}H_{15}ClNO_2$;

| | | | | | | | |
|---|---|---|---|---|---|---|---|
| calc | C 63.35 | H 4.20 | N 3.89 | O 8.88 |
| found | C 63.14 | H 3.96 | N 3.84 | O 9.08 |

(b) Hydrogenation according to Example 49, step b gave: 5-chloro-2-(2-chlorobenzyl)-7-(5-hydroxypentyl)-benzoxazole, mp 72–9° C.

EXAMPLE 61

2-(3,4-dimethoxybenzyl)-7-(3-hydroxy-propyl)-benzoxazole

A solution of 2.89 g (8.0 mmol) of 5-chloro-2-(3,4-dimethoxybenzyl)-7-(3-hydroxy-propyl)-benzoxazole in 50 ml of THF and 1.23 ml (8.8 mmol) of triethylamine and with 0.58 g of 10% Pd-C was hydrogenated in an autoclave at about 1100 psi. After 2.5 hour, the catalyst was filtered off and the solvents evaporated in vacuo. The residue was dissolved in dichloromethane and filtered through 6.3 g of silica gel in a column. The recovered material (2.53 g) was crystallized from di-isopropyl ether to give the title compound (1.36 g, 51.9%), mp 95–7° C. A second crop of 0.94 g (35.9%) was also obtained.

Elemental analysis for $C_{19}H_{21}NO_4$;

| calc. | C 69.71 | H 6.47 | N 4.28 | O 19.55 |
| found | C 69.83 | H 6.26 | N 4.44 | O 19.46 |

EXAMPLE 62

5-Chloro-2-(3-cyclopentyloxy-4-methoxy-phenyl)-7-[3-(N-t-butoxycarbonyl-N-hydroxy-amino)-1-propynyl]-benzoxazole (a) 5-Chloro-2-(3-cyclopentyloxy-4-methoxy-phenyl)-7-[3-(N-t-butyloxycarbonyl-N-t-butyloxycarbonyloxy-amino)-1-propynyl]-benzoxazole A solution of 1.24 ml (6.0 mmol) of di-isopropyl azodicarboxylate in 5 ml of THF was added at 0° C. to a suspension of 1.99 g (5.0 mmol) of benzoxazole-7-propargyl alcohol, t-butyl-N-(t-butoxycarbonyloxy) carbamate (97%, 1.32 g, 5.5 mmol), and 1.61 g (6.0 mmol) of triphenylphosphine (98%) in 20 ml of THF added within 5 minutes. After 1 hour, the solution was evaporated in vacuo, the residue dissolved in 25 ml of dichloromethane and purified by chromatography on 250 g of silicagel. The first 1.54 g (50.1%) were crystallized from diisopropyl ether to give the title compound (1.07 g, 34.9%), mp 144–6° C.

(b) 5-Chloro-2-(3-cyclopentyloxy-4-methoxy-phenyl)-7-[3-(N-t-butoxycarbonyl-N-hydroxy-amino)-1-propynyl]-benzoxazole.

1.00 g (1.6 mmol) of 5-chloro-2-(3-cyclopentyloxy-4-methoxy-phenyl)-7-[3-(N-t-butyloxycarbonyl-N-t-butoxycarbonyloxy-amino)-1-propynyl]-benzoxazole was dissolved in 20 ml of THF and treated with 20 g of ammonia in a reactor. The pressure rose to 100 psi. After 2 hours, the solvents were removed in vacuo. Crystallization from methanol and recrystallization from di-isopropyl ether gave the title compound (0.47 g, 56.2%), mp 157–61° C.

While the invention has been illustrated with respect to the production and use of a particular compound, it was apparent that variations and modifications of the invention can be made without departing from the spirit or scope of the invention.

What is claimed is:

1. A compound of the formula:

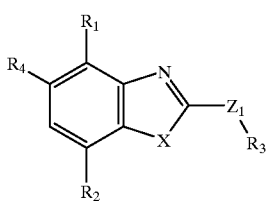

(I)

wherein:

X is O;

$R_1$ is selected from hydrogen, hydroxy, $QZ_2$, $OQZ_2$ or $OCOQZ_2$;

$R_4$ is hydrogen or halogen;

$Z_1$ is selected from —$CH_2$—, —$CH_2$—$CH_2$—, —CH($CH_3$)—, or —C($CH_3$)$_2$—;

$R_3$ is a six membered carbocyclic aryl substituted with 1–3 members of the group consisting of halogen, O—(CO)($C_1$-$C_6$)alkyl, O—($C_1$-$C_6$) alkyl, O—($C_3$-$C_{10}$)cycloalkyl or a $C_1$-$C_{12}$ branched or straight chain alkyl;

$R_2$ is selected from hydrogen, halogen, nitro, $QZ_2$, $NHQZ_2$;

Q is a bond, a saturated or unsaturated straight-chain or branched alkylene, alkenylene or alkynylene containing 1 to 12 Carbon atoms; and $Z_2$ is hydrogen, N(QH)$_2$, OQH, COQH, CO$_2$QH, N(OH) CON(QH)$_2$, NHCON(QH)$_2$, CON(OH)QH, CON(QH)$_2$, OCON(QH)$_2$, CH=NOCON(QH)$_2$;

provided that both $R_1$ and $R_2$ are not hydrogen or when $R_1$ is hydrogen, then $R_2$ is not halogen;

and pharmaceutically acceptable salts thereof.

2. A compound according to claim 1 wherein $R_3$ is 3-cyclopentyloxy-4-methoxy-phenyl.

3. A compound according to claim 1 wherein $R_4$ is chlorine.

4. A compound according to claim 1 wherein Q is an alkylene.

5. A compound according to claim 1 wherein Q is an alkenylene.

6. A compound according to claim 1 wherein Q is an alkynylene.

7. A compound according to claim 4 wherein said alkylene is —$CH_2$—, —$CH_2$—$CH_2$— or $CH_2$—$CH_2$—$CH_2$—.

8. A compound according to claim 4 wherein said alkenylene is —CH=CH—, or —$CH_2$—CH=CH— or —CH=CH—$CH_2$—.

9. A compound according to claim 6 wherein said alkynylene is —C≡C—, —C≡C—$CH_2$— or —$CH_2$—C≡C—.

10. The compound of claim 1, wherein one of $R_1$ and $R_2$ is hydrogen.

11. A compound according to claim 1, selected from the group consisting of:

2-(3-cyclopentyloxy-4-methoxy-benzyl)-5-chloro-7-allyl-benzoxazole;

2-(3-cyclopentyloxy-4-methoxy-benzyl)-5-chloro-7-propyl-benzoxazole;

2-(3-cyclopentyloxy-4-methoxy-benzyl)-5-chloro-7-(2-hydroxyethyl)benzoxazole;

2-(3-cyclopentyloxy-4-methoxy-benzyl)-5-chloro-7-(2-hydroxyethyl)benzoxazole carbamate;

2-(3-cyclopentyloxy-4-methoxy-benzyl)-5-chlorobenzoxazole-7-acetic acid;

2-(3-cyclopentyloxy-4-methoxy-benzyl)-5-chloro-7-(3-hydroxy-1-propynyl)-benzoxazole;

2-(3-cyclopentyloxy-4-methoxy-phenylethyl)-5-chloro-7-(3-hydroxy-1-propynyl)-benzoxazole;

2-(3-cyclopentyloxy-4-methoxy-benzyl)-5-chloro-7-(3-hydroxy-1-propyl)-benzoxazole;

2-(3-cyclopentyloxy-4-methoxy-phenylethyl)-5-chloro-7-(3-hydroxy-1-propyl)-benzoxazole;

5-chloro-2-(3-cyclopentyloxy-4-methoxy-phenylethyl)-7-propionic acid-benzoxazole;

7-(3-hydroxy-1-propyl)-2-(3,4-dimethoxybenzyl) benzoxazole and pharmaceutically acceptable salts thereof.

12. A compound according to claim 1, wherein said compound is selected from the group consisting of:

2-(3-cyclopentyloxy-4-methoxy-benzyl)-5-chlorobenzoxazole-7-acetamide;

2-(3-cyclopentyloxy-4-methoxy-benzyl)-5-chlorobenzoxazole-7-ethanal;

2-(3-cyclopentyloxy-4-methoxy-benzyl)-5-chlorobenzoxazole-7-ethanal oxime carbamate;

2-(3-cyclopentyloxy-4-methoxy-benzyl)-7-nitro-benzoxazole;

2-(3-cyclopentyloxy-4-methoxy-benzyl)-7-amino-benzoxazole;

2-(3-cyclopentyloxy-4-methoxybenzyl)-4-methoxy-benzoxazole;

2-(3-cyclopentyloxy-4-methoxybenzyl)-4-hydroxy-benzoxazole;

4-acetoxy-2-(3-cyclopentyloxy-4-methoxybenzyl)-benzoxazole and pharmaceutically acceptable salts thereof.

13. A compound according to claim 1, selected from the group consisting of:

7-(3-hydroxy-1-propynyl)-2-(3,5-di-t-butyl-4-acetoxy-benzyl)-5-chloro-benzoxazole; and pharmaceutically acceptable salts thereof.

14. A compound according to claim 1 wherein:

$R_1$ is hydrogen;

$R_3$ is a six membered carbocyclic aryl substituted with 1–3 halogens; and $R_2$ is selected from halogen, $QZ_2$, $NHQZ_2$.

15. A compound according to claim 14 wherein $R_4$ is chlorine.

16. A compound according to claim 14, wherein $R_3$ is 2,6-dichloro-phenyl.

17. A compound according to claim 14, wherein $R_3$ is 2,4-dichloro-phenyl.

18. A compound according to claim 14, wherein $R_3$ is 2-chloro-6-flouro-phenyl.

19. A compound according to claim 14, selected from the group consisting of:

5-chloro-7-(3-hydroxy-1-propynyl)-2-(2-chloro-6-fluoro-benzyl)-benzoxazole;

5-chloro-7-(3-hydroxy-1-propyl)-2-(2-chloro-6-fluoro-benzyl)-benzoxazole;

5-chloro-2-(2-chloro-6-fluoro-benzyl)-benzoxazole-7-propionic acid;

5-chloro-7-(3-hydroxy-1-propynyl)-2-(2,6-dichlorobenzyl)-benzoxazole;

5-chloro-7-(3-hydroxy-1-propyl)-2-(2,6-dichlorobenzyl)-benzoxazole;

5-chloro-7-(3-hydroxy-1-propynyl)-2-(2,4-dichlorobenzyl)-benzoxazole;

5-chloro-7-(3-hydroxy-1-propyl)-2-(2,4-dichlorobenzyl)-benzoxazole;

5-chloro-7-(3-hydroxy-1-propynyl)-2-[2-(2-chlorophenyl)ethyl]-benzoxazole;

5-chloro-7-(3-hydroxy-1-propyl)-2-[2-(2-chlorophenyl)ethyl]-benzoxazole;

5-chloro-7-(3-hydroxy-1-propyl)-2-(2-chlorobenzyl)-benzoxazole;

5-chloro-7-(3-hydroxy-1-propynyl)-2-(2-chlorobenzyl)-benzoxazole;

7-(3-hydroxy-1-propyl)-2-(2-chlorobenzyl)-benzoxazole;

5-chloro-7-allyl-2-(2-chlorobenzyl)-benzoxazole;

5-chloro-7-(3-methoxy-1-propyl)-2-(2-chlorobenzyl)-benzoxazole;

5-chloro-2-(2-chlorobenzyl)-benzoxazole-7-propanamide;

5-chloro-7-(5-hydroxy-1-pentyl)-2-(2-chlorobenzyl)-benzoxazole;

5-chloro-7-(5-hydroxy-1-pentynyl)-2-(2-chlorobenzyl)-benzoxazole;

5-chloro-7-(3-hydroxy-1-propyl)-2-(3-chlorobenzyl)-benzoxazole;

5-chloro-7-(3-hydroxy-1-propyl)-2-(4-chlorobenzyl)-benzoxazole;

5-chloro-7-(3-hydroxy-1-propynyl)-2-(4-chlorobenzyl)-benzoxazole;

5-chloro-7-(3-hydroxy-1-propyl)-2-(2-fluorobenzyl)-benzoxazole;

5-chloro-7-(3-hydroxy-1-propynyl)-2-(2-fluorobenzyl)-benzoxazole and pharmaceutically acceptable salts thereof.

20. A compound according to claim 1 wherein $R_1$ is hydrogen;

$R_4$ is halogen;

$R_3$ is a six membered carbocyclic aryl substituted with 1–3 members of the group consisting of O—($C_1$–$C_6$) alkyl, O—($C_3$–$C_{10}$)cycloalkyl;

$R_2$ is selected from halogen or $QZ_2$; and $Z_2$ is selected from hydrogen or OQH.

21. A compound according to claim 20, selected from the group consisting of:

7-(3-hydroxy-1-propynyl)-5-chloro-2-(3,4-dimethoxybenzyl)benzoxazole;

7-(3-hydroxy-1-propyl)-5-chloro-2-(3,4-dimethoxybenzyl)benzoxazole; and pharmaceutically acceptable salts thereof.

22. A pharmaceutical composition comprising a compound of the structure of the formula:

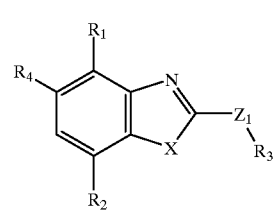

(I)

wherein:

X is O;

$R_1$ is selected from hydrogen, hydroxy, $QZ_2$, $OQZ_2$ or $OCOQZ_2$;

$R_4$ is hydrogen or halogen;

$Z_1$ is selected from —$CH_2$—, —$CH_2$—$CH_2$—, —CH($CH_3$)—, or —C($CH_3$)$_2$—;

$R_3$ is a six membered carbocyclic aryl substituted with 1–3 members of the group consisting of halogen, O—(CO)($C_1$–$C_6$)alkyl, O—($C_1$–$C_6$)alkyl, O—($C_3$–$C_{10}$)cycloalkyl or a $C_1$–$C_{12}$ branched or straight chain alkyl;

$R_2$ is selected from hydrogen, halogen, nitro, $QZ_2$, $NHQZ_2$;

Q is a bond, a saturated or unsaturated straight-chain or branched alkylene, alkenylene or alkynylene containing 1 to 12 Carbon atoms; and $Z_2$ is hydrogen, N(QH)$_2$, OQH, COQH, CO$_2$QH, N(OH)CON(QH)$_2$, NHCON(QH)$_2$, CON(OH)QH, CON(QH)$_2$, OCON(QH)$_2$, CH=NOCON(QH)$_2$;

provided that both $R_1$ and $R_2$ are not hydrogen or when $R_1$ is hydrogen, then $R_2$ is not halogen and pharmaceutically acceptable salts thereof.

23. The pharmaceutical composition of claim 22 which is suitable for oral administration.

24. The pharmaceutical composition of claim 22 which is suitable for parenteral administration.

25. The pharmaceutical composition of claim 22 which is suitable for administration by inhalation.

26. The composition of claim 22, wherein one of $R_1$ and $R_2$ is hydrogen.

27. The pharmaceutical composition of claim 22, wherein said compound is selected from the group consisting of:

2-(3-cyclopentyloxy-4-methoxy-benzyl)-5-chloro-7-allyl-benzoxazole;

2-(3-cyclopentyloxy-4-methoxy-benzyl)-5-chloro-7-propyl-benzoxazole;

2-(3-cyclopentyloxy-4-methoxy-benzyl)-5-chloro-7-(2-hydroxyethyl)benzoxazole;

2-(3-cyclopentyloxy-4-methoxy-benzyl)-5-chloro-7-(2-hydroxyethyl)benzoxazole carbamate;

2-(3-cyclopentyloxy-4-methoxy-benzyl)-5-chlorobenzoxazole-7-acetic acid;

2-(3-cyclopentyloxy-4-methoxy-benzyl)-5-chloro-7-(3-hydroxy-1-propynyl)-benzoxazole;

2-(3-cyclopentyloxy-4-methoxy-phenylethyl)-5-chloro-7-(3-hydroxy-1-propynyl)-benzoxazole;

2-(3-cyclopentyloxy-4-methoxy-benzyl)-5-chloro-7-(3-hydroxy-propyl)-benzoxazole;

2-(3-cyclopentyloxy-4-methoxy-phenylethyl)-5-chloro-7-(3-hydroxy-propyl)-benzoxazole;

7-(3-hydroxy-1-propyl)-2-(3,4-dimethoxybenzyl)benzoxazole;

5-chloro-2-(3-cyclopentyloxy-4-methoxy-phenylethyl)-7-propionic acid-benzoxazole and pharmaceutically acceptable salts thereof.

28. The pharmaceutical composition of claim 22, wherein said compound is selected from the group consisting of:

2-(3-cyclopentyloxy-4-methoxy-benzyl)-5-chlorobenzoxazole-7-acetamide;

2-(3-cyclopentyloxy-4-methoxy-benzyl)-5-chlorobenzoxazole-7-ethanal;

2-(3-cyclopentyloxy-4-methoxy-benzyl)-5-chlorobenzoxazole-7-ethanal oxime carbamate;

2-(3-cyclopentyloxy-4-methoxy-benzyl)-7-nitro-benzoxazole;

2-(3-cyclopentyloxy-4-methoxy-benzyl)-7-amino-benzoxazole;

2-(3-cyclopentyloxy-4-methoxybenzyl)-4-methoxy-benzoxazole;

2-(3-cyclopentyloxy-4-methoxybenzyl)-4-hydroxy-benzoxazole;

4-acetoxy-2-(3-cyclopentyloxy-4-methoxybenzyl)-benzoxazole and pharmaceutically acceptable salts thereof.

29. The pharmaceutical composition of claim 22, wherein said compound is selected from the group consisting of:

7-(3-hydroxy-1-propynyl)-2-(3,5-di-t-butyl-4-acetoxy-benzyl)-5-chloro-benzoxazole; and pharmaceutically acceptable salts thereof.

30. The pharmaceutical composition of claim 22 wherein:

$R_1$ is hydrogen;

$R_3$ is a six membered carbocyclic aryl substituted with 1–3 halogens; and $R_2$ is selected from halogen, $QZ_2$, $NHQZ_2$.

31. The pharmaceutical composition of claim 30, wherein said compound is selected from the group consisting of:

5-chloro-7-(3-hydroxy-1-propynyl)-2-(2-chloro-6-fluoro-benzyl)-benzoxazole;

5-chloro-7-(3-hydroxy-1-propyl)-2-(2-chloro-6-fluoro-benzyl)-benzoxazole;

5-chloro-2-(2-chloro-6-fluoro-benzyl)-benzoxazole-7-propionic acid;

5-chloro-7-(3-hydroxy-1-propynyl)-2-(2,6-dichlorobenzyl)-benzoxazole;

5-chloro-7-(3-hydroxy-1-propyl)-2-(2,6-dichlorobenzyl)-benzoxazole;

5-chloro-7-(3-hydroxy-1-propynyl)-2-(2,4-dichlorobenzyl)-benzoxazole;

5-chloro-7-(3-hydroxy-1-propyl)-2-(2,4-dichlorobenzyl)-benzoxazole;

5-chloro-7-(3-hydroxy-1-propynyl)-2-[2-(2-chlorophenyl)ethyl]-benzoxazole;

5-chloro-7-(3-hydroxy-1-propyl)-2-[2-(2-chlorophenyl)ethyl]-benzoxazole;

5-chloro-7-(3-hydroxy-1-propyl)-2-(2-chlorobenzyl)-benzoxazole;

5-chloro-7-(3-hydroxy-1-propynyl)-2-(2-chlorobenzyl)-benzoxazole;

7-(3-hydroxy-1-propyl)-2-(2-chlorobenzyl)-benzoxazole;

5-chloro-7-allyl-2-(2-chlorobenzyl)-benzoxazole;

5-chloro-7-(3-methoxy-1-propyl)-2-(2-chlorobenzyl)-benzoxazole;

5-chloro-2-(2-chlorobenzyl)-benzoxazole-7-propanamide;

5-chloro-7-(5-hydroxy-1-pentyl)-2-(2-chlorobenzyl)-benzoxazole;

5-chloro-7-(5-hydroxy-1-pentynyl)-2-(2-chlorobenzyl)-benzoxazole;

5-chloro-7-(3-hydroxy-1-propyl)-2-(3-chlorobenzyl)-benzoxazole;

5-chloro-7-(3-hydroxy-1-propyl)-2-(4-chlorobenzyl)-benzoxazole;

5-chloro-7-(3-hydroxy-1-propynyl)-2-(4-chlorobenzyl)-benzoxazole;

5-chloro-7-(3-hydroxy-1-propyl)-2-(2-fluorobenzyl)-benzoxazole;

5-chloro-7-(3-hydroxy-1-propynyl)-2-(2-fluorobenzyl)-benzoxazole and pharmaceutically acceptable salts thereof.

32. The pharmaceutical composition of claim 22 wherein:

$R_1$ is hydrogen;

$R_4$ is halogen;

$R_3$ is a six membered carbocyclic aryl substituted with 1–3 members of the group consisting of O—($C_1$–$C_6$) alkyl, O—($C_3$–$C_{10}$)cycloalkyl;

$R_2$ is selected from halogen or $QZ_2$; and $Z_2$ is selected from hydrogen or OQH.

33. The pharmaceutical composition of claim 32, wherein said compound is selected from the group consisting of:

7-(3-hydroxy-1-propynyl)-5-chloro-2-(3,4-dimethoxybenzyl)benzoxazole;

7-(3-hydroxy-1-propyl)-5-chloro-2-(3,4-dimethoxybenzyl)benzoxazole; and pharmaceutically acceptable salts thereof.

34. A method of treating a mammal suffering from a disease state selected from the group consisting of asthma, allergies, inflammation, depression, dementia, atopic diseases, rhinitis and disease states associated with abnormally high physiological levels of a member of the group consisting of cytokines, inflammatory cytokines and chemokines, comprising administering an effective amount of a compound of the formula:

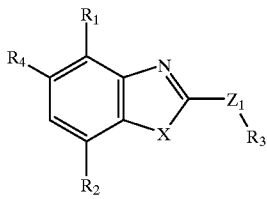

(I)

wherein:
X is O;
$R_1$ is selected from hydrogen, hydroxy, $QZ_2$, $OQZ_2$ or $OCOQZ_2$;
$R_4$ is hydrogen or halogen;
$Z_1$ is selected from $—CH_2—$, $—CH_2—CH_2—$, $—CH(CH_3)—$, or $—C(CH_3)_2—$;
$R_3$ is a six membered carbocyclic aryl optionally substituted with 1–3 members of the group consisting of halogen, O—(CO)($C_1$–$C_6$)alkyl, O—($C_1$–$C_6$)alkyl, O—($C_3$–$C_{10}$)cycloalkyl or a $C_1$–$C_{12}$ branched or straight chain alkyl;
$R_2$ is selected from hydrogen, halogen, nitro, $QZ_2$, $NHQZ_2$;
Q is a bond, a saturated or unsaturated straight-chain or branched alkylene, alkenylene or alkynylene containing 1 to 12 Carbon atoms; and
$Z_2$ is hydrogen, $N(QH)_2$, OQH, COQH, $CO_2QH$, N(OH)CON(QH)$_2$, NHCON(QH)$_2$, CON(OH)QH, CON(QH)$_2$, OCON(QH)$_2$, CH=NOCON(QH)$_2$;
provided that when $Z_1$-$R_3$ is unsubstituted phenylalkyl, $R_2$ is not an alkylamine, both $R_1$ and $R_2$ are not hydrogen or when $R_1$ is hydrogen, then $R_2$ is not halogen and pharmaceutically acceptable salts thereof.

35. The method of claim 34, wherein one of $R_1$ and $R_2$ is hydrogen.

36. The method of claim 34, wherein said compound is selected from the group consisting of:
2-(3-cyclopentyloxy-4-methoxy-benzyl)-5-chloro-7-allyl-benzoxazole;
2-(3-cyclopentyloxy-4-methoxy-benzyl)-5-chloro-7-propyl-benzoxazole;
2-(3-cyclopentyloxy-4-methoxy-benzyl)-5-chloro-7-(2-hydroxyethyl)benzoxazole;
2-(3-cyclopentyloxy-4-methoxy-benzyl)-5-chloro-7-(2-hydroxyethyl)benzoxazole carbamate;
2-(3-cyclopentyloxy-4-methoxy-benzyl)-5-chlorobenzoxazole-7-acetic acid;
2-(3-cyclopentyloxy-4-methoxy-benzyl)-5-chloro-7-(3-hydroxy-1-propynyl)-benzoxazole;
2-(3-cyclopentyloxy-4-methoxy-phenylethyl)-5-chloro-7-(3-hydroxy-1-propynyl)-benzoxazole;
2-(3-cyclopentyloxy-4-methoxy-benzyl)-5-chloro-7-(3-hydroxy-1-propyl)-benzoxazole;
2-(3-cyclopentyloxy-4-methoxy-phenylethyl)-5-chloro-7-(3-hydroxy-1-propyl)-benzoxazole;
5-chloro-2-(3-cyclopentyloxy-4-methoxy-phenylethyl)-7-propionic acid-benzoxazole
5-chloro-7-(3-hydroxy-1-propyl)-2-benzyl-benzoxazole;
5-chloro-7-(3-hydroxy-1-propynyl)-2-benzyl-benzoxazole;
7-(3-hydroxy-1-propyl)-2-(3,4-dimethoxybenzyl)benzoxazole and
pharmaceutically acceptable salts thereof.

37. The method of claims 34, wherein said compound is selected from the group consisting of:
2-(3-cyclopentyloxy-4-methoxy-benzyl)-5-chlorobenzoxazole-7-acetamide;
2-(3-cyclopentyloxy-4-methoxy-benzyl)-5-chlorobenzoxazole-7-ethanal;
2-(3-cyclopentyloxy-4-methoxy-benzyl)-5-chlorobenzoxazole-7-ethanal oxime carbamate;
2-(3-cyclopentyloxy-4-methoxy-benzyl)-7-nitrobenzoxazole;
2-(3-cyclopentyloxy-4-methoxy-benzyl)-7-aminobenzoxazole;
2-(3-cyclopentyloxy-4-methoxybenzyl)-4-methoxybenzoxazole;
2-(3-cyclopentyloxy-4-methoxybenzyl)-4-hydroxybenzoxazole;
4-acetoxy-2-(3-cyclopentyloxy-4-methoxybenzyl)-benzoxazole and
pharmaceutically acceptable salts thereof.

38. The method of claim 34, wherein said compound is selected from the group consisting of:
7-(3-hydroxy-1-propynyl)-2-(3,5-di-t-butyl-4-acetoxybenzyl)-5-chloro-benzoxazole; and
pharmaceutically acceptable salts thereof.

39. The method of claim 34, wherein:
$R_1$ is hydrogen;
$R_3$ is a six membered carbocyclic aryl substituted with 1–3 halogens; and
$R_2$ is selected from halogen, $QZ_2$, $NHQZ_2$.

40. The method of claim 39, wherein said compound is selected from by the group consisting of:
5-chloro-7-(3-hydroxy-1-propynyl)-2-(2-chloro-6-fluoro-benzyl)-benzoxazole;
5-chloro-7-(3-hydroxy-1-propyl)-2-(2-chloro-6-fluoro-benzyl)-benzoxazole;
5-chloro-2-(2-chloro-6-fluoro-benzyl)-benzoxazole-7-propionic acid;
5-chloro-7-(3-hydroxy-1-propynyl)-2-(2,6-dichlorobenzyl)-benzoxazole;
5-chloro-7-(3-hydroxy-1-propyl)-2-(2,6-dichlorobenzyl)-benzoxazole;
5-chloro-7-(3-hydroxy-1-propynyl)-2-(2,4-dichlorobenzyl)-benzoxazole;
5-chloro-7-(3-hydroxy-1-propyl)-2-(2,4-dichlorobenzyl)-benzoxazole;
5-chloro-7-(3-hydroxy-1-propynyl)-2-[2-(2-chlorophenyl)ethyl]-benzoxazole;
5-chloro-7-(3-hydroxy-1-propyl)-2-[2-(2-chlorophenyl)ethyl]-benzoxazole;
5-chloro-7-(3-hydroxy-1-propyl)-2-(2-chlorobenzyl)-benzoxazole;
5-chloro-7-(3-hydroxy-1-propynyl)-2-(2-chlorobenzyl)-benzoxazole;
7-(3-hydroxy-1-propyl)-2-(2-chlorobenzyl)-benzoxazole;

5-chloro-7-allyl-2-(2-chlorobenzyl)-benzoxazole;

5-chloro-7-(3-methoxy-1-propyl)-2-(2-chlorobenzyl)-benzoxazole;

5-chloro-2-(2-chlorobenzyl)-benzoxazole-7-propanamide;

5-chloro-7-(5-hydroxy-1-pentyl)-2-(2-chlorobenzyl)-benzoxazole;

5-chloro-7-(5-hydroxy-1-pentynyl)-2-(2-chlorobenzyl)-benzoxazole;

5-chloro-7-(3-hydroxy-1-propyl)-2-(3-chlorobenzyl)-benzoxazole;

5-chloro-7-(3-hydroxy-1-propyl)-2-(4-chlorobenzyl)-benzoxazole;

5-chloro-7-(3-hydroxy-1-propynyl)-2-(4-chlorobenzyl)-benzoxazole;

5-chloro-7-(3-hydroxy-1-propyl)-2-(2-fluorobenzyl)-benzoxazole;

5-chloro-7-(3-hydroxy-1-propynyl)-2-(2-fluorobenzyl)-benzoxazole and pharmaceutically acceptable salts thereof.

41. The method of claim 34 wherein;

$R_1$ is hydrogen;

$R_4$ is halogen;

$R_3$ is a six membered carbocyclic aryl substituted with 1–3 members of the group consisting of O—($C_1$–$C_6$) alkyl, O—($C_3$–$C_{10}$)cycloalkyl;

$R_2$ is selected from halogen or $QZ_2$; and $Z_2$ is selected from hydrogen or OQH.

42. The method of claim 41, wherein said compound is selected from the group consisting of:

7-(3-hydroxy-1-propynyl)-5-chloro-2-(3,4-dimethoxybenzyl)benzoxazole;

7-(3-hydroxy-1-propyl)-5-chloro-2-(3,4-dimethoxybenzyl)benzoxazole; and pharmaceutically acceptable salts thereof.

43. A method of effecting selective PDE IV inhibition to a patient suffering from a disease state selected from the group consisting of asthma, allergies, inflammation, depression, atopic diseases and rhinitis which comprises administering an effective amount of the compound of claim 1 to said patient.

44. A compound selected from the group consisting of:

7-bromo-5-chloro-2-(3,4-dimethoxyphenyl)benzoxazole;

7-(3-hydroxy-1-propynyl)-5-chloro-2-(3,4-dimethoxyphenyl)benzoxazole;

7-(3-hydroxy-1-propyl)-5-chloro-2-(3,4-dimethoxyphenyl)benzoxazole;

2-(3-cyclopentyloxy-4-methoxy-phenyl)-5-chloro-7-(3-hydroxy-1-propynyl)-benzoxazole;

2-(3-cyclopentyloxy-4-methoxy-phenyl)-5-chloro-7-bromo-benzoxazole;

5-chloro-2-(3,4-dimethoxyphenyl)benzoxazole;

5-chloro-2-(2-chlorophenyl)-7-(3-carbamido-1-propynyl)-benzoxazole;

5-chloro-2-(2-chlorophenyl)-7-(3-carbamido-1-propyl)-benzoxazole;

5-chloro-2-(2-chlorophenyl)-7-[3-(N'-hydroxycarbamido)butyl]-benzoxazole;

5-chloro-2-(3-chlorophenyl)-benzoxazole-7-(N-hydroxy-N-methyl-propanamide);

2-(3-chlorophenyl)-7-(3-cyclopentyloxy-4-methoxy-benzylamino)benzoxazole;

4-(5-chloro-2-(2-chlorophenyl)benzoxazol-7-yl)butan-2-one and pharmaceutically acceptable salts thereof.

45. A pharmaceutical composition comprising a compound of claim 44 and a pharmaceutically acceptable carrier.

46. A method of treating a mammal suffering from a disease state selected from the group consisting of asthma, allergies, inflammation, depression, dementia, atopic diseases, rhinitis and disease states associated with abnormally high physiological levels of a member of the group consisting of cytokines, inflammatory cytokines and chemolines, comprising administering an effective amount of a compound of claim 44.

* * * * *